United States Patent [19]

Croslin

[11] 4,338,949

[45] Jul. 13, 1982

[54] METHOD FOR PERFORMING NON-INVASIVE BLOOD PRESSURE AND PULSE RATE MEASUREMENTS

[76] Inventor: Michael E. Croslin, 37 Bow St., Forest Hills Gardens, N.Y. 11375

[21] Appl. No.: 212,120

[22] Filed: Dec. 2, 1980

Related U.S. Application Data

[60] Division of Ser. No. 64,194, Aug. 6, 1979, Pat. No. 4,271,844, which is a continuation-in-part of Ser. No. 499, Jan. 2, 1979, abandoned, and a continuation-in-part of Ser. No. 774,970, Mar. 7, 1977, abandoned.

[51] Int. Cl.³ .............................................. A61B 5/02

[52] U.S. Cl. .................................................. 128/677

[58] Field of Search ............... 128/677, 680, 681, 682, 128/683

[56] References Cited

U.S. PATENT DOCUMENTS

| | | | |
|---|---|---|---|
| 3,939,824 | 2/1976 | Arneson | 128/708 |
| 4,105,021 | 8/1978 | Williams et al. | 128/683 |
| 4,190,886 | 2/1980 | Sherman | 128/681 |
| 4,263,918 | 4/1981 | Swearingen et al. | 128/681 |

*Primary Examiner*—William E. Kamm
*Attorney, Agent, or Firm*—Gottlieb, Rackman & Reisman

[57] ABSTRACT

There is disclosed a blood pressure measuring instrument which utilizes a standard cuff, a bulb for manually pumping up the cuff pressure, and a bleed hole which allows the cuff pressure to decrease at the rate of a few mm Hg per second. A single pressure transducer is in communication with the cuff interior and its output is sampled at a rate much higher than that of the blood pressure pulses. The sampled data, representing the occluding pressure which is being pumped up or bleeding down, with blood pressure pulses superimposed on it, are used to monitor the pump-up procedure and to determine when the artery is completely occluded, to analyze each blood pressure pulse for validating it and for measuring its amplitude, to determine systolic pressure only if the pulse amplitude sequence is a valid sequence, to determine diastolic pressure by comparing decreasing average pulse amplitudes with a threshold level dependent upon maximum pulse amplitude data, and to determine pulse rate in accordance with the number of pulses detected during a fixed time interval. A display circuit guides the operator as to the steps he must take in accordance with the present system state, and it displays both error messages and measurement values. The high reliability of the system is a consequence of the particular methodology employed during each processing step; the high sampling rate allows the system to follow instantaneous pressure changes, and the various analytical routines take full advantage of this capability.

20 Claims, 23 Drawing Figures

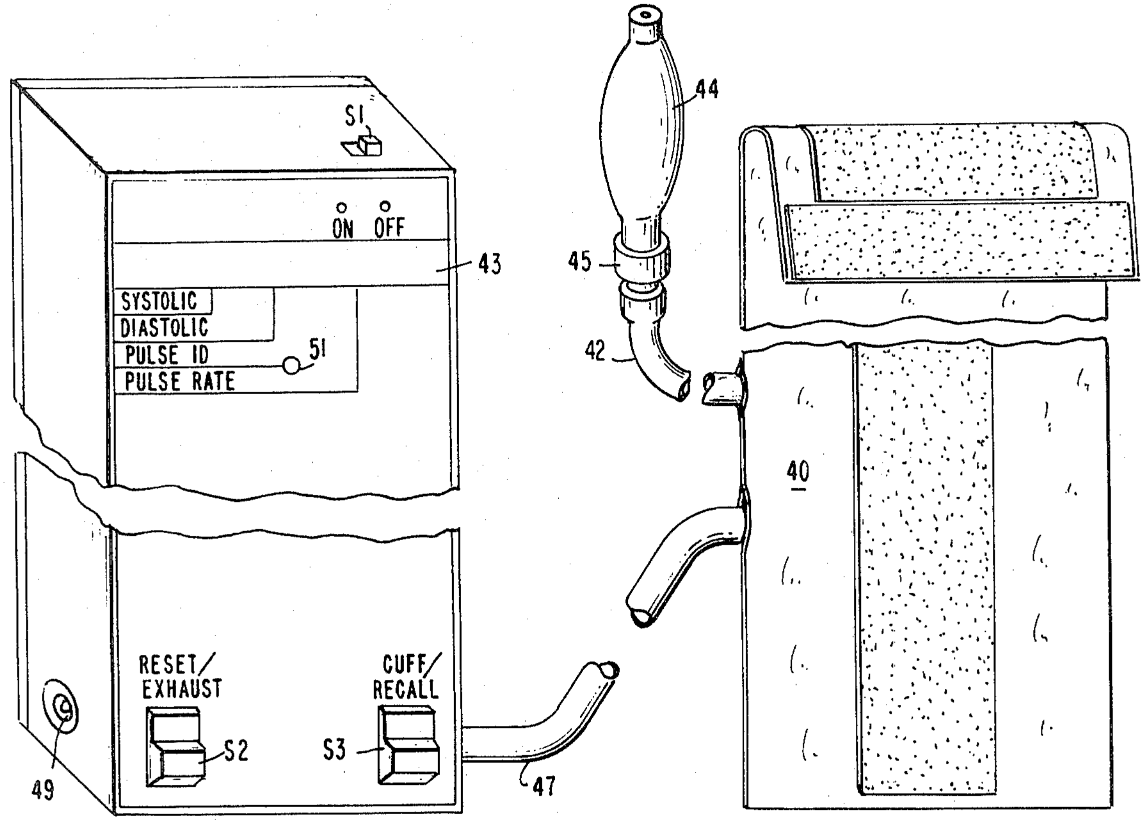
FIG. 1
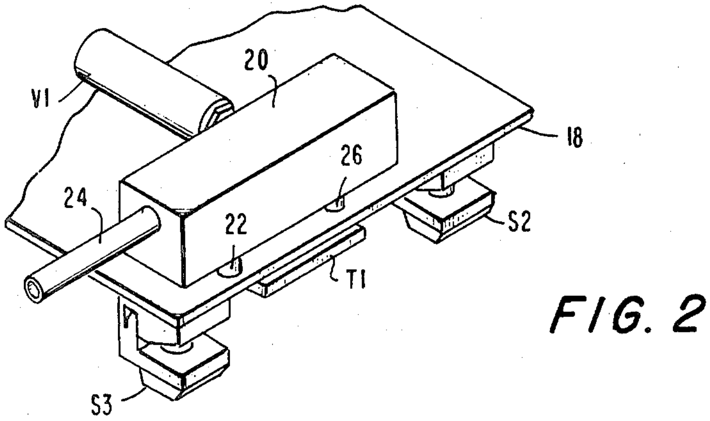
FIG. 2
FIG. 9

FIG. 6
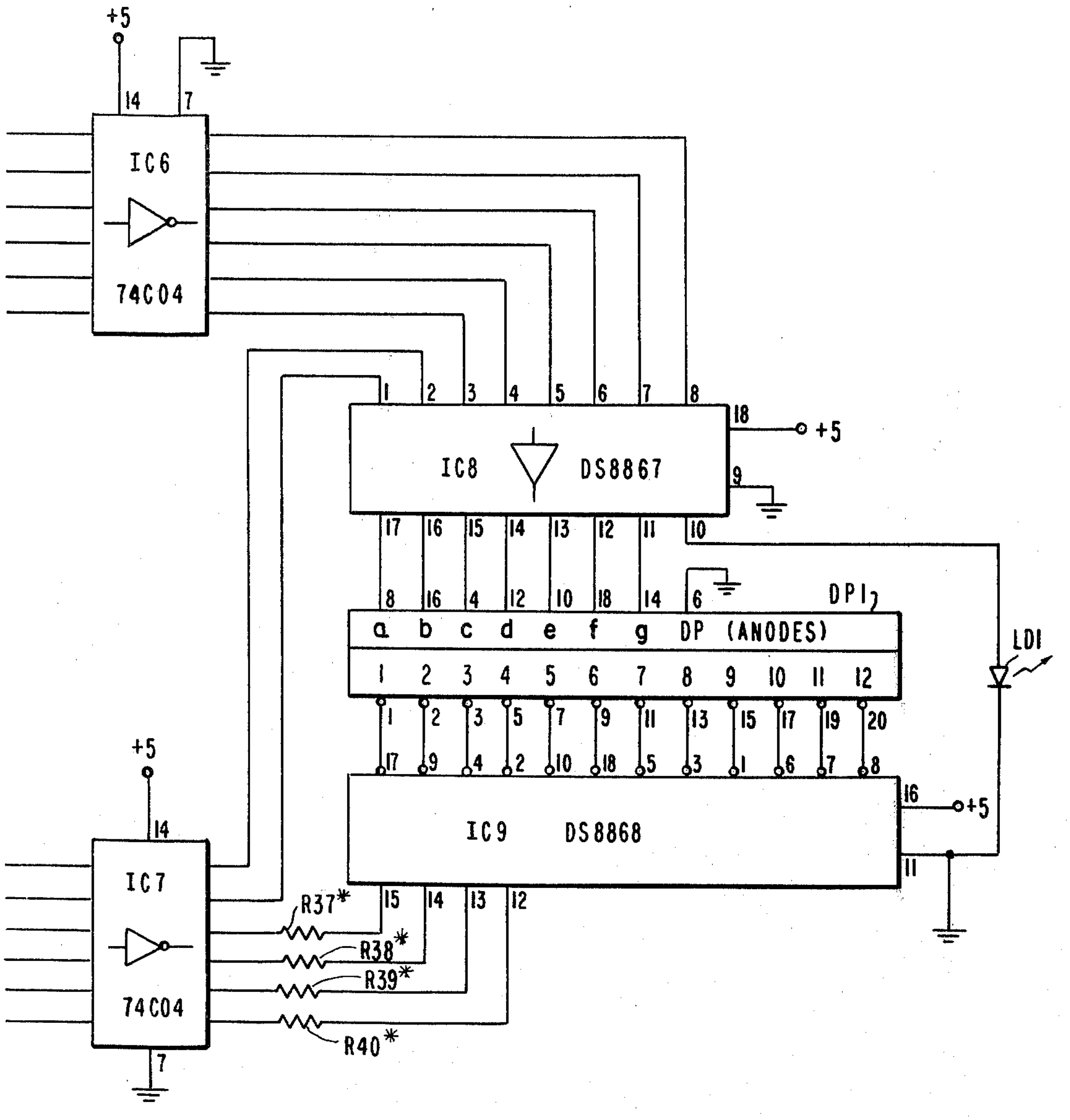
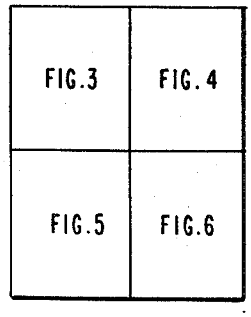
FIG. 7

METHOD FOR PERFORMING NON-INVASIVE BLOOD PRESSURE AND PULSE RATE MEASUREMENTS

This application is a division of my application Ser. No. 064,194, filed on Aug. 6, 1979 now U.S. Pat. No. 4,271,844. My invention relates to methods and apparatus for the non-invasive detection of arterial blood pressure and pulse rates, and more particularly to instruments which perform the measurements automatically and in a highly reliable manner, which application is a continuation-in-part of my application Ser. No. 000,499, filed Jan. 2, 1979 now abandoned and entitled "Method and Apparatus for Non-Invasive Detection of Arterial Blood Pressure and Pulse Rate, and Monitoring the Results of Analysis Apparatus", and a continuation-in-part of my application Ser. No. 774,970, filed Mar. 7, 1977 now abandoned and entitled "Method and Apparatus for Non-Invasive Detecting of Arterial Blood Pressure and Pulse Rate, and the Monitoring of Detected Results" (the former being a continuation-in-part of the latter), both of which applications are hereby incorporated by reference.

The oldest and most widely used technique for measuring the blood pressure of a patient is to completely occlude an artery by a pressurized cuff whose pressure is then allowed to bleed down. A mercury manometer is used to determine the pressure in the cuff, and a stethoscope is utilized to listen for Korotkoff sounds. The cuff pressures when particular types of sounds are heard are indications of systolic and diastolic pressures. The various methods based on listening for Korotkoff sounds are inherently inaccurate, especially when measuring diastolic pressure since what is required is a determination of the disappearance of sound as it gradually fades out. Even systolic pressure determinations are inaccurate because what is often thought to be a first pressure pulse, and sometimes even a second pressure pulse, are nothing more than artifacts which do not represent a flow of blood through the still fully occluded artery. A mean error of $\pm 8$ mm Hg can be expected in readings of systolic and diastolic pressures based on Korotkoff sounds. (Best and Taylor, *Physiological Basis of Medical Practice,* 9th Edition, Chapter 7, page 3-151.) Nor are present-day automatic instruments based on Korotkoff sounds any more reliable. Not only is it difficult to monitor electronically a fading sound, but the methodologies employed do not provide consistent, reliable results.

Other measurement approaches have met with equally little success. With respect to oscillometric methods, it is very difficult to determine diastolic pressure because one has to look for changes in oscillations of a mercury column, and they are barely noticeable with narrow-width pressure pulses. Hot-wire anemometer-type transducers offer somewhat better accuracy, but they require the use of two cuffs (occluding and sensing, in which the pressure in the sensing cuff is maintained constant). One of the shortcomings of these and other prior art devices is that two transducers and associated electronics are required.

Representative prior art, in addition to the Best and Taylor text referred to above, are the following:

| U.S. Pat. No. | Date | Inventor | Title |
|---|---|---|---|
| 2,827,040 | March 18, 1958 | S. R. Gilford | Automatic Sphygmomanometer |
| 3,224,435 | Dec. 21, 1965 | M. Traite | Method of Measuring Blood Pressure |
| 3,229,685 | Jan. 18 1966 | D. L. Ringkamp et al | Blood Pressure Measuring |
| 3,480,005 | Nov. 25, 1969 | W. C. Edwards | Apparatus for Measuring Blood Pressure With Plural Brake Controlled Indicators |
| 3,581,734 | June 1, 1971 | M. E. Croslin et al | Sphygmomanometer |
| 3,742,937 | July 3, 1973 | B. Manuel et al | Cardiac Monitor |
| 3,742,938 | July 3, 1973 | T. J. Stern | Cardiac Pacer and Heart Pulse Monitor |
| 3,814,083 | June 4, 1974 | J. C. Fletcher et al | Apparatus and Method For Processing Korotkov Sounds |
| 3,841,314 | Oct. 15, 1974 | R. E. Page | Pulse Activity Indicator |
| 3,885,551 | May 27, 1975 | H. L. Massie | Artifact Rejection For Blood Pressure Monitoring |
| 3,894,533 | July 15, 1975 | R. L. Cannon | Vital Sign Trend Intuitive Display System |
| 3,903,872 | Sept. 9, 1975 | W. T. Link | Apparatus and Process For Producing Sphygmometric Information |
| 3,978,848 | Sept. 7, 1976 | D. H. Yen et al | Monitoring Apparatus And Method For Blood Pressure and Heart Rate |
| 4,009,709 | March 1, 1977 | W. T. Link et al | Apparatus and Process For Determining Systolic Pressure |
| 4,074,711 | Feb. 21, 1978 | W. T. Link et al | Apparatus And Process For Determining Systolic Pressure |

Other Publications:

1. L. A. Geddes et al—"The Meaning of the Point of Maximum Oscillations in Cuff Pressure in the Indirect Measurement of Blood Pressure, Part I", Cardiovascular Research Center Bulletin, July-Sept., 1969, pages 15-25.

2. Physiological Basis of Medical Practice, Ninth Edition, John R. Brobeck: Chapter 7, Section 3—"-Measurement of Blood Pressure and Flow", pages 148-163; Chapter 8, Section 3—"Control Mechanisms of the Circulatory System", pages 164-188; Chapter 9, Section 3—"Regulation of Systemic and Pulmonary Circulation", pages 189-210.

3. George E. Burch—"Sphygmomanometric Cuff Size and Blood Pressure Recordings", JAMA, Sept. 3, 1973, Vol. 225, No. 10, pages 1215-1218.

4. Electronic Design, Vol. 24, No. 19, Sept. 13, 1976, page 28, "Semis invade medical transducers; microprocessors monitor EKG and blood pressure".

5. "Computer Automation of Blood-Pressure Measurements", Proceedings of the IEEE, Vol. 63, No. 10, October 1975, pages 1399-1403.

The basic problem with most prior art automated blood pressure measuring instruments is that they look for "gross" indications, e.g., the presence of a pulse based upon a sound level or some other parameter reaching a detectable level. From a theoretical standpoint, the most accurate measurement determinations could be made were the pressure waveform in the cuff actually traced out on paper during the course of a measurement cycle, much as is done in the case of ECG waveform analysis. The pressure waveform would show a decreasing occluding cuff pressure, on which blood pressure pulses are superimposed. Such a paper trace would provide to the physician the maximum amount of information from which systolic and diastolic pressures could be determined. If a trace is not to be made and an instrument is to perform the analysis, then ideally the processing section of the instrument should be provided with the exact waveform of the pressure in the cuff. It is possible to do this by sampling the cuff pressure at a sufficiently high rate and to then process the samples. If the sampling rate is so high that numerous samples are taken during the occurrence of each pulse, then from the standpoint of information theory the processing section of the instrument will have available sufficient data from which the complete waveform may be reconstructed.

However, while this general principle may have been recognized by prior art researchers, they have not employed effective methodologies in analyzing the sampled data. One problem in this regard is that the analysis must be done "on the fly". In the illustrative embodiment of the invention, a sample is taken approximately every 2.5 milliseconds; thus 400 samples are taken each second, and an 8k memory would be required to store the data for a measurement cycle of 20 seconds—if all of the data is to be stored prior to the actual processing which determines the final measurement values. A cost-effective instrument must therefore perform the processing as samples are taken without storing a complete history of the pressure waveform. The methodologies employed in the prior art for performing this type of "on-the-fly" processing have not provided accurate or consistent results.

For example, consider the methodology for systolic pressure determination disclosed in Link et al U.S. Pat. No. 4,009,709. Link et al theorize that the DC pressure in the cuff (the value of the slowly changing occluding pressure) when there is detected a blood pressure pulse whose amplitude is one-half of a maximum amplitude value represents the systolic pressure, where the maximum amplitude value is the maximum average amplitude over four successive pulses. In the Link et al instrument, a "sliding average" of the pulse amplitude over four successive pulses is taken, and a threshold level is constantly up-dated to equal the maximum sliding average. Link et al pump up the pressure continuously. As the occluding pressure increases, the pulse amplitudes rise and then fall. By using an increasing pressure during the measurement cycle, maximum pulse amplitudes are detected before the occluding pressure reaches the relatively high value which represents systolic pressure. It is in this way that the threshold level is determined before a pulse is actually detected whose amplitude is less than one-half of the threshold level. The Link et al technique requires a smooth pump-up of the cuff pressure and thus does not allow a cheap, conventional-type manually-operated bulb pump to be used. On the other hand, it is possible to use a bulb to pump up the pressure to a value which completely occludes the artery, and then to allow the pressure to bleed down smoothly as in conventional instruments. But in such a case, the systolic pressure is reached before the threshold level can even be determined. This, in turn, requires that a considerable amount of data be stored since "on-the-fly" processing is possible to only a limited extent.

But quite apart from the difficulties in implementing such a technique, the Link et al methodology has not proven to provide consistently correct systolic pressure measurements. The basic premise of Link et al is that the systolic pressure is the DC cuff pressure when a particular pulse is detected, and that particular pulse is the first one in a decreasing amplitude sequence whose amplitude corresponds to one-half of the maximum amplitude (or, more accurately, the maximum average amplitude over four successive pulses). This criterion has not been established, but even were it valid the Link et al system does not take into account the existence of artifacts. For example, if a patient moves his arm during the course of a measurement cycle and in the process squeezes the cuff, there will be a very large pressure rise which may control the maximum average pulse amplitude which is used as the threshold value—the threshold value and therefore the systolic pressure determination being completely erroneous in such a case.

What is important in an automated blood pressure measurement instrument is not only the selection of the proper criteria for determining systolic and diastolic pressures, but also validation of the results. Throughout the following detailed description of the invention, it will be noted that considerable attention is paid to validating the measurement cycle. One such example is the analysis of each individual pulse; a pulse is not considered to be valid if its amplitude is too large. Another example relates to the determination of systolic pressure. The sequence of pulse amplitudes in the region of systolic pressure must be one of plurality of predetermined valid sequences. It is this kind of constant concern for validating the measurement results (both intermediate and final) which contributes to reliable instrumentation.

In the illustrative embodiment of the invention a display is provided for guiding the operator—physician or patient—through the measurement cycle. As the bulb is used to pump up the cuff pressure, the operator is informed not only of the instantaneous cuff pressure, but also of the particular actions which are required. This, in and of itself, is an important feature of the invention. Furthermore, for a measurement cycle to provide accurate results, it is essential that the artery be completely occluded before the cuff pressure is monitored for the presence of pulses. What the system of the invention does is to check that no pulses have been detected for about 2.5 seconds before it assumes that the artery has been completely occluded and the cuff pressure should be allowed to continue bleeding down. If full occlusion for 2.5 seconds is not ascertained, the display informs the operator to pump up the cuff pressure.

The basic systolic pressure methodology involves an analysis of the amplitudes of four successive pulses, when pulses first appear as the occluding pressure bleeds down. (As will be described below, artifacts are rejected and it is not necessarily the first four pulse amplitudes which are operated upon.) Systolic pressure is taken to be the cuff pressure at the onset of a particular one of the four pulses, but only if the pulse amplitudes have a sequence which is one of a plurality of known valid sequences, e.g., four successive pulses exhibit increasing amplitudes, except for the third which may have the largest amplitude. There are quite a few valid sequences, some of which will be described in detail below.

The diastolic pressure methodology is actually similar to the Link et al methodology for determining systolic pressure. (There is no apparent reason why the same type of methodology should be effective to determine both systolic and diastolic pressures; in fact, it is not effective for systolic pressure determinations as taught by Link et al, but it is effective for diastolic pressure determinations.) A threshold value is determined based upon maximum pulse amplitude information; in the illustrative embodiment of the invention, the threshold level partially depends upon the maximum average pulse amplitude over four pulses. But the threshold value is not based solely upon the maximum amplitude information; it is also a function of a constant value. Moreover, instead of comparing the amplitude of a single pulse with the threshold value in order to determine diastolic pressure, the comparison involves the average pulse amplitude over four pulses in the vicinity of diastolic pressure.

The methodology of the invention does not lend itself to a more detailed general description. Suffice it to say that the method of the invention allows "on-the-fly" analysis of samples taken at a sufficiently high rate such that they allow the complete cuff pressure waveform to be reproduced. The criteria for determining systolic and diastolic pressures have proved to be accurate and reliable. Throughout the processing, validation checks are performed. Any indication of erroneous measurements having been taken results in an appropriate error message. Accurate measurements of pulse rates are also provided. In connection with a pulse rate measurement, while it is not particularly difficult to count detected pulses (as is known in the prior art), it is the rejection of a measurement cycle due to the presence of artifacts that gives rise to the high accuracy of my method and apparatus.

Further objects, features and advantages of my invention will become apparent upon consideration of the following detailed description in conjunction with the drawing, in which:

FIG. 1 is a perspective view of the instrument of my invention;

FIG. 2 depicts a portion of the circuit board within the housing of the instrument, and several of the components mounted on the board;

FIGS. 3-6 are a schematic of the circuit of the instrument, with the figures being arranged as shown in FIG. 7;

FIG. 9 depicts the seven segments of each display element, together with the fifteen characters which can be formed by energizing appropriate ones of the segments (the 16th character is a blank, obtained by energizing none of the segments);

Figure 22:
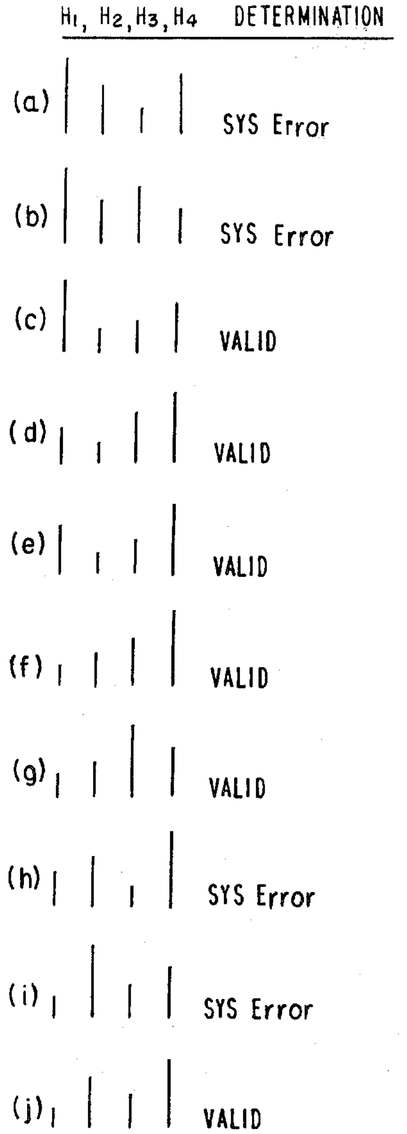
Figure 21:
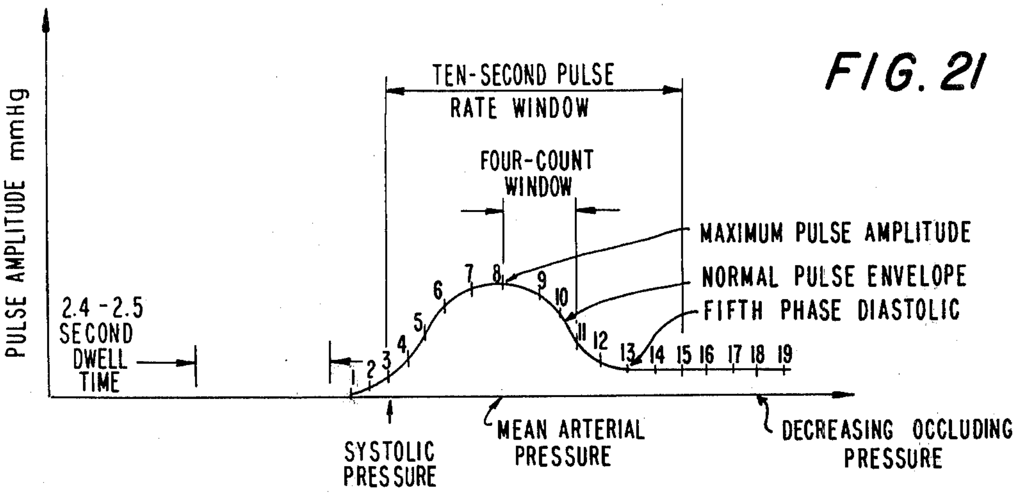
Figure 14:
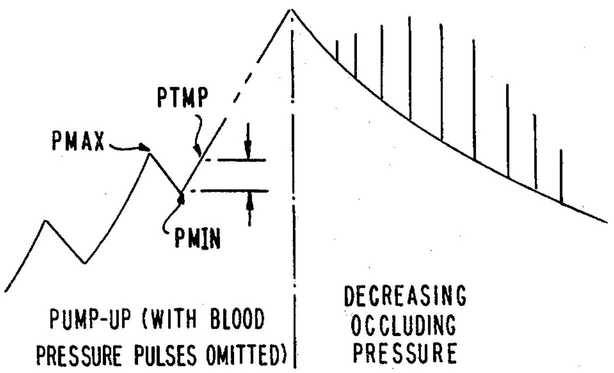
Figure 19:
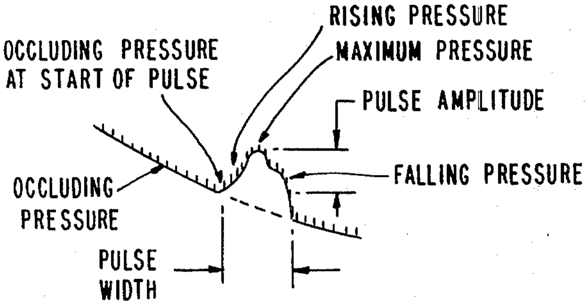

FIG. 14, which is not drawn to scale, depicts the cuff pressure throughout a measurement cycle;

FIG. 19 depicts, in enlarged scale, the cuff pressure in the vicinity of a single blood pressure pulse;

FIG. 21 depicts the envelope of the pulse amplitudes—not the cuff pressure, but just the amplitudes of individual pulses such as that shown in FIG. 19—throughout a measurement cycle; and FIG. 22 depicts several illustrative pulse sequences which will be discussed in conjunction with the systolic pressure measurement methodology.

HARDWARE

FIG. 1 depicts the instrument of my invention. It includes a conventional cuff 40, with tubing 42 connecting the cuff to pump-up bulb 44. As the bulb is pumped, the pressure in the cuff rises. There is a bleed valve 45 in the bulb which allows air in the cuff to bleed out at a rate of several mm Hg per second, the actual bleed rate depending upon the cuff pressure. Tubing 47 connects the cuff to a manifold within the instrument housing. The overall cuff arrangement is standard except that the take-off tubing 47 is extended to the instrument rather than to a mercury column as in conventional blood pressure measuring instruments.

The instrument itself includes three switches and a twelve-character display DP1 (under a red translucent strip 43). Switch S1 (on the top) is the main on/off switch which, when operated, connects the internal batteries to the circuit. (The unit also includes a jack 49 for insertion of the plug of a charging circuit when it is necessary to recharge the batteries.) Switch S2 is the reset/exhaust switch which is spring-loaded to an open position. When it is momentarily closed, as will be described below, the instrument resets and initiates a new cycle of operation. Switch S3, another normally-open, spring-loaded push-button, is the recall/cuff control. When it is operated, one of two different sequences takes place depending upon the state of the instrument at the time the button is operated. Toward the beginning of the overall cycle, operation of switch S3 closes take-off tubing 47 as will be described shortly, so that the pressure in the cuff can be pumped up by repeatedly squeezing bulb 44. At the end of a measurement cycle, the final values are displayed for only ten seconds, also as will be described below, and the display is then blanked to conserve power. Operation of switch S3 causes the previously determined values to be displayed once again, for another ten seconds.

The display itself consists of 12 character positions, each of which has seven light-emitting diode segments as shown at the left of FIG. 9. Depending upon which of the segments are energized, any one of 15 characters can be displayed at each position, the 15 characters also being shown in FIG. 9 and it being obvious which of the seven segments are used to form each of the fifteen characters. A blank may be displayed simply by energizing no segments. The display elements are also used to form numerals as is well known in the art.

The instrument also includes a light-emitting diode LD1 (under a red translucent area 51 on the case) which, when illuminated, represents one of two things. First, the light is on whenever the system is in the process of detecting a blood pressure pulse (a rise in the occluding cuff pressure). Second, after the final display has been blanked in order to conserve power, the light is turned on to indicate to the operator that the display can be recalled if switch S3 is momentarily operated. Lastly, the positions on the display of the final measurement values are printed on the case.

FIG. 2 depicts just one part of the circuit board 18 on which the circuit components are mounted within the housing. Switch S3 can be seen in the drawing. In addition, a manifold 20 is mounted on the board, and spaced from it by spacer 22. The manifold provides open communication between input pipe 24 (on which take-off tubing 47 of FIG. 1 is placed), a pipe segment 26, and a valve V1. The valve is normally open, but when its two leads (not shown) have a potential applied across them, the valve closes. A pressure transducer T1 is mounted on the other side of the board—the side on which all of the chips used in the circuit are mounted—and the input port of the transducer is connected to pipe segment 26. It is apparent that since pipe 24 is connected via take-off tubing 47 to the cuff, transducer T1 has as its "input" the cuff pressure. Valve V1 is used to open the cuff to the atmosphere, within and through the housing, so that the cuff pressure can rapidly decrease at the end of a measurement cycle. The valve is closed automatically by the circuit after switch S3 is operated so that the pump-up procedure can commence. It is important to note that transducer T1 is located within the instrument housing and is not positioned in the cuff (although it could be). Thus there are no circuit elements which are in contact with the patient.

The schematic of the circuit is shown in FIGS. 3–6. Many of the chips are identified on the schematic, and the omitted chip identifications, as well as the component values, are as follows (many of the resistors are contained in four resistor networks, identified by the symbols RA1–RA4, which will be discussed below):

| | | | | |
|---|---|---|---|---|
| C1 | 22uf | C8 | .01uf | |
| C2 | .01uf | C9 | 22uf | |
| C3 | 6.8uf | C10 | .01uf | |
| C4 | 6.8uf | C11 | .47uf | |
| C5 | .01uf | C12 | .01uf | |
| C6 | .47uf | C13 | .47uf | |
| C7 | .01uf | C14 | .01uf | |
| C15 | 10f | R19 | 10K | |
| C16 | 22uf | R20 | 2K | |
| C17 | .47uf | R21* | 20K | (RA1) |
| C19 | 1uf | R22 | 1K | |
| C20 | 1uf | R23* | 5K | (RA2) |
| C21 | .01uf | R24 | 100 | |
| C22 | 270pf | R25* | 10K | (RA1) |
| C23 | 68pf | R26 | 100 | |

-continued

| | | | | | |
|---|---|---|---|---|---|
| C24 | 20pf | | R27* | 7.5K | (RA1) |
| C25 | 20pf | | R28* | 402K | (RA1) |
| C26 | .1uf | | R29* | 10K | (RA1) |
| C27 | .1uf | | R30* | 330 | (RA4) |
| R1* | 18.7K | (RA2) | R31* | 10K | (RA1) |
| R2* | 19.6K | (RA2) | R32* | 330 | (RA4) |
| R3* | 1M | (RA2) | R33* | 330 | (RA4) |
| R4* | 10K | (RA2) | R34* | 330 | (RA4) |
| R5* | 18.7K | (RA2) | R35* | 162K | (RA1) |
| R6* | 1M | (RA2) | R36* | 40.2K | (RA1) |
| R7* | 10K | (RA2) | R37* | 4.7K | (RA3) |
| R8* | 21.5K | (RA2) | R38* | 4.7K | (RA3) |
| R9 | 1K | | R39* | 4.7K | (RA3) |
| R10* | 20K | (RA2) | R40* | 4.7K | (RA3) |
| R11* | 100K | (RA2) | R41 | 47 | (½W) |
| R12* | 20K | (RA2) | RA1 | Custom 16-Pin Dip, 1 | |
| R13* | 5.6K | (RA1) | RA2 | Custom 16-Pin Dip, 1 | |
| R14* | 100K | (RA2) | RA3 | Bourns 4310R-102-47 (10-Pin Sip), 1% | |
| R15* | 330 | (RA4) | RA4 | Bourns 4310R-102-33 (10-Pin Sip), 1% | |
| R16* | 20K | (RA1) | | | |
| R17* | 4.7K | (RA3) | D1 | IN4001 | |
| R18* | 15K | (RA1) | D2 | IN4001 | |
| D6 | IN4001 | | ID1 | RL209-2 | |
| Z1 | IN5523 | | V1 | Angar Scientific Controls, Model 336073 (East Hanover, New Jersey) | |
| IC3 | LM324 | | | | |
| IC10 | LM393N | | | | |
| IC11 | DS88L12N | | DP1 | NSA7120 | |

Figure 3:
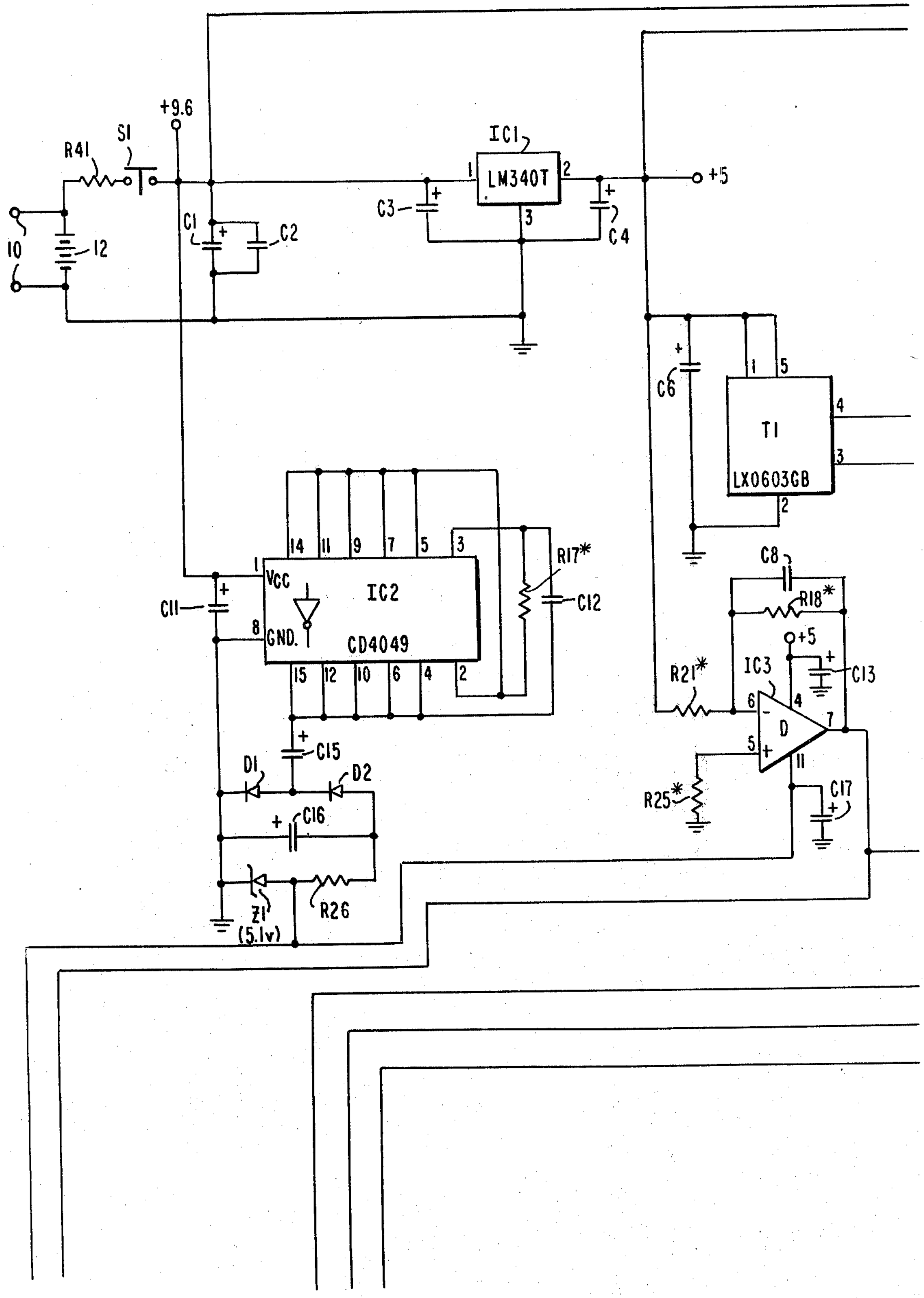

In FIG. 3, the numeral 12 depicts eight 1.4-volt batteries. Although each battery has a nominal voltage of 1.4 volts, the system is designed to operate even if the overall voltage falls as low as 9.4 volts. Terminals 10 simply depict the points at which a charging circuit may be connected to the instrument to recharge the batteries. When switch S1 is closed, power is furnished to the circuit. A potential of 9.6 volts is shown to the right of switch S1, since this is a typical actual potential in normal use. Chip IC1 is a voltage regulator which derives a 5-volt regulated potential at its output pin 2. The circuitry directly below switch S1 and chip IC1 is a standard circuit for deriving a −5.1-volt potential at the junction of Zener diode Z1 and resistor R26. This negative potential is required for proper operation of chip IC4. Chip IC2 is arranged as a 10-kHz oscillator. The configuration is standard, and five of the six inverters on the chip are connected in parallel to lower the output impedance so that charge can be dumped faster into capacitor C16. The circuit is shown on page 1-50 of the "Data Conversion Design Manual" published by Teledyne Semiconductor, 1979.

Transducer T1 on FIG. 3 is a National Semiconductor chip—a pressure transducer utilizing a piezoresistive circuit which derives an output voltage across pins 3 and 4 which is proportional to applied pressure. It is the pressure port of the transducer (not shown in FIG. 3) which is coupled to pipe segment 26 in FIG. 2. Amplifier D of chip IC3 on FIG. 3, and the associated components, are used to develop a −3.75-volt reference voltage which is applied through resistor R27 (FIG. 4) to the positive input of amplifier A of chip IC3.

At this point, two things should be noted. First, many of the resistors are marked in the schematic with asterisks. These asterisks identify the resistors as being included in one of four resistor networks, as will be described below in connection with FIG. 8. The second point to note is that no invention is claimed in the various sub-systems per se of the overall circuit. Thus, with reference to FIG. 3, the derivation of the +5 and −5.1-volt power supplies, as well as the −3.75-volt potential, and the connections to the pressure transducer T1, are all known in the art. The invention resides in the manner in which the subsystems are interconnected to allow the system to sequence in the manner to be described below.

Figure 4:
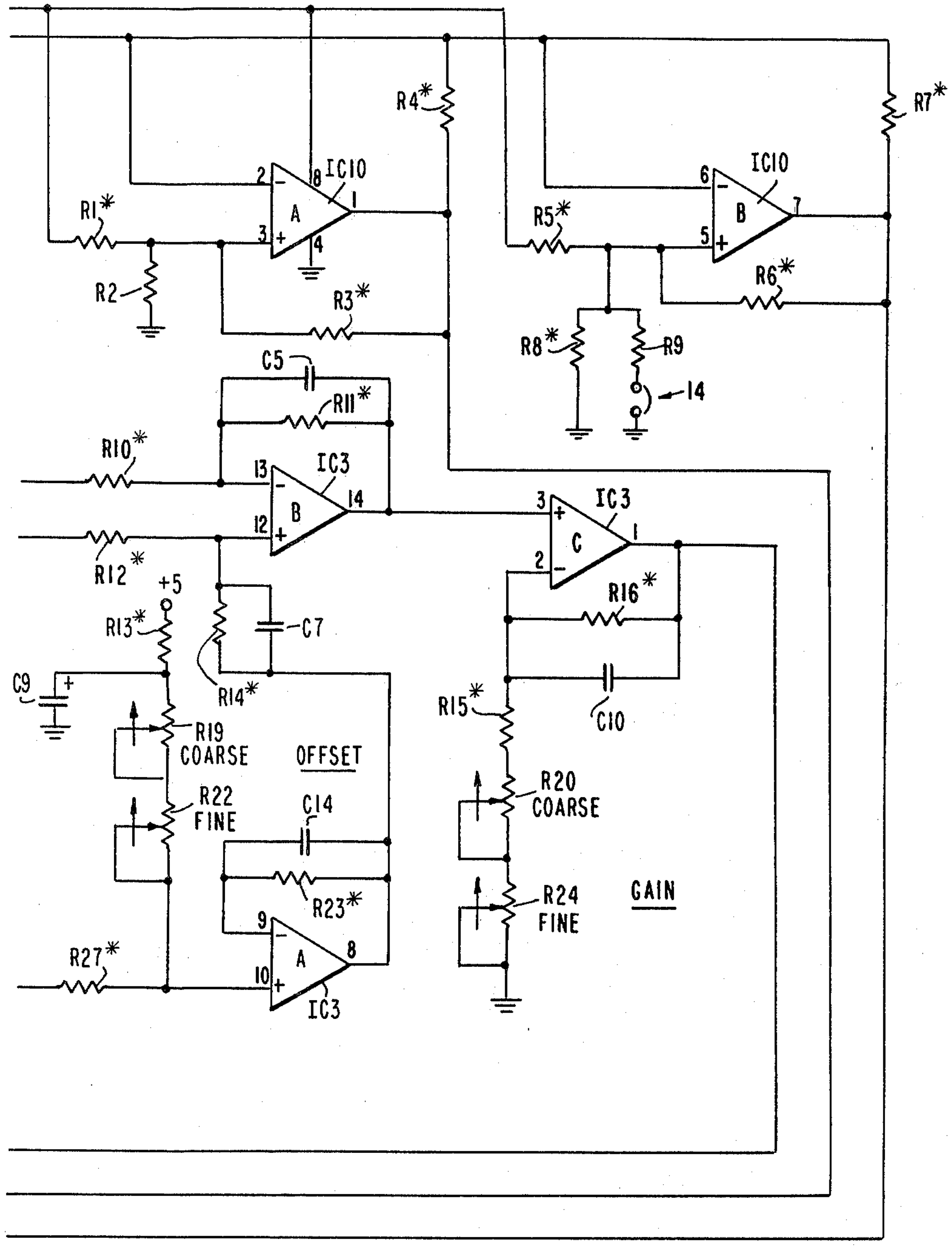

The ambient output of transducer T1 may range between +50-mv and −50-mv. The analog-to-digital converter chip IC4 (FIG. 5) works on positive inputs only, and thus an offset is introduced by amplifier A of chip IC3 (FIG. 4). The amplifier itself is used in a unity gain configuration, and the coarse and fine potentiometer controls R19 and R22 are used to provide an ambient potential difference across pins 12 and 13 of differential amplifier B of chip IC3 which is in the 30-mv to 50-mv range. The output at pin 14 of amplifier B of chip IC3 is extended to the positive input of amplifier C of the same chip. This is the gain amplifier which is provided with coarse and fine potentiometer controls R20 and R24. The potential at pin 1 of chip IC3 is extended to the analog input at pin 14 of chip IC4, the analog-to-digital converter. It is this chip, on FIG. 5, which derives samples of the instantaneous cuff pressure, as reflected by the analog output at pin 1 of chip IC3.

The ambient output when the cuff pressure is open to the atmosphere need not be precise. In fact, it varies with temperature and atmospheric pressure. The system self-calibrates itself by deriving a reference pressure at the output of the analog-to-digital converter when the cuff is at atmospheric pressure. Thus at the start of any measurement cycle, the analog signal furnished to the converter is non-zero, but this is of no moment because the system subtracts the reference pressure from each actual sample taken. Thus all sample values which are processed by the apparatus are pressures which are relative to atmospheric pressure.

In the factory, however, the offset and gain potentiometers are adjusted to provide accurate readings. Tubing 42 in FIG. 1 is connected to a pump-up bulb without a bleed hole and to an accurate mercury manometer. If the cuff is initially at atmospheric pressure, the instrument should read a pressure of zero, since each sample, less the reference atmospheric pressure, should provide a value of zero. During the factory-calibrate mode, the instrument actually displays the cuff pressure as will be described below. The operator manipulates the two offset potentiometers until a pressure reading of zero is obtained. Thereafter, the bulb is pumped up. Since a bleed hole is not provided in the bulb, the pressure in the cuff remains constant at the pumped-up value. The instrument may display a pressure value which is different from the actual value as represented on the manometer. The two gain potentiometers are adjusted until the pressure reading (relative to the reference pressure) displayed by the instrument is correct. By thus manipulating both pairs of potentiometers, the instrument can be calibrated in the factory. Thereafter, it is the use of the reference pressure subtraction technique which insures that all displayed pressures are pressures which are relative to atmospheric pressure, so that temperature and altitude considerations are of little importance.

Comparators A and B of chip IC10 on FIG. 4 serve to develop two test signals. The output of comparator A is high whenever the battery potential, connected to the positive input, is greater than 9.8 volts. The output of comparator B is high whenever the battery potential exceeds 9.4 volts. The two signals at the outputs of the comparators are used in two different ways.

During normal processing, as will be described below, the "test" signals at the outputs of the two comparators are used to inform the system of the state of the battery. If both test signals are high, indicating a battery potential greater than 9.8 volts, the system provides no "state-of-the-battery" message to the operator. But if the output of amplifier B is high and the output of amplifier A is low, it is an indication that the battery potential exceeds 9.4 volts but does exceed 9.8 volts. In such a case, the instrument is capable of performing up to 25 more measurements so it continues to function. However, the operator is provided with a message indicating that the batteries should be recharged. If both test signals are low, the system will not allow measurements to be taken, and a message is displayed which informs the operator that the batteries must be recharged before the instrument can be used.

It will be noted that pin 5 of chip IC10 is connected through resistor R8 (21.5k) to ground. Resistor R9 (1k) is in parallel with it, but this resistor is left floating. In the factory, a test clip, symbolized by the numeral 14, can be used to ground the lower end of resistor R9. By so doing, the output of comparator B is forced low. A factory technician does this when the unit is to be calibrated.

The system includes a microprocessor and firmware for controlling its cycling. (The Intel 8048 chip which is used includes the firmware together with the microprocessor on the same chip, although other microprocessors with separate ROM chips can be employed.) The firmware includes instructions for cycling the system in the factory-calibrate mode; these instructions are not actually accessed during normal use of the instrument, and control cycling of the machine only in the factory-calibrate mode. During the factory-calibrate procedure, all the system does is to measure cuff pressure and to display it so that the operator may manipulate the potentiometer controls. The instructions for cycling in the factory-calibrate mode are included in the firmware which is shipped in the unit despite the fact that, after factory calibration, this part of the firmware is not used (unless re-calibration is ever required, in which case the unit may be thought of as being calibrated in the "factory"). The system therefore must have a way of knowing whether it is to cycle in the normal mode or in the factory-calibrate mode. It is jumper 14 which does this.

When a unit is being calibrated in the factory, fresh batteries are in it and thus the output of comparator A of chip IC10 is high, indicating that the battery potential is above 9.8 volts. But when resistor R9 is connected to ground by the jumper, the output of comparator B of chip IC10 is forced low, indicating that the battery potential is below 9.4 volts. The two test conditions are thus inconsistent with each other, since they indicate battery potentials which are both above and below an intermediate level. When the system detects these inconsistent test conditions, it branches to the factory-calibrate mode of operation.

The advantage of this technique is that it allows a branch to be controlled in the firmware without the need for another test input to the microprocessor. As will become apparent below, all of the pins of the 8048 microprocessor are utilized, and there is no available pin which can be used as a separate test input. Were such a pin available, it would be relatively simple to apply an appropriate potential to it in the factory which would cause a branch to the factory-calibrate mode of operation. But in the absence of an available pin, it would appear that there is no way for the microprocessor to test whether it should branch to the factory-calibrate mode of operation. But since two battery test signals are required anyway, an effective state test can be controlled by forcing the two battery test signals to represent inconsistent conditions. Such inconsistent signals never arise during the normal mode of operation, since the battery potential can never be both above and below an intermediate level.

Figure 5:
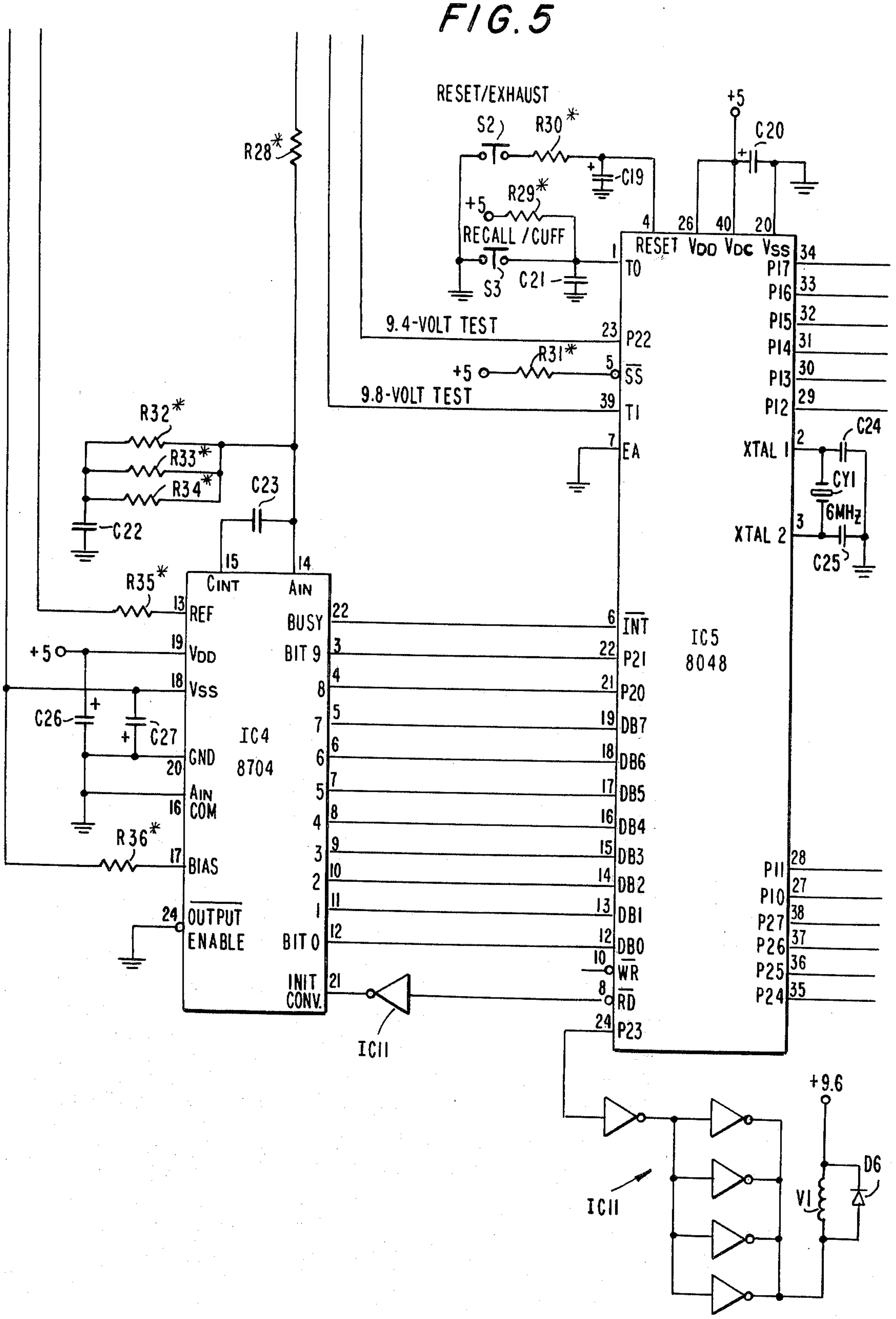

On FIG. 5, chip IC4 is a Teledyne 8704 analog-to-digital converter, arranged in a standard configuration. The chip is interfaced directly to chip IC5, an Intel 8048 microprocessor with on-board ROM and RAM. The analog signal which is to be converted to a digital sample appears at pin 14 of chip IC4. The converter generates a 10-bit sample at pins 3-12. The data bus of the microprocessor has only 8 lines, DB0-DB7, and consequently only the eight least significant bits of each sample are connected to the data bus inputs of the microprocessor. The two most significant bits, 8 and 9, are extended to the bit 0 and bit 1 inputs of port 2 of the microprocessor, pins 21 and 22. The microprocessor reads in one sample at the same time that it initiates the formation of a new one, i.e., at the same time that it initiates a new conversion cycle. During normal processing, the microprocessor is so fast that it is ready for another sample even before the converter has one available. During the course of a conversion, the BUSY output of the converter is high. This output is connected to the INT input of the microprocessor, and the microprocessor polls this input, remaining in a wait loop, until the BUSY signal eventually goes low at the end of a conversion cycle. At this time, a new sample appears at the outputs of the converter, and the microprocessor initiates the reading in of the new sample by reading in the bit values at port 2 (the two most significant bits of the new sample appear at the bit 0 and 1 positions of the port). The microprocessor then reads in the eight remaining bits in the new sample (which remain available at the output pins of the converter until the next conversion is over), by reading in the eight bits which appear at the DB0-DB7 data bus pins. The read instruction which is executed results in the RD output (pin 8) of the microprocessor going low. One of the inverters in chip IC11 inverts this low signal and applies a high potential to the "initiate conversion" input of the converter. This causes the converter to take a new sample, and its BUSY output goes high. Thereafter, the microprocessor proceeds with its processing of the new sample until it is ready to read in a new sample. The 8048 chip polls the INT input, which is high as long as a conversion cycle is in progress, and the microprocessor remains in a wait loop. Only when a new sample is available at the 10 output pins of the converter does the BUSY signal go low and the microprocessor actually read in a new sample.

The sampling rate is thus dependent upon how fast the converter can generate samples. In the illustrative embodiment of the invention, samples are generated approximately every 2.5 milliseconds. This is a sufficiently high sampling rate; if a typical blood pressure pulse has a duration of 100 milliseconds, about 40 samples will be taken during its course—more than enough to completely define the pulse waveshape.

The methodology of my invention is not applicable only to microprocessor-based systems. In fact, my above-identified application Ser. No. 000,499 discloses a similar methodology in a system which does not utilize a microprocessor. Nevertheless, the preferred embodiment of the invention does incorporate a microprocessor, among other reasons because of the reduced manufacturing costs which are made possible thereby. For a complete understanding of my invention, it must be appreciated how the microprocessor is interfaced to the other components in the circuit. Despite the fact that the interface to the analog-to-digital converter has already been described, it will be helpful before describing the other interfaces to the microprocessor to discuss the chip itself. Only a brief description of the 8048 microprocessor will be given in view of its widespread use in industry. A complete description of the unit may be found in the 1979 Intel Corporation Publication entitled "MCS-48 Family of Single Chip Microcomputers User's Manual".

It should be noted that the unit is actually referred to by its manufacturer as a microcomputer, not a microprocessor. This is due to the fact that it includes on-board memory—1k of program memory (ROM) and 64 data memory locations (RAM). All memory locations have 8 bits.

The 64 locations of the data memory are indirectly addressable through either of two RAM pointer registers at addresses 0 and 1—registers R0 and R1. The first eight locations 0-7 of the data memory are designated as working registers, and are directly addressable by several of the instructions which the chip can execute. When the Register Bank Switch instruction is executed, data memory locations 34-41 become the working registers instead of locations 0-7. It is only these registers which are then directly addressable. When the second register bank is selected as the working registers, the registers at addresses 24 and 25, R0' and R1', can be used as pointer registers.

RAM locations 8-23 serve in a dual capacity—they cannot only be used for any purpose desired, but they also serve as the program counter stack; they are addressed by the stack pointer during subroutine calls and returns as well as by pointer registers R0, R1, R0' and R1'. When the system is reset by applying a low potential to pin 4 of the chip, the program counter is reset to zero so that the first instruction which is fetched is that from location 0 in the program memory. In addition, the stack pointer (a 3-bit register in the Program Status Word) is initialized to zero, and points to RAM locations 8 and 9. Each subroutine call or interrupt results in the program counter contents (12 bits) and 4 bits of the Program Status Word being transferred to the two locations pointed to by the stack pointer, and the stack pointer is then incremented so that it points to the next two locations (10 and 11, following 8 and 9). A return from subroutine or interrupt processing results in decrementing of the stack pointer and then restoration to the program counter and the Program Status Word of the two previously stored bytes.

The 8048 has two 8-bit ports, P1 and P2. In FIG. 5, a pin label such as P26 identifies the sixth bit of port 2. Data written to a port is latched and remains unchanged until re-written. But even though the ports latch on output, they can also be used as non-latching inputs. In this sense, the ports are quasi-directional. This feature is used to advantage in the illustrative embodiment of the invention because the microprocessor need not utilize the data memory to store information which is actually latched at the two output ports; if the microprocessor requires this information, it can simply read it in. Thus the ports serve not only as inputs and outputs, but in a sense they also serve as memory.

The BUS is an eight-bit port (DB0–DB7) which is a true bi-directional port which can be strobed for input and output. Data are written and latched by using the OUTL instruction, and are inputted by using the INS instruction. It is when the INS instruction is executed that the $\overline{RD}$ output is pulsed low. It will be recalled from the description above the interface between the analog-to-digital converter and the microprocessor that the reading in of the eight least significant bits of a sample (the second step of the overall reading in of a sample) is accompanied by the pulsing of the $\overline{RD}$ output of the microprocessor and the initiation of a new conversion cycle.

There are three pins which serve as inputs and are testable with conditional jump instructions. The three pins are T0, T1 and $\overline{INT}$. The $\overline{INT}$ input can also control interrupts when it goes low, provided that interrupts are enabled under program control; they are not thus enabled in the illustrative embodiment of the invention, and the $\overline{INT}$ input is simply used as are the T0 and T1 inputs.

The processor includes two flags F0 and F1. These flags may be set under program control, and then tested to control branches.

The chip also includes a timer/counter, which functions as a timer in the illustrative embodiment of the invention. Separate instructions enable the timer/counter and start automatic incrementing of a count under timer control. In the illustrative embodiment of the invention, the counter is initialized such that the counter overflows every 800 microseconds. Overflow of the counter controls an automatic jump to location 7 in the program memory. In the system of FIGS. 3–6, the timer/counter is used to time 800-microsecond intervals; a single character position of the display is updated or refreshed every 800 microseconds, the entire display being changed or refreshed every 9.6 milliseconds.

The 8048 chip is provided with a self-contained clock, which requires a crystal between pins 2 and 3. A 6-MHz crystal is used in the illustrative embodiment of the invention, this being the recommended crystal frequency.

Referring to FIG. 5, there will now be described only those pin connections whose understanding will be necessary in the following detailed description. Switch S2 is the reset switch and is coupled through resistor R30 to the reset input, pin 4, of chip IC5. When the reset button is depressed, the microprocessor is reset and the program counter is loaded with a value of zero. The recall/cuff switch S3 similarly applies a ground potential to test input T0, pin 1, when it is depressed to control one of two different operations depending upon the state of the system when the switch is operated, as described above.

The 9.8-volt test line is connected to the T1 test input. When this input is tested, a high level (1) indicates that the battery potential exceeds 9.8 volts, and a low level (0) indicates that it does not. The 9.4-volt test line is connected to pin 23, bit 2 of port 2. When port 2 is read and bit 2 is examined, the system can determine whether the battery potential is greater or less than 9.4 volts.

As described above, the BUSY output of chip IC4 is used as the $\overline{INT}$ test input of chip IC5. The microprocessor remains in a wait loop until the BUSY output of the converter goes low, indicating that a new sample is available. When the microprocessor first reads in port 2, the two bit values at bit 0 and 1 represent the two most significant bits of the latest sample. Thereafter, the eight BUS inputs are read in to determine the eight least significant bits, and the pulsing low of the $\overline{RD}$ output of the microprocessor initiates a new conversion cycle.

Pin 24 is the bit 3 pin of port 2. As long as this pin is high in potential, five of the inverters of chip IC11 apply a high potential to the lower end of the energizing coil of normally-open valve V1. As a result, no current flows through the coil and the valve remains open. But a low potential at bit 3 of port 2 causes a low potential to be applied to one end of the energizing coil, current flows through it, and the valve closes. When the system is initialized upon reset, all of the port outputs are forced high, and thus initially the valve is open to vent the cuff to the atmosphere. It should be noted that four inverters are connected in parallel at the bottm of FIG. 5 in order to provide a sufficient sink for the current which closes the valve.

Bits 4–7 of port 2 (pins 35–38) are used to identify one of the twelve positions of the display. The microprocessor selects a position for up-dating or refreshing by applying an appropriate 4-bit code to pins 35–38. (Of the 16 possible codes, the microprocessor applies only 12 in sequence since the display has only 12 character positions.) The bit outputs are inverted by respective inverters in chip IC7, and the inverted bit values are applied to pins 12–15 of chip IC9 on FIG. 6. This latter chip energizes one of its 12 outputs depending upon the four-bit code outputted at bits 4–7 of port 2. Display element DP1 has 12 seven-segment displays (see FIG. 9) and, in order to energize selected segments at any particular position, it is necessary to energize the cathode at that position. Decoder chip IC9 controls the energization of only one cathode at any given time.

The particular anode segments which are selected to be illuminated are represented by the seven least significant bits of port 1, at pins 27–33. Each of these bits is inverted by an inverter in either chip IC6 or chip IC7, and the seven inverted segment bits are applied to inputs of respective amplifiers in chip IC8. The most significant bit at port 1 determines whether the pulse light LD1 is to be illuminated. The bit at pin 34 of the microprocessor is similarly inverted in chip IC6 and is amplified by one of the inverters in chip IC8. Of the eight outputs of chip IC8, seven are extended to display DP1 for controlling selected energizations of the seven segments at the position determined by decoder IC9. The eighth output of chip IC8 is extended to the anode of the pulse light LD1 for controlling its illumination during either the presence of a pulse, or after final measurement results have been displayed for ten seconds and the display has been blanked.

Figure 8:
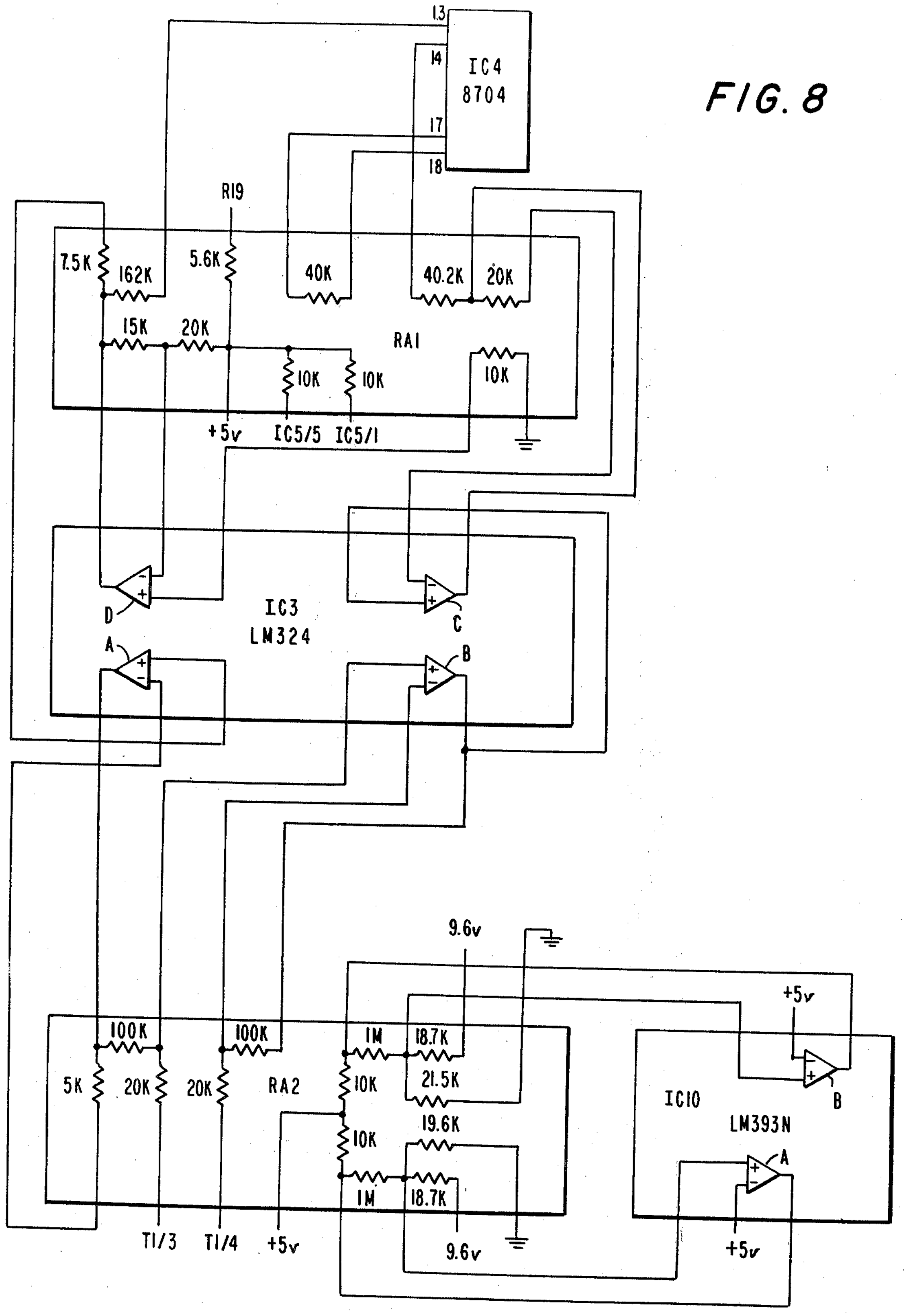
FIG. 8 depicts two resistor networks utilized in the circuit of FIGS. 3-6.

All of the resistors which are marked with asterisks in FIGS. 3–6 are included on resistor networks and have a precision of 1%. The list of component values above identifies the resistors included in each of networks RA1–RA4. As indicated at the end of the component list, network RA3 is a standard ten-pin, single-in-line package; it has five resistors each of magnitude 330 ohms. Network RA3 is a similar package having five 4.7k resistors. Networks RA1 and RA2 are both custom 16-pin, dual-in-line packages. FIG. 8 depicts the network configuration for both RA1 and RA3, and the manner in which the internal resistors are connected to certain of the other chips. It should be noted that although network RA1 is provided with 16 pins, only fifteen of them are used. A spare resistor may be fabricated on the chip if required, e.g., another 10k resistor may be connected in parallel with the two which are connected to pins 1 and 5 of chip IC5.

Throughout the remaining description, reference is made to the firmware source statements. The listing was generated using the Intel INTELLEC microcomputer development system, utilizing the macro assembler identified at the top of the listing. The source statements themselves are in the center, and each statement is numbered consecutively. In the rightmost column there are comments which will be helpful in understanding the firmware, although all statements are described below. The two leftmost columns provide the assembled object code and the ROM location of each byte. The listing thus presents the complete ROM code for the microprocessor chip. For an understanding of the invention, however, it is necessary to analyze the source statements. The assembly listing consists of 19 pages, as follows:

```
ASM48 :F1:BP9.SRC TITLE ('ESM-410 BP9.LST REV 0 06/12/79 PROM 43')

ISIS-II MCS-48/UPI-41 MACRO ASSEMBLER, V2.0
ESM-410 BP9.LST REV 0 06/12/79 PROM 43

 LOC  OBJ        SEQ        SOURCE STATEMENT

                   1 $      DEBUG MACROFILE PAGEWIDTH (80)
                   2
                   3 ; BLOOD PRESSURE MACHINE PROGRAM
                   4 ;        ESM 400 SERIES
                   5 ;        COPYRIGHT 1979- MEDTEK CORPORATION
                   6
                   7 ; PULSE AMPLITUDE TESTING ASSIGNMENTS
                   8
 00FF              9 TRUE     EQU     0FFH
 0000             10 FALSE    EQU     00
 0000             11 TEST     EQU     FALSE
                  12
                  13 ; BANK 0 ASSIGNMENTS
                  14
                  15 ; R0 AND R1 USED AS GENERAL POINTERS
                  16
 0002             17 HTS      EQU     R2
 0003             18 HMAX     EQU     R3          ; MAXIMUM HEIGHT
 0004             19 PLSCNT   EQU     R4          ; PULSE COUNT
 0005             20 COUNT    EQU     R5          ; COUNTER
 0006             21 PLSVLD   EQU     R6          ; VALID PULSE COUNT
 0007             22 TENSEC   EQU     R7          ; TEN SECONDS UP
                  23
                  24 ; BANK 1 ASSIGNMENTS
                  25
                  26 ; R2,R3 USED FOR REFERENCE PRESSURE
                  27
 0000             28 SEGPTR   EQU     R0          ; CHAR SEGMENT POINTER
 0001             29 DIGSAV   EQU     R1          ; DIGIT # SAVE
 0004             30 AUX3     EQU     R4          ; PLS MSEC COUNTER
 0005             31 AUX1     EQU     R5          ; MSEC COUNTER
 0006             32 AUX2     EQU     R6          ; SEC COUNTER
 0007             33 ASAV     EQU     R7          ; SAVE ACC HERE
                  34
                  35 ; MEMORY STORAGE
                  36
 0018             37          ORG     18H
                  38
 0001             39 SGPTR    DS      1           ; ALT REF TO SEGPTR
 0001             40          DS      1           ; DIGIT # SAVE
 0002             41 PREF     DS      2           ; REFERENCE PRESSURE
 0001             42 AUX33    DS      1           ; ALT REF TO AUX3
 0001             43 AUX11    DS      1           ; ALTERNATE REF TO AU
 0001             44 AUX22    DS      1           ; ALTERNATE REF TO AUX.
                  45
 0020             46          ORG     20H
                  47
 0002             48 SYS      DS      2           ; SYSTOLIC PRESSURE
 0002             49 DIA      DS      2           ; DIASTOLIC PRESSURE
 0002             50 TEMP     DS      2           ; TEMP PRESS STORAGE
 0002             51 BCDN     DS      2           ; BCD NUMBER
 0004             52 HTB      DS      4           ; PULSE HEIGHT
```

```
LOC  OBJ          SEQ        SOURCE STATEMENT

002B               53 HP      EQU     HTBL+3          ; LAST PULSE HEIGHT
0008               54 PTBL:   DS      8               ; PRESSURES
0032               55 PLAST   EQU     PTBL+6          ; LAST PRESS BEFORE PLS
000C               56 DTBL:   DS      12              ; SEGMENT TABLE
                   57
0028               58 H1      EQU     HTBL
0029               59 H2      EQU     HTBL+1
002A               60 H3      EQU     HTBL+2
002B               61 H4      EQU     HTBL+3
                   62
002C               63 PR1     EQU     PTBL
002E               64 PR2     EQU     PTBL+2
0030               65 PR3     EQU     PTBL+4
0032               66 PR4     EQU     PTBL+6
002C               67 PMAX    EQU     PTBL
002E               68 PMIN    EQU     PTBL+2
                   69
                   70 ; SET BEGINNING OF PAGE 3 FOR MESSAGES
                   71
0300               72 PG3     EQU     300H
                   73
                   74 ; START OF PROGRAM
                   75
0000               76         ORG     0
                   77
0000 23F6          78 START:  MOV     A, -#10         ; INITIALIZE TIMER
0002 62            79         MOV     T, A
0003 B818          80         MOV     R0, #SGPTR      ; INIT DISPLAY SEG PTR
0005 041E          81         JMP     SEGSET
                   82
                   83 ; TIMER INTERRUPT SUBROUTINE
                   84
0007               85         ORG     7
                   86
0007 D5            87 TIMER:  SEL     RB1             ; REGISTER BANK 1
0008 AF            88         MOV     ASAV, A         ; SAVE ACCUMULATOR
0009 23F6          89         MOV     A, -#10         ; 800 USEC TIMER
000B 62            90         MOV     T, A
000C 5442          91         CALL    SEGS            ; NEXT CHARACTER
000E FC            92         MOV     A, AUX3         ; PLS WIDTH TIMER
000F C612          93         JZ      MCHK
0011 CC            94         DEC     AUX3
0012 ED1A          95 MCHK:   DJNZ    AUX1, TIMINT    ; DEC MSEC COUNTER
0014 BD7D          96         MOV     AUX1, #125      ; 100 MSEC
0016 FE            97         MOV     A, AUX2         ; SEC COUNTER
0017 C61A          98         JZ      TIMINT          ; TIME ELAPSED?
0019 CE            99         DEC     AUX2            ; NO, DEC AUX2
001A 161C         100 TIMINT: JTF     TEXIT           ; RESET TIMER OVERFLOW
001C FF           101 TEXIT:  MOV     A, ASAV         ; RESTORE ACCUMULATOR
001D 93           102         RETR
                  103
                  104 ; MACROS
                  105
                  106 ; COMPARE TWO SINGLE BYTE QUANTITIES
                  107
```

```
LOC  OBJ        SEQ       SOURCE STATEMENT

                108 CMPH     MACRO    HX, HY
                109          MOV      R0, #HX
                110          MOV      R1, #HY
                111          CALL     MINV
                112          ENDM
                113
                114 ; INITIALIZE DISPLAY AND TIMER
                115
001E B034       116 SEGSET:  MOV      @R0, #DTBL
0020 232B       117          MOV      A, #CAL-PG3      ; "CAL"
0022 5408       118          CALL     DALPHA
0024 25         119          EN       TCNTI
0025 55         120          STRT     T                ; START TIMER
                121
                122 ; DELAY 1 SEC, GET REFERENCE PRESSURE
                123
0026 54F0       124          CALL     WT1SEC
0028 08         125          INS      A, BUS           ; INITIAL INIT CONV
0029 74F5       126 AMBCHK:  CALL     REFP             ; REF PRESS
                127
                128 ; CALIBRATE MODE AND BATTERY CHECK
                129
002B 0A         130 R40:     IN       A, P2            ; CHECK CAL SWITCH
002C 524A       131          JB2      DELCHK           ; BATT OK, NOT CAL
002E 464A       132          JNT1     DELCHK           ; BRANCH IF BATT LOW
0030 9AF7       133          ANL      P2, #0F7H        ; CLOSE VALVE
                134
                135 ; FACTORY CALIBRATE MODE
                136
0032 5406       137 CALIB:   CALL     DPRESS           ; "PRESS"
0034 B97C       138 CALMIN:  MOV      R1, #DTBL+8      ; PUT "-" HERE
0036 B1BF       139          MOV      @R1, #0BFH       ; "-" SEGMENTS
0038 34FA       140 CALCON:  CALL     READP            ; READ PRESSURE
003A 85         141          CLR      F0
003B F644       142          JC       CALPOS           ; PRESSURE NEG?
003D 95         143          CPL      F0
003E 547E       144          CALL     DADDC            ; - 2X PRESS
0040 5476       145          CALL     DMINC            ; -PRESS + 2X PRESS
0042 54E9       146          CALL     DS1              ; PTMP
0044 5410       147 CALPOS:  CALL     DSPRES           ; DISPLAY PRESSURE
0046 B634       148          JF0      CALMIN
0048 0438       149          JMP      CALCON
                150
                151 ; CHECK IF DELTA PRESSURE > 1.0 MM HG
                152
004A 54CA       153 DELCHK:  CALL     BDFAD            ; BATTERY DEAD?
004C 54F0       154          CALL     WT1SEC           ; WAIT 1 SEC
004E 34FA       155          CALL     READP
0050 B972       156          MOV      R1, #PLAST       ; SAVE LAST PRESS RDG
0052 74FC       157          CALL     DMOVE
0054 34FA       158          CALL     READP
0056 B932       159          MOV      R1, #PLAST
0058 5470       160          CALL     DMINV            ; PTMP - PLAST
005A F65E       161          JC       DELTA            ; BRANCH IF DELTA >=0
005C 37         162          CPL      A                ; 2'S COMP IF NEG
```

```
LOC   OBJ         SEQ         SOURCE STATEMENT

005D  17          163               INC      A
005E  03FE        164  DELTA:       ADD      A, #-1+2           ; DELTA P : 1.0 MM HG
0060  F629        165               JC       AMBCHK             ; BRANCH IF >= 1 MM HG
                  166
                  167  ; CHECK IF BATTERY LOW OR OK; IF BATTERY LOW,
                  168  ; MESSAGE IS "LO DC", ELSE "CUFF"
                  169
0062  232F        170               MOV      A, #CUFF-PG3       ; "CUFF"
0064  5668        171               JT1      MCUFF              ; BRANCH IF BATT OK
0066  233A        172               MOV      A, #LOBATT-PG3     ; "LO DC"
0068  5408        173  MCUFF:       CALL     DALPHA
                  174
                  175  ; CHECK IF PUMPING BEFORE RECALL/CUFF DEPRESSED
                  176
006A  54CA        177  LOOP:        CALL     BDEAD              ; CHECK BATTERY
006C  34FA        178               CALL     READP              ; GET PRESSURE
006E  E67E        179               JNC      CLOSE              ; PRESS NEG?
0070  2214        180               MOV      A, #10+2           ; PRESS > 10 MM HG
0072  BA00        181               MOV      REX, #0H
0074  5476        182               CALL     DMINC
0076  E67E        183               JNC      CLOSE              ; BRANCH IF < 10 MM HG
0078  232F        184  LOOP1:       MOV      A, #CUFF-PG3
007A  54C0        185               CALL     BLINK
007C  0478        186               JMP      LOOP1
007E  366A        187  CLOSE:       JT0      LOOP               ; RECALL/CUFF?
0080  74F5        188               CALL     REFP               ; NEW REF PRESS
0082  9AF7        189               ANL      P2, #0F7H          ; CLOSE VALVE
0084  234D        190  PUMP1:       MOV      A, #OCCL-PG3       ; "OCCLUDE"
0086  5408        191               CALL     DALPHA
                  192
                  193  ; OCCLUDING PRESSURE > 40 CHECK
                  194
0088  34FA        195  PUMP2:       CALL     READP              ; READ PRESSURE
008A  E688        196               JNC      PUMP2              ; PRESSURE NEG?
008C  2350        197               MOV      A, #40+2           ; COMPARE WITH 40 MM HG
008E  BA00        198               MOV      REX, #0
0090  5476        199               CALL     DMINC
0092  E688        200               JNC      PUMP2              ; PTMP < 40
0094  BDFF        201               MOV      COUNT, #0FFH       ; "PRESS" FLAG
                  202
                  203  ; OCCLUDE PRESSURE CHECK
                  204
0096  B920        205  RSTMP:       MOV      R1, #PMAX          ; INITIAL PMAX
0098  74EC        206               CALL     DMOVE
009A  B92E        207               MOV      R1, #PMIN          ; INITIAL PMIN
009C  74EC        208               CALL     DMOVE
009E  B91E        209  PUMP3:       MOV      R1, #AUX22         ; 2.5 SECS
00A0  B119        210               MOV      @R1, #25
00A2  85          211  PUMP4:       CLR      F0                 ; CLEAR PULSE FLG
00A3  23F4        212  PNEXT:       MOV      A, #244            ; PRESS > 250?
00A5  BA01        213               MOV      REX, #1
00A7  5476        214               CALL     DMINC
00A9  E6B3        215               JNC      OCCH1              ; HI OCC PRESS IF >250
00AB  2346        216               MOV      A, #HOCCPR-PG3
00AD  5408        217               CALL     DALPHA
```

```
LOC  OBJ        SEQ          SOURCE STATEMENT

00AF BDFF        218          MOV     COUNT, #0FFH     ; SET "PRESS" FLAG
00B1 04BC        219          JMP     OCCOK
00B3 FD          220 OCCOK1:  MOV     A, COUNT         ; CHECK "PRESS" FLAG
00B4 C6BA        221          JZ      OCCOK2
00B6 BD00        222          MOV     COUNT, #0        ; CLR "PRESS" FLAG
00B8 5406        223          CALL    DPRESS           ; "PRESS"
00BA 5410        224 OCCOK2:  CALL    DSPRES
00BC 34FA        225 OCCOK:   CALL    READP            ; NEXT READING
00BE 2346        226          MOV     A, #35+2         ; PRESS <35 CHECK
00C0 BA00        227          MOV     AEX, #0
00C2 5476        228          CALL    DMINC
00C4 E684        229          JNC     PUMP1
                 230
                 231 ; NEW MAXIMUM PRESSURE CHECK
                 232
00C6 B920        233          MOV     R1, #PMAX        ; MAX PRESSURE
00C8 5470        234          CALL    DMINV            ; PTMP-PMAX
00CA F696        235          JC      RSTTMP           ; RESET TIMER, PLS, AMPL
00CC B92E        236 PLIPMX:  MOV     R1, #PMIN        ; PTMP-PMIN
00CE 5470        237          CALL    DMINV
00D0 E6DF        238          JNC     NEWMIN           ; CHECK MAX HEIGHT
00D2 B6A3        239          JF0     PNEXT            ; PULSE ALREADY FOUND
00D4 03FE        240          ADD     A, -#2           ; HOW BIG
00D6 F2A3        241          JB7     PNEXT            ; < 1 MM HG
00D8 95          242          CPL     F0               ; SET PULSE FLAG
00D9 B910        243          MOV     R1, #AUX33       ; PW TIMER
00DB B14B        244          MOV     @R1, #75         ; 60 MSEC
00DD 04A3        245          JMP     PNEXT
00DF 74EC        246 NEWMIN:  CALL    DMOVE            ; PMIN=PTMP
00E1 B910        247          MOV     R1, #AUX33       ; PW CHECK
00E3 B6E7        248          JF0     PUMP5
00E5 04EA        249          JMP     PUMP6
00E7 F1          250 PUMP5:   MOV     A, @R1
00E8 C6F1        251          JZ      PUMP7
00EA B91E        252 PUMP6:   MOV     R1, #AUX22
00EC F1          253          MOV     A, @R1
00ED 96A2        254          JNZ     PUMP4
00EF 2401        255          JMP     INITPS
                 256
                 257 ; OCCLUDE PRESSURE TOO LOW
                 258
00F1 BDFF        259 PUMP7:   MOV     COUNT, #0FFH     ; SET "PRESS" FLAG
00F3 2340        260          MOV     A, #LOCCPR-PG3
00F5 5408        261          CALL    DALPHA
                 262
                 263 ; WAIT UNTIL PTMP >= PMAX
                 264
00F7 34FA        265 NEWOLD:  CALL    READP
00F9 B920        266          MOV     R1, #PMAX        ; COMPARE PTMP:PMAX
00FB 5470        267          CALL    DMINV
00FD E6F7        268          JNC     NEWOLD           ; PTMP>PMAX?
00FF 049E        269          JMP     PUMP3
                 270
                 271 ; SET PULSE COUNT TO MINUS 2 TO IGNORE FIRST TWO PULS
                 272 ; FOR COUNTING PULSES ONLY
```

```
LOC  OBJ         SEQ        SOURCE STATEMENT

                 273
0101 B1FF        274 INITPS: MOV    @R1, #255        ; SEC TIMER <> 0
0103 5406        275         CALL   DPRESS           ; "PRESS"
0105 5410        276         CALL   DSPPES
0107 BCFE        277 SYST0:  MOV    PLSCNT, -#2
                 278
                 279 ; SYSTOLIC PRESSURE
                 280 ; DETECT FIRST FOUR PULSES, DISCARD IF DELTA PRESS >= 1
                 281
0109 27          282         CLR    A
010A AE          283         MOV    PLSVLD, A        ; SET PLSVLD FALSE
010B AF          284         MOV    TENSEC, A        ; SET TENSEC FALSE
010C BD04        285 SYST:   MOV    COUNT, #4        ; FOUR PULSES
010E 7453        286 SYST1:  CALL   PLS
0110 FD          287         MOV    A, COUNT         ; 2 PULSES YET?
0111 03FC        288         ADD    A, -#4
0113 C61F        289         JZ     SYST2
0115 B830        290         MOV    R0, #PR3         ; PR3-PR4
0117 B932        291         MOV    R1, #PR4
0119 5470        292         CALL   DMINV
011B 03EC        293         ADD    A, -#10+2        ; DELTA >= 10?
011D F607        294         JC     SYST0
011F ED0E        295 SYST2:  DJNZ   COUNT, SYST1     ; COLLECTED 4 PULSES?
                 296
                 297 ; CHECK PULSE AMPLITUDES FOR VALID SYSTOLIC CRITERIA
                 298
                 299         CMPH   H2, H1
0121 B829        300+        MOV    R0, #H2
0123 B928        301+        MOV    R1, #H1
0125 34E9        302+        CALL   MINV
0127 E643        303         JNC    H1GTH2           ; BRANCH IF H1>H2
                 304         CMPH   H3, H2
0129 B82A        305+        MOV    R0, #H3
012B B929        306+        MOV    R1, #H2
012D 34E9        307+        CALL   MINV
012F F653        308         JC     HMAXI            ; BRANCH IF H2<=H3
                 309 H13CHK: CMPH   H3, H1
0131 B82A        310+        MOV    R0, #H3
0133 B928        311+        MOV    R1, #H1
0135 34E9        312+        CALL   MINV
0137 E6D1        313         JNC    SYSER            ; ERROR IF H1>H3
                 314         CMPH   H4, H2
0139 B82B        315+        MOV    R0, #H4
013B B929        316+        MOV    R1, #H2
013D 34E9        317+        CALL   MINV
013F E6D1        318         JNC    SYSER            ; ERROR IF H2>H4
0141 2453        319         JMP    HMAXI
                 320 H1GTH2: CMPH   H3, H2
0143 B82A        321+        MOV    R0, #H3
0145 B929        322+        MOV    R1, #H2
0147 34E9        323+        CALL   MINV
0149 E6D1        324         JNC    SYSER            ; ERROR IF H2>H3
                 325         CMPH   H4, H3
014B B82B        326+        MOV    R0, #H4
014D B92A        327+        MOV    R1, #H3
```

```
LOC  OBJ            SOURCE STATEMENT

014F 34E9                   CALL    MINV
0151 E6D1                   JNC     SYSER                 ; ERROR IF H>=H4
0153 3406          HMAXI:   CALL    HSUM                  ; INITIAL HMAX
0155 AB                     MOV     HMAX, A

                   ; SYSTOLIC AMPLITUDE LIMIT CHECK

0156 03E8                   ADD     A, -#24
0158 F6D1                   JC      SYSER
015A B830                   MOV     R0, #PR3              ; SYS = PR3
015C B920                   MOV     R1, #SYS
015E 74EC                   CALL    DMOVE

                   ;DIASTOLIC

                   ; COUNT NUMBER OF PULSES AFTER MEAN
                   ; ARTERIAL PRESSURE

0160 BDFC          DIASCT:  MOV     COUNT, -#4            ; 4 PULSES AFTER MAP
0162 7453          DIAS:    CALL    PLS                   ; NEXT PULSE
0164 3406                   CALL    HSUM                  ; NEW AMPL SUM
0166 FB                     MOV     A, HMAX               ; IS IT MAXIMUM?
0167 37                     CPL     A
0168 17                     INC     A
0169 6A                     ADD     A, AR2                ; HSUM-HMAX
016A F270                   JB7     PLSCHK                ; BRANCH IF NOT MAX.
016C FA                     MOV     A, AR2                ; GET MAX AMPLITUDE
016D AB                     MOV     HMAX, A               ; NEW MAXIMUM
016E 2460                   JMP     DIASCT                ; NEXT PULSE

                   ; DO NOT CHECK FOR DIASTOLIC UNTIL 4 PULSES AFTER MEAN
                   ; ARTERIAL PRESSURE HAVE BEEN DETECTED

0170 1D            PLSCHK:  INC     COUNT                 ; BRANCH IF < 4
0171 FD                     MOV     A, COUNT
0172 F262                   JB7     DIAS

                   ; AFTER A MAXIMUM IS FOUND, DIASTOLIC IS FOUND WHEN 4
                   ; CONSECUTIVE PULSE AMPLITUDE SUM < THRESHOLD.

0174 3406                   CALL    HSUM                  ; ADD AMPLITUDES

                   ; HMAX >= 9 FOR VALID CALCULATIONS

0176 FB                     MOV     A, HMAX
0177 03F7                   ADD     A, -#9
0179 E662                   JNC     DIAS

                   ; DIASTOLIC THRESHOLD AS A FUNCTION OF HMAX:
                   ;        THRESHOLD = HMAX/2] + 4

017B FB            HMAXOK:  MOV     A, HMAX
017C 97                     CLR     C
017D 67                     RRC     A                     ; HMAX/2]
017E 0303                   ADD     A, #3                 ; HMAX/2] + 3
```

```
LOC   OBJ        SEQ             SOURCE STATEMENT

0180  37         383             CPL      A               ; -(HMAX/2) + 4)
0181  6A         384  TSHCHK:    ADD      A, HEX          ; SIGMA - THRESHOLD
0182  F662       385             JB       DIAS            ; BRANCH IF SIG > THR
0184  B82E       386             MOV      R0, #PR2        ; DIASTOLE = PR2
0186  B922       387             MOV      R1, #DIA
0188  74EC       388             CALL     DMOVE
018A  FE         389  TIMEUP:    MOV      A, PLSVLD       ; VALID PULSE COUNT?
018B  9691       390             JNZ      PCNCHK
018D  7452       391             CALL     PLS
018F  248A       392             JMP      TIMEUP
                 393
                 394  ; PULSE COUNT: PMIN = 42, PMAX = 240
                 395
0191  23F9       396  PCNCHK:    MOV      A, #-7          ; MIN PLS = 42
0193  6C         397             ADD      A, PLSCNT       ; 10 SEC PLS COUNT
0194  F29A       398             JB7      PLSNG           ; PULSE COUNT LOW
0196  03DE       399             ADD      A, #-#34        ; MAX PLS = 240
0198  F2A4       400             JB7      PLSCLC          ; BRANCH IF < 41
                 401
                 402  ; PULSE ERROR MESSAGE: " ---"
                 403
019A  23FE       404  PLSNG:     MOV      A, #0FEH        ; " -"
019C  BAEE       405             MOV      AEX, #0EEH      ; "--"
019E  B826       406             MOV      R0, #BCD0
01A0  54E9       407             CALL     DST
01A2  24B0       408             JMP      PLSDSP
                 409
                 410  ; 6X PLSCNT
                 411
01A4  FC         412  PLSCLC:    MOV      A, PLSCNT       ; ACC = PLSCNT
01A5  6C         413             ADD      A, PLSCNT       ; 2X PLSCNT
01A6  6C         414             ADD      A, PLSCNT       ; 3X PLSCNT
01A7  F7         415             RLC      A               ; 6X PLSCNT
01A8  BA00       416             MOV      AEX, #0
01AA  B824       417             MOV      R0, #PTMP       ; SAVE PULSE COUNT
01AC  54E9       418             CALL     DST
01AE  5486       419             CALL     BINBC1
01B0  233C       420  PLSDSP:    MOV      A, #DTBL+8
01B2  5416       421             CALL     DBCD
01B4  B820       422             MOV      R0, #SYS        ; SYSTOLIC PRESSURE
01B6  548C       423             CALL     BINBCD
01B8  2334       424             MOV      A, #DTBL
01BA  5416       425             CALL     DBCD
01BC  B822       426             MOV      R0, #DIA        ; DIASTOLIC PRESSURE
01BE  548C       427             CALL     BINBCD
01C0  2338       428             MOV      A, #DTBL+4
01C2  5416       429             CALL     DBCD
01C4  24D5       430             JMP      DSPEND
                 431
                 432  ; SUBROUTINES
                 433
                 434  ; ADD THE FOUR PULSE AMPLITUDES
                 435
01C6  27         436  HSUM:      CLR      A
01C7  B829       437             MOV      R0, #HTBL       ; PULSE AMPL TABLE
```

```
LOC  OBJ          SOURCE STATEMENT

01C9 BA04                 MOV     AEX, #4
01CB 60           HSUM1:  ADD     A, @R0           ; ADD THE AMPL'S
01CC 18                   INC     R0
01CD EACB                 DJNZ    AEX, HSUM1
01CF AA                   MOV     AEX, A           ; SAVE SUM
01D0 83                   RET

                  ; SYSTOLIC ERROR MESSAGE

01D1 2320         SYSER:  MOV     A, #SYSERR-PG3   ; "SYS ERROR"

                  ; DISPLAY MESSAGE FOR 10 SECONDS AND WAIT FOR RECALL.
                  ; PULSE LITE ON CONTINUOUS AFTER 10 SECONDS.

01D3 5408         DRECAL: CALL    DALPHA
01D5 8A08         DSPEND: ORL     P2, #08H         ; OPEN VALVE
01D7 8980                 ORL     P1, #80H         ; PLS LITE OFF
01D9 2364                 MOV     A, #100          ; TEN SECONDS
01DB 54F2                 CALL    WAIT
01DD 35                   DIS     TCNTI            ; TIME UP
01DE 89FF                 ORL     P1, #0FFH        ; DISPLAY, LITE OFF
01E0 9A0F                 ANL     P2, #0FH         ; DIGIT # 15
01E2 997F                 ANL     P1, #7FH         ; LITE ON
01E4 36E4         AGAIN:  JT0     AGAIN            ; RECALL?
01E6 25                   EN      TCNTI            ; ENABLE TIMER INT
01E7 24D5                 JMP     DSPEND

                  ; SINGLE PRECISION SUBTRACT

01E9 F1           MINV:   MOV     A, @R1           ; 2'S COMPLEMENT
01EA 37                   CPL     A
01EB 17                   INC     A
01EC 60                   ADD     A, @R0
01ED 83                   RET

                  ; READ PRESSURE AND PLACE IN AEX, A. VALUE IS TWICE
                  ; THE PRESSURE IN MM HG. "INS" SENDS INIT CONV COMMAND

01EE 86F2         READPR: JNI     GETP             ; CHECK IF BUSY IS LOW
01F0 24EE                 JMP     READPR           ; NO, TRY AGAIN
01F2 0A           GETP:   IN      A, P2            ; A/D BITS 9,8
01F3 5303                 ANL     A, #03H
01F5 AA                   MOV     AEX, A           ; STORE IN AEX
01F6 08                   INS     A, BUS           ; A/D BITS 7-0
01F7 B81A                 MOV     R0, #PREF
01F9 83                   RET

                  ; PTMP = PRESSURE - REFERENCE PRESSURE IN 1/2 MM HG

01FA 34EE         READP:  CALL    READPR

                  ; PRESSURE - PREF, STORE IN PTMP

01FC B824         PDIF:   MOV     R0, #PTMP        ; 2X PRESS IN PTMP
01FE 54E9                 CALL    DST
```

```
LOC   OBJ           SEQ           SOURCE STATEMENT

0200  B91A          493           MOV     P1, #PREF        ; 2X PREF
0202  5470          494           CALL    DMINV            ; 2X (PTMP-PREF)
0204  44E9          495           JMP     DST              ; STORE IN PTMP
                    496 ;
                    497 ; DISPLAY "PRESS"
                    498
0206  2349          499 DPRESS:   MOV     A, #PRESS-PG3    ; "PRESS"
                    500
                    501 ; SET UP ALPHA MESSAGE SEGMENTS:
                    502 ;      AEX CONTAINS NUMBER BYTES - 1
                    503 ;      LOAD ACC WITH PAGE 3 MESSAGE ADDR, MOVED TO R1
                    504 ;      R1 CONTAINS DTBL ADDRESS
                    505
0208  BA05          506 DALPHA:   MOV     AEX, #5          ; 6 BYTES
020A  A8            507           MOV     P0, A            ; MESG LOCATION
020B  B934          508           MOV     R1, #DTBL        ; FIRST DISPLAY LOCATION
020D  A5            509           CLR     F1               ; F1=0 FOR ALPHA
020E  4420          510           JMP     DISP
                    511
                    512 ; DISPLAY PRESSURE
                    513
0210  B824          514 DSPRES:   MOV     P0, #PTMP
0212  548C          515           CALL    BINDCD
0214  233C          516 DSPRS1:   MOV     A, #DTBL+8
                    517
                    518 ; SET UP BCD NUMBERS SEGMENTS:
                    519 ;      AEX CONTAINS NUMBER BYTES - 1
                    520 ;      P0 CONTAINS ADDRESS BCD0
                    521 ;      LOAD ACC WITH DTBL, DTBL+4, DTBL+8, MOVED TO R1
                    522
0216  BA01          523 DBCD:     MOV     AEX, #1          ; 2 BYTES
0218  B826          524           MOV     P0, #BCD0        ; FIRST 2 DIGITS IN BCD
021A  A9            525           MOV     R1, A            ; DTBL, DTBL+4, DTBL+8
021B  A5            526           CLR     F1               ; F1=1 FOR BCD
021C  B5            527           CPL     F1
021D  4420          528           JMP     DISP
                    529
                    530 ; BASIC DTBL SEGMENT LOADING ROUTINE
                    531
021F  0A            532 NCHAR:    DEC     AEX              ; DEC BYTE COUNT
0220  543B          533 DISP:     CALL    GCHARS           ; A=CHAR/DIGIT PAIR
0222  47            534           SWAP    A                ; MS NIBBLE
0223  542E          535           CALL    G2SEG
0225  543B          536           CALL    GCHARS
0227  542E          537           CALL    G2SEG
0229  18            538           INC     R0               ; NEXT CHAR PAIR
022A  FA            539           MOV     A, AEX           ; BYTE COUNTER
022B  961F          540           JNZ     NCHAR            ; DONE YET?
022D  83            541           RET
                    542
                    543 ; GET THE COMPLEMENTED SEGMENTS AND STORE IN DTBL
                    544 ; BCD SEGMENT TABLE MUST START AT 300H
                    545
022E  530F          546 G2SEG:    ANL     A, #0FH          ; LS NIBBLE ONLY
0230  7634          547           JF1     BCDSG            ; BRANCH IF BCD
```

```
LOC  OBJ     SOURCE STATEMENT

0232 0310            ADD    A,#APHSEG-BCDSEG      ; ALPHA SEG TBL
0234 E3      BCDSG:  MOVP3  A,@A                  ; GET THE SEGMENTS
0235 37              CPL    A                     ; COMPLEMENT SEGMENTS
0236 537F            ANL    A,#7FH                ; MASK PULSE BIT
0238 A1              MOV    @R1,A                 ; STORE IN DTBL
0239 19              INC    R1                    ; NEXT DTBL LOCATION
023A 83              RET

             ; GET THE CHAR/DIGIT PAIR AND LOAD INTO ACC

023B 7640    GCHARS: JF1    BCHAR                 ; BRANCH IF BCD
023D F8              MOV    A,R0                  ; R0=PAGE 3 TBL LOCATION
023E E3              MOVP3  A,@A
023F 83              RET
0240 F0      BCHAR:  MOV    A,@R0                 ; R0=BCD0, BCD1
0241 83              RET

             ; DISPLAY NEXT CHAR/DIGIT ON 12 CHAR LED DISPLAY
             ; ROUTINE RUNS USING REGISTER BANK 1

0242 0A      SEGS:   IN     A,P2                  ; DIG # FROM PORT 2
0243 37              CPL    A
0244 47              SWAP   A                     ; INTO LS NIBBLE
0245 17              INC    A                     ; NEXT DIGIT #
0246 530F            ANL    A,#0FH                ; LS NIBBLE ONLY
0248 A9              MOV    DIGSAV,A              ; SAVE NEXT DIG #
0249 964F            JNZ    NXTINV                ; RESET SEGPTR IF DGT=0
024B B834            MOV    SEGPTR,#DTBL
024D 445B            JMP    INCDIG                ; MUST INC DIGIT
024F 03FE    NXTINV: ADD    A,-#02H               ; DIGIT=2 INVALID
0251 C65B            JZ     INCDIG
0253 03FE            ADD    A,-#02H               ; DIGIT=4 INVALID
0255 C65B            JZ     INCDIG
0257 03FB            ADD    A,-#05H               ; DIGIT=9 INVALID
0259 965C            JNZ    SEGOUT
025B 19      INCDIG: INC    DIGSAV                ; INC DIGIT #
025C F9      SEGOUT: MOV    A,DIGSAV              ; GET DIG #
025D 47              SWAP   A                     ; PUT IN MS NIBBLE
025E 37              CPL    A
025F 53F7            ANL    A,#0F7H               ; VALVE CLOSE = 0
0261 A9              MOV    DIGSAV,A              ; SAVE DIGIT
0262 0A              IN     A,P2                  ; GET VALVE CLOSE BIT
0263 5308            ANL    A,#08H
0265 49              ORL    A,DIGSAV              ; FORM P2 BYTE
0266 897F            ORL    P1,#07FH              ; BLANK DISPLAY
0268 3A              OUTL   P2,A                  ; NEW DIG #
0269 09              IN     A,P1                  ; GET PULSE BIT
026A 5380            ANL    A,#80H
026C 40              ORL    A,@SEGPTR             ; GET COMP SEGMENTS
026D 39              OUTL   P1,A                  ; OUTPUT SEGMENTS
026E 18              INC    SEGPTR                ; NEXT CHAR SEGMENTS
026F 83              RET

             ; WHEN USING SUBTRACT ROUTINES FOR COMPARISON,
             ;          X > Y: CARRY = 1
```

```
LOC  OBJ         SOURCE STATEMENT

                 ;          X = Y: A = 0, CARRY = 1
                 ;          X < Y: CARRY = 0

                 ; DOUBLE PRECISION SUBTRACT:
                 ;          DMINV: X (R0) - Y (R1)
                 ;          DMINC: X (R0) - K (AEX, A)
                 ; DOUBLE PRECISION ADDITION:
                 ;          DADDC: X (R0) + K (AEX, A)

0270 F1          DMINV:   MOV     A, @R1          ; LS BYTE
0271 AA                   MOV     AEX, A          ; SAVE IN AEX
0272 19                   INC     R1              ; MS BYTE
0273 F1                   MOV     A, @R1
0274 2A                   XCH     A, AEX          ; A=LSB, AEX=MSB
0275 C9                   DEC     R1              ; RESTORE R1 PTR
0276 37          DMINC:   CPL     A               ; 1'S COMPLEMENT
0277 2A                   XCH     A, AEX
0278 37                   CPL     A
0279 2A                   XCH     A, AEX
027A 97                   CLR     C               ; SET CARRY
027B A7                   CPL     C
027C 447F                 JMP     DADDC1
027E 97          DADDC:   CLR     C
027F 70          DADDC1:  ADDC    A, @R0          ; 2'S COMP ADDITION
0280 2A                   XCH     A, AEX
0281 18                   INC     R0
0282 70                   ADDC    A, @R0
0283 2A                   XCH     A, AEX          ; A=LSB, AEX=MSB
0284 C8                   DEC     R0              ; RESTORE R0 PTR
0285 83                   RET

                 ; BINARY TO BCD CONVERSION: RESULT IN BCD0,BCD1; X (R0)

0286 B926        BINBC1:  MOV     R1, #BCD0       ; VARIABLE TO BCD0
0288 74EC                 CALL    DMOVE
028A 4499                 JMP     BIN1
028C B926        BINBCD:  MOV     R1, #BCD0       ; VARIABLE TO BCD0

                 ; DIVIDE BY 2, DOUBLE PRECISION RIGHT SHIFT

028E 18                   INC     R0              ; NEED MS BYTES
028F 19                   INC     R1
0290 97                   CLR     C
0291 F0                   MOV     A, @R0          ; "FROM"
0292 67                   RRC     A
0293 A1                   MOV     @R1, A          ; "TO"
0294 C8                   DEC     R0              ; LS BYTES
0295 C9                   DEC     R1
0296 F0                   MOV     A, @R0          ; "FROM"
0297 67                   RRC     A
0298 A1                   MOV     @R1, A

                 ; CONVERSION

0299 B900        BIN1:    MOV     R1, #0          ; ACCUMULATE 100'S DIGIT
```

```
LOC  OBJ         SEQ         SOURCE STATEMENT

029B BA00        658 HNDS:   MOV     AEX, #0          ; 100 IN AEX, A
029D 2364        659         MOV     A, #100
029F B826        660         MOV     R0, #BCD0
02A1 5476        661         CALL    DMINC            ; BCD# - 100
02A3 E6AA        662         JNC     LT100            ; BRANCH IF BCD#-100<10
02A5 19          663         INC     R1               ; INC 100'S COUNTER
02A6 54E9        664         CALL    DS1              ; BCD# = BCD# - 100
02A8 449B        665         JMP     HNDS             ; SUBTRACT 100 AGAIN
02AA F9          666 LT100:  MOV     A, R1            ; MS DIGIT TO BCD0
02AB B900        667         MOV     R1, #0           ; ACCUMULATE TEN'S DIGIT
02AD 43F0        668         ORL     A, #0F0H         ; BLANK LEADING 0
02AF B826        669         MOV     R0, #BCD0
02B1 20          670         XCH     A, @R0           ; GET BCD0, < 100
02B2 AA          671 TENS:   MOV     AEX, A           ; SAVE 10'S VALUE IN AE
02B3 03F6        672         ADD     A, -#10          ; SUBTRACT 10
02B5 E6BA        673         JNC     LT10             ; BRANCH IF REMAINDER<1
02B7 19          674         INC     R1               ; INCREMENT 10'S COUNT
02B8 44B2        675         JMP     TENS             ; SUBTRACT 10 AGAIN
02BA F9          676 LT10:   MOV     A, R1            ; GET TEN'S
02BB 47          677         SWAP    A                ; TEN'S TO MS NIBBLE
02BC 4A          678         ORL     A, AEX           ; UNIT'S TO LS NIBBLE
02BD 18          679         INC     R0               ; POINT TO BCD1
02BE A0          680         MOV     @R0, A           ; TEN'S, UNIT'S TO BCD1
02BF 83          681         RET
                 682
                 683 ; BLINK MESSAGE ON DISPLAY
                 684
02C0 54C4        685 BLINK:  CALL    BLINK1           ; MESSAGE ON DISPLAY
02C2 232D        686         MOV     A, #BLANK-PG3    ; BLANK DISPLAY
02C4 5408        687 BLINK1: CALL    DALPHA
02C6 2303        688         MOV     A, #3
02C8 44F2        689         JMP     WAIT
                 690
                 691 ; CHECK IF BATTERY IS BELOW SYSTEM OPERABLE LIMITS
                 692
02CA 0A          693 BLEAD:  IN      A, P2
02CB 52D3        694         JB2     BEXIT            ; BRANCH IF BATT OK
02CD 2325        695 DSPDED: MOV     A, #CHARGE-PG3   ; "CH DC"
02CF 54C0        696         CALL    BLINK
02D1 44CD        697         JMP     DSPDED
02D3 83          698 BEXIT:  RET
                 699
                 700 ; SHIFT UP'S FOR PULSE AMPLITUDE
                 701
02D4 BA03        702 SHFTH:  MOV     AEX, #3          ; 3 SHIFTS
02D6 B829        703         MOV     R0, #HTBL+1      ; "FROM"
02D8 B928        704         MOV     R1, #HTBL        ; "TO"
02DA 54E2        705         CALL    SHFT1
                 706
                 707 ; SHIFT UP'S FOR PRESSURE
                 708
02DC BA06        709 SHFTP:  MOV     AEX, #6          ; 6 SHIFTS
02DE B82E        710         MOV     R0, #PTBL+2      ; "FROM"
02E0 B92C        711         MOV     R1, #PTBL        ; "TO"
                 712
```

```
LOC  OBJ        SEQ       SOURCE STATEMENT

                713 ; SHIFT SUBROUTINE
                714
02E2 F0         715 SHFT1:  MOV    A, @R0          ; "FROM"
02E3 A1         716         MOV    @R1, A          ; "TO"
02E4 18         717         INC    R0
02E5 19         718         INC    R1
02E6 EAE2       719         DJNZ   AEX, SHFT1
02E8 83         720         RET
                721
                722 ; DOUBLE PRECISION STORE: X (R0) = AEX, A
                723
02E9 A0         724 DST:    MOV    @R0, A          ; LS BYTE
02EA 2A         725         XCH    A, AEX          ; MS BYTE
02EB 18         726         INC    R0
02EC A0         727         MOV    @R0, A
02ED 2A         728         XCH    A, AEX          ; RESTORE AEX, A
02EE C8         729         DEC    R0              ; RESTORE R0
02EF 83         730         RET
                731
                732 ; DELAY 100 MSEC INCREMENTS, # IN ACC
                733
02F0 230A       734 WT1SEC: MOV    A, #10          ; 1 SEC DELAY
02F2 B81E       735 WAIT:   MOV    R0, #AUX22
02F4 A0         736         MOV    @R0, A
02F5 F0         737 WT:     MOV    A, @R0
02F6 96F5       738         JNZ    WT
02F8 83         739         RET
                740
                741 ; SEGMENT TABLES: MUST BE AT BEGINNING OF PAGE 3
                742
0300            743         ORG    PG3
                744
0300 3F         745 BCDSEG: DB     3FH, 06H, 5BH, 4FH, 66H, 6DH, 7DH, 07H
0301 06
0302 5B
0303 4F
0304 66
0305 6D
0306 7D
0307 07
0308 7F         746         DB     7FH, 67H, 77H, 7CH, 39H, 5EH, 40H, 0
0309 67
030A 77
030B 7C
030C 39
030D 5E
030E 40
030F 00
                747
0310 77         748 APHSEG  DB     77H, 39H, 5EH, 79H, 76H, 06H, 3EH, 38H
0311 39
0312 5E
0313 79
0314 76
0315 06
```

```
LOC  OBJ          SEQ         SOURCE STATEMENT

0316 3E
0317 38
0318 71           749         DB        71H, 3FH, 5CH, 73H, 50H, 6DH, 6EH, 00H
0319 3F
031A 5C
031B 73
031C 50
031D 6D
031E 6E
031F 00
                  750
                  751 ; MESSAGES
                  752
0320 FD           753 SYSERR: DB        0FDH, 0EDH
0321 ED
0322 F3           754 PERROR: DB        0F3H, 0CCH, 0ACH
0323 CC
0324 AC
0325 FF           755 CHARGE: DB        0FFH, 0FFH, 0FFH, 0F1H, 4FH, 21H
0326 FF
0327 FF
0328 F1
0329 4F
032A 21
032B 10           756 CAL:    DB        10H, 7FH
032C 7F
032D FF           757 BLANK:  DB        0FFH, 0FFH
032E FF
032F FF           758 CUFF:   DB        0FFH, 0FFH, 0FFH, 0FFH, 16H, 88H
0330 FF
0331 FF
0332 FF
0333 16
0334 88
0335 F2           759 DIAERR: DB        0F2H, 50H, 0F3H, 0CCH, 0ACH
0336 50
0337 F3
0338 CC
0339 AC
033A FF           760 LOBATT: DB        0FFH, 0FFH, 0FFH, 0F7H, 9FH, 21H
033B FF
033C FF
033D F7
033E 9F
033F 21
0340 79           761 LOWCPP: DB        79H, 0F9H, 11H, 0FBH, 0C3H, 0DDH
0341 F9
0342 11
0343 FB
0344 C3
0345 DD
0346 45           762 HOLCPP: DB        45H, 0F9H, 11H
0347 F9
0348 11
0349 FB           763 PRESS:  DB        0FBH, 0C3H, 0DDH, 0FFH
```

```
LOC   OBJ        SEQ           SOURCE STATEMENT

034A  C3
034B  DD
034C  FF
034D  FF         764 OCCL:   DB      0FFH, 0FFH, 0F9H, 11H, 76H, 23H
034E  FF
034F  F9
0350  11
0351  76
0352  23

                 765
                 766 ; SUBROUTINES - MORE
                 767
                 768 ; PULSE DETECT
                 769
0353  540A       770 PLS:    CALL    BDEND            ; CHECK BATTERY
0355  54D4       771         CALL    SHFTH            ; MOVE H'S, PR'S UP 1
0357  85         772 PLS1:   CLR     F0               ; CLEAR PULSE FLAG
0358  B824       773         MOV     R0, #PTMP
035A  B932       774         MOV     R1, #PLAST
035C  746C       775         CALL    DMOVE            ; PLAST=PTMP
035E  B828       776         MOV     R0, #HD
0360  B000       777         MOV     @R0, #0          ; INITIAL HEIGHT = 0
0362  34FA       778 STLAST: CALL    READP            ; READ PRESSURE, PTMP
0364  2330       779         MOV     A, #30+2         ; PRESS < 30?
0366  BA00       780         MOV     REX, #0
0368  5476       781         CALL    DMINC
036A  F678       782         JF1     ST1              ; BRANCH IF >= 30
036C  FC         783         MOV     A, PLSCNT        ; CHECK FOR 4 PULSES
036D  03FD       784         ADD     A, -#3
036F  37         785         CPL     A                ; NEED COMP OF MSB
0370  F274       786         JB7     DIAER            ; > 4 PULSES?
0372  24D1       787         JMP     SYSER            ; "SYS ERROR"
0374  2335       788 DIAER:  MOV     A, #DIAERR-PG3   ; "DIA ERROR"
0376  24D3       789         JMP     DPECAL
0378  B922       790 ST1:    MOV     R1, #PLAST       ; COMPARE PTMP AND PLAST
037A  5470       791         CALL    DMINV            ; H=PTMP-PLAST<256
037C  B81C       792         MOV     R0, #NUM33       ; PULSE WIDTH TIMER
037E  B92B       793         MOV     R1, #HD          ; SET UP FOR AMP CHK
0380  F6A2       794         JNC     PCHKS            ; BRANCH IF PTMP < PLAST
0382  AA         795         MOV     REX, A           ; SAVE H IN REX
0383  F1         796         MOV     A, @R1           ; COMPARE H WITH HD
0384  37         797         CPL     A
0385  17         798         INC     A
0386  6A         799         ADD     A, REX           ; H - HD
0387  F262       800         JB7     STLAST           ; H<HD, NEXT READING
0389  FA         801         MOV     A, REX           ; HD = H
038A  A1         802         MOV     @R1, A           ; HD = H
038B  03FE       803         ADD     A, -#2           ; AMPL THRESHOLD=1.0 MM
038D  F262       804         JB7     STLAST
                 805
                 806 ; PULSE WIDTH TIMER SET UP
                 807
038F  B694       808         JF0     AUXCHK
0391  95         809         CPL     F0
0392  B04B       810         MOV     @R0, #75         ; SET FOR PULSE ONSET
                                                      ; 60 MSEC
```

```
LOC  OBJ        SEQ        SOURCE STATEMENT

0394 F0         811 AUSCHK: MOV     A, @R0
0395 9662       812         JNZ     STLAST
                813
                814 ; VALID PULSE- TURN ON LITE, CHECK MAX AMPLITUDE
                815
0397 997F       816         ANL     P1, #7FH         ; PLS LITE ON
0399 23F0       817         MOV     A, -H3+2         ; MAX PULSE AMPL
039B 61         818         ADD     A, @R1
039C E662       819         JNC     STLAST
039E 2322       820         MOV     A, #ERROR-PG3    ; "ERROR"
03A0 24D3       821         JMP     DPECAL
                822
                823 ; VALID PULSE WIDTH CHECK
                824
03A2 09         825 PCHKS:  IN      A, P1            ; VALID PULSE WIDTH?
03A3 37         826         CPL     A                ; BIT 7 IS PLS LITE
03A4 F2C1       827         JB7     PCHKS1           ; BRANCH IF YES
                828
                829 ; NO PULSE, DECREASING OCCLUDING PRESSURE
                830
03A6 5410       831         CALL    DSPPFS
03A8 B91E       832         MOV     R1, #AUX22       ; TIME UP YET?
03AA F1         833         MOV     A, @R1
03AB 9657       834         JNZ     PLS1             ; BRANCH IF NOT
03AD FF         835         MOV     A, TENSEC        ; TEN SEC UP?
03AE 96B9       836         JNZ     PVALID
03B0 FC         837         MOV     A, PLSCNT        ; ANY PULSES YET?
03B1 F257       838         JB7     PLS1
03B3 BFFF       839         MOV     TENSEC, #0FFH    ; TEN SEC UP
03B5 B11E       840         MOV     @R1, #30         ; 3 SEC TIMEOUT
03B7 6457       841         JMP     PLS1
03B9 FE         842 PVALID: MOV     A, PLSVLD        ; VALID PULSE COUNT?
03BA 9674       843         JNZ     DIAER            ; NO PULSE FOR 3 SEC
03BC BC00       844         MOV     PLSCNT, #0
03BE BEFF       845         MOV     PLSVLD, #0FFH
03C0 83         846         RET
                847
                848 ; CHECK PULSE AMPLITUDE: CANNOT BE 1 MM HG LARGER
                849 ; THAN PREVIOUS PULSE
                850
03C1 8980       851 PCHKS1: ORL     P1, #80H         ; PLS LITE OFF
03C3 B82A       852         MOV     R0, #H3
03C5 F0         853         MOV     A, @R0           ; A=H3
03C6 0302       854         ADD     A, #2            ; A=H3+2
03C8 AA         855         MOV     HEX, A           ; SAVE H3+2
03C9 37         856         CPL     A
03CA 17         857         INC     A
03CB 61         858         ADD     A, @R1           ; H4-(H3+2)
03CC E6D0       859         JNC     WINDOW           ; BRANCH IF H4<H3+2
03CE FA         860         MOV     A, HEX           ; H4=H3+2
03CF A1         861         MOV     @R1, A
                862
                863 ; SET UP TEN SECOND PULSE COUNT WINDOW
                864
03D0 FC         865 WINDOW: MOV     A, PLSCNT        ; PLS COUNT = 0?
03D1 96DA       866         JNZ     TPGCHK
03D3 B91D       867         MOV     R1, #AUX11       ; SET UP 10 SEC TIMER
03D5 B17D       868         MOV     @R1, #125        ; 100 MSEC
03D7 19         869         INC     R1               ; 10 SECONDS
03D8 B164       870         MOV     @R1, #100
                871
                872 ; PULSE COUNT
                873
03DA B91E       874 TPGCHK: MOV     R1, #AUX22       ; SEC COUNTER
03DC FF         875         MOV     A, TENSEC        ; 10 SEC UP?
03DD 96E5       876         JNZ     TENUP            ; BRANCH IF > 10
03DF F1         877         MOV     A, @R1           ; 10 SEC CHECK
03E0 C6E5       878         JZ      TENUP            ; BRANCH IF 10 SEC UP
03E2 1C         879         INC     PLSCNT           ; ONE MORE PULSE
03E3 64EB       880         JMP     PEXIT
03E5 BEFF       881 TENUP:  MOV     PLSVLD, #0FFH    ; VALID PULSE COUNT
```

```
LOC  OBJ          SEQ           SOURCE STATEMENT
03E7 B8FF                       MOV     TENSEC, #0FFH   ; 10 SECONDS UP
03E9 B11E                       MOV     @R1, #30        ; 3 SEC TIME OUT

                   ; PULSE AMPLITUDE TESTING

                                IF      TEST EQ TRUE

                   PEXIT:       MOV     R1, #HD         ; GET AMPLITUDE
                                MOV     A, @R1
                                MOV     R1, #DTBL+7     ; DISPLAY POSITION
                                JMP     BCDSG           ; DISPLAY PLS AMPL

                                ELSE

03EB 83            PEXIT:       RET

                                ENDIF

                   ; DOUBLE MOVE: R0 = "FROM" ADDRESS, R1 = "TO" ADDRESS

03EC F0            DMOVE:       MOV     A, @R0          ; "FROM"
03ED A1                         MOV     @R1, A          ; "TO"
03EE 18                         INC     R0
03EF 19                         INC     R1
03F0 F0                         MOV     A, @R0          ; FROM, MS BYTE
03F1 A1                         MOV     @R1, A          ; TO, MS BYTE
03F2 C8                         DEC     R0              ; RESTORE PTRS
03F3 C9                         DEC     R1
03F4 83                         RET

                   ; GET REFERENCE PRESSURE AND STORE IN PREF

03F5 34EE          REFP:        CALL    READPR          ; R0 = PREF
03F7 54E9                       CALL    DST
03F9 83                         RET

                                END
```

| | | | | | | | | | |
|---|---|---|---|---|---|---|---|---|---|
| AEX | 0002 | AGAIN | 01E4 | AMBCHK | 0029 | APHSEG | 0310 | ASAV | 0007 |
| AUX1 | 0005 | AUX11 | 001D | AUX2 | 0006 | AUX22 | 001E | AUX3 | 0004 |
| AUX33 | 001C | AUXCHK | 0304 | BLDU | 0026 | BCDSEG | 0300 | BCDSG | 0234 |
| BCHAR | 0240 | BDEAD | 020A | BEXIT | 0203 | BIN1 | 0299 | BINBC1 | 0286 |
| BINBCD | 028C | BLANK | 0320 | BLINK | 0200 | BLINK1 | 0204 | CAL | 032B |
| CALCON | 0078 | CALIB | 0032 | CALMIN | 0074 | CALPOS | 0044 | CHARGE | 0325 |
| CLOSE | 007E | CMPH | 0000 | COUNT | 0005 | CUFF | 032F | DADDC | 027E |
| DADDC1 | 027F | DALPHA | 0200 | DDCD | 0216 | DELCHK | 004A | DELTA | 005E |
| DIA | 0022 | DIAER | 0374 | DIAERR | 0335 | DIAS | 0162 | DIASCT | 0160 |
| DIGSAV | 0001 | DISP | 0220 | DMINC | 0276 | DMINV | 0270 | DMOVE | 03EC |
| DPRESS | 0206 | DRECAL | 01D3 | DSPDED | 020D | DSPEND | 01D5 | DSPRES | 0210 |
| DSPRS1 | 0214 | DST | 02E9 | DTBL | 0034 | FALSE | 0000 | G2SEG | 022E |
| GCHARS | 023B | GETP | 01F2 | H1 | 0028 | H13CHK | 0131 | H1GTH2 | 0143 |
| H2 | 0029 | H3 | 002A | H4 | 002B | HD | 002B | HMAX | 0003 |
| HMAX1 | 0153 | HMAXOK | 017B | HNDS | 029B | HOLCPR | 0346 | HSUM | 01C6 |
| HSUM1 | 01CB | HTBL | 0028 | INCDIG | 0258 | INITPS | 0101 | LOBATT | 033A |
| LOCCPR | 0340 | LOOP | 006A | LOOP1 | 0078 | LT10 | 02BA | LT100 | 02AA |

-continued

```
MCHK    0012   MCUFF   0068   MINV    01E9   NCHAR   021F   NEWMIN  000F
NEWOCC  00F7   NXTINV  024F   OCCL    034D   OCCUK   00BC   OCCOK1  00B3
OCCOK2  00BA   P40     0028   PCHKS   03A2   PCHKS1  03C1   PCNCHK  0191
PDIF    01FC   PERROR  0322   PEXIT   03EB   PG3     0300   PLAST   0032
PLS     0353   PLS1    0377   PLSCHK  0170   PLSCLC  01A4   PLSCNT  0004
PLSDSP  01BA   PLSNG   0190   PLSVLD  0006   PLTPMX  00CC   PMAX    002C
PMIN    002E   PNEXT   00A7   PP1     002C   PP2     002E   PP3     0030
PR4     0032   PREF    001A   PRESS   0349   PTBL    002C   PTMP    0024
PUMP1   0084   PUMP2   0089   PUMP3   009E   PUMP4   00A2   PUMP5   00E7
PUMP6   00EA   PUMP7   00F1   PVALID  03B9   READP   01FA   READPR  01EE
REFP    03F5   RSTTMP  0096   SEGOUT  025C   SEGPTR  0000   SEGS    0242
SEGSET  001E   SGPTR   0018   SHFT1   02E2   SHFTH   0204   SHFTP   020C
ST1     0378   START   0000   STLAST  0362   SYS     0020   SYSER   01D1
SYSERR  0320   SYST    010C   SYS10   0107   SYST1   010E   SYST2   011F
TENS    02B2   TENSEC  0007   TENUP   03E5   TEST    0000   TEXIT   001C
TFRCHK  03DA   TIMER   0007   TIMEUP  0190   TIMINT  001A   TRUE    00FF
TSHCHK  0181   WAIT    02F2   WINDOW  03D0   WT      02F5   WT1SEC  02F0

ASSEMBLY COMPLETE,  NO ERRORS
```

Sequencing of the Apparatus

Before proceeding with a description of the source listing and the detailed steps carried out by the apparatus of FIGS. 1-8, it will be helpful to summarize the sequencing of the instrument.

After the occluding cuff is placed on the arm of the patient in the conventional manner, the main on/off switch is moved to the on position, and the system is reset by momentarily depressing the reset switch. The "CAL" message is then displayed for at least two seconds while the system checks that the cuff pressure is at atmospheric pressure and while the reference pressure is measured. The "CAL" message may be displayed for more than two seconds if the cuff pressure has to bleed down (e.g., if the instrument was just used, and a new measurement cycle was initiated by pressing the reset button before the cuff pressure was allowed to completely bleed down at the end of the previous measurement cycle).

The "CUFF" message is then normally displayed to inform the operator to press the recall/cuff button. Alternatively, if the battery potential is less than 9.8 volts, but higher than 9.4 volts, the "LO dC" message is displayed to inform the operator not only to press the recall/cuff button, but also to recharge the batteries when time permits. If the battery potential is detected to be less than 9.4 volts, either now or subsequently, a blinking "CH dC" message is displayed to inform the operator that the unit may not be used until the batteries are recharged.

As soon as the recall/cuff button is momentarily operated, the "OCCLUdE" message is displayed. The operator is thus informed to start pumping the bulb. If the operator starts to pump the bulb before pressing the recall/cuff button, the "CUFF" message will blink. In such a case, the reset switch must be operated and the whole process started from the beginning.

The "OCCLUdE" message remains on the display as the pumping proceeds until a pressure of 40 mm Hg is present in the cuff. At this time, the "PrESS" (pressure) message is displayed together with the instantaneous cuff pressure.

When the occluding pressure in the cuff exceeds 250 mm Hg, the "HI OCC PrESS" message is displayed without a pressure value. The operator can still pump up the bulb, although generally this is not necessary.

If the operator has not pumped the bulb for 2.5 seconds, yet a blood pressure pulse representing a rise of at least 1.0 mm Hg was nevertheless detected by the instrument, it is an indication that the artery was not fully occluded (as will be explained below). The "LO OCC PrESS" message is displayed to inform the operator to pump up the cuff pressure.

Provided that 2.5 seconds go by after the operator stops pumping the bulb without the detection of a pulse having an amplitude of at least 1.0 mm Hg, the system begins to take systolic and diastolic pressure measurements, along with a measurement of pulse rate. As the occluding pressure bleeds down, the message "PrESS" is displayed, together with the decreasing cuff pressure value. Although each blood pressure pulse results in an instantaneous rise and then fall of cuff pressure, these transient changes are not displayed. The cuff pressure value which is displayed during the measurement cycle continuously decreases. However, whenever a blood pressure pulse is in progress, the pulse light is illuminated.

During the measurement cycle, artifacts may result in the display of an "Error" message. An error during systolic pressure processing results in the display of a "SYS Error" message, and an error during diastolic pressure processing results in the display of a "dIA Error" message. In all three cases, no measurement results are displayed, and the reset button must be operated to initialize the system for taking a new measurement.

At the conclusion of the measurement cycle, systolic pressure, diastolic pressure and pulse rate are displayed. If the pulse rate determination is too low or too high, indicating that an error probably occurred, the systolic and diastolic pressure values are displayed, but instead of a 3-digit pulse rate value being shown three dashes are displayed.

The final results (an error message or numerical values) are displayed for ten seconds. The display is then blanked, but the pulse light turns on to indicate to the operator that the last display can be recalled by pressing the recall/cuff button. If the button is operated, the pulse light turns off and the last message will be displayed for another ten seconds, following which it will be blanked and the pulse light will turn on again.

Another measurement cycle then can be initiated by pressing the reset button.

Organization of Data Memory and Display Procedure

Statements 9–72 define various labels used in the source program. At lines 9–11, TRUE is set equal to OFFH, and FALSE and TEST are both set equal to 0. Of the eight registers in bank 0, R0 and R1 are used as general pointers and are not provided with any labels. Registers R2–R7 are assigned labels which correspond to the respective information which they contain; the reasons for the selection of the various labels will become apparent below.

Six of the registers in bank 1 are similarly given labels. Registers R2 and R3 in this bank are used to store a double-precision reference pressure.

Starting with statement 39, some of the other locations in the 64-location data memory are provided with labels. Additionally, some of the bank 0 and bank 1 registers are given alternate labels. For example, in line 28, the label SEGPTR is assigned to register R0 in bank 1. Yet line 39 refers to this same register as SGPTR. The reason for this is that different labels are required when running the 8048 microprocessor working with the two different register banks. Label SEGPTR is used when running the machine with bank 1. The actual value of SEGPTR is 0, since the first working register in bank 1 (R0′) is register 0 for that bank. But when running the processor with bank 0, the first register in bank 1 is referred to by its RAM address 24. Thus the label SGPTR actually has a value of 24.

At line 41, data memory locations 26 and 27 (registers R2 and R3 in bank 1) are defined as storing a double-precision (16-bit) reference pressure. The label PREF refers to the first of these two locations. (In general, in the following description, a label such as PREF is used loosely to refer either to the data memory location which contains the first, least significant byte of the 16-bit value or to the 16-bit value itself, depending on the context in which the label is used.)

Line 52 sets aside four data memory locations for storing pulse heights. The first of these is labeled HTBL and the last, as defined by line 53, is labeled HD. The eight locations starting at data memory address 54 are used to store four double-precision variables which represent pressure values. The last two of these locations store the "last" value, with the first location of these two being labeled PLAST. Lines 63–68 define alternate labels for the pressure value locations.

Statement 56 reserves the last 12 data memory locations (52–63) for a "display table" with location 52 being labeled DTBL. The display contains 12 character positions, some of which are blanks for particular messages. Every 800 microseconds, a different character is refreshed or newly displayed under timer interrupt control. The system does not then determine the current message which is being displayed, retrieve the character which is to be refreshed in that message, access the display segment information for that character, and finally use the segment information to control refreshing of the character (or the display of a new character if a message is to be changed). Rather, whenever an entirely new, or part of a, message is required (alphabet characters or digit characters), the system retrieves all of the new characters, and for each of the new characters derives display segment information. A single byte defines those segments for each character which are to be turned on, and those which are to be left off. The segment-controlling bytes are then stored in respective ones of data memory locations 52–63. (When an entirely new message is to be displayed, 12 bytes are stored in the display table; otherwise, only bytes corresponding to digit characters to be up-dated are stored in the display table.) Thereafter, at 800-microsecond intervals, a different one of these twelve data memory locations is accessed, and the respective character position of the display is refreshed or up-dated in accordance with the stored segment information. Each character is thus turned on at intervals of $12\times800$ microseconds, or 9.6 milliseconds, a rate high enough to avoid flicker, thus giving the appearance of a continuously illuminated display.

The last definitional statement, at line 72, is that which defines PG3 as ROM address 300H, the start of the fourth page of program memory. At this point, it will be helpful to refer to source statement lines 741–764. The 16 bytes stored starting at ROM address 300H (BCDSEG) represent display segment bits for the ten digits b 0–9, four HEX digits A, b, C, d, a dash (minus sign), and a blank. (As will be described below, the HEX digits are displayed only in a testing mode—not by an instrument used by a purchaser. There are 16 alphabet characters—A, C, d, E, F, H, I, L, o, O, P, r, S, U, Y, and a blank, which are used to make up all of the messages, and display segment bit information for these 16 characters are stored starting at ROM address 310H (APHSEG).

The word messages themselves are defined in lines 753–764. Each byte represents two characters of a message. For example, consider the message "SYSERR" defined at line 753. The first byte of the message is FDH; the 4-bit HEX value F represents a blank (b) and the 4-bit HEX value D represents the letter S. The first six bytes starting at ROM address 320H represent the following pairs of characters, where a b represents a blank; bS, YS, bE, rr, or bb. The four bits used to represent each character have no predetermined relationship with the character; each 4-bit value is simply an offset which is used to retrieve the respective segment information, as will be described below.

The "PERROR" message overlaps the "SYSERR" message, the former message beginning at ROM address 322H. The six bytes used to define this message represent the character pairs bE, rr, or, bb, bb, bb. Similarly, the "CHARGE" message overlaps the "PERROR" message and begins at location 325H. The character pairs represent bb, bb, bb, bC, Hb, dC. Similar remarks apply to all of the other messages.

Suppose, for example, that it is necessary to display the "CHARGE" message. The processor retrieves the 12 respective HEX digits FFFFFFF14F21. The first HEX digit is used as an offset and added to base address APHSEG (line 748, ROM address 310H). The display segment byte which is thus pointed to is that a ROM address 310H+FH, or 31FH. This byte (00) is stored in the first location DTBL of the display table, having data memory address 52. When the two HEX digits 00 are stored in this location of the data memory, the first character of the display is blanked. Because each of the next six HEX digits in the "CHARGE" message is also an F, the display segment bytes which are stored in data memory locations 53–58 are also 00 and control the display of blanks.

The next HEX digit in the "CHARGE" message is 1, and when this offset is added to APHSEG, ROM address 311H is pointed to. The HEX byte 39 at this location is thus stored at location 59 in the data memory, and it controls the display of a C in the eighth character position of the display. In a similar manner, the last four HEX digits of the "CHARGE" message—4, F, 2 and 1—are used as offsets from address APHSEG to access the four bytes which are segment information for the characters H, b (blank), d and C. These bytes are stored in the last four locations in the display table. Once the segment data is thus stored, up-dating of the display is automatic, with a different display segment byte being retrieved from the data memory every 800 microseconds and used to control the character display "CH dC".

When digit characters are to be displayed, a similar procedure is followed. But this time each computed digit is used as an offset to point to a display segment byte starting at base address BCDSEG (line 745). Once a byte of segment information is stored in one of the twelve positions of the display table in the data memory, display of the respective digit is automatic.

This technique requires the processor to "form" a message, or up-date it with new digit values, only once, by storing the appropriate display segment bytes in the data memory. Thereafter, the processor need not form the message, and must only change or refresh the display in accordance with the display segment information in the data memory.

It should be noted that the overlapping of the alphabet character messages (lines 753–764), as described above, results in some of the messages being displayed on the left, some in the middle, and some on the right of the display. The reason for doing this is simply to conserve ROM address space. By overlapping the messages, some of the same offset HEX digits can be used to represent characters in up to three messages. The necessary result of this ROM conservation is that the messages are actually displayed starting at different positions in the 12-position display.

Start-up of Machine, Timer Interrupt and Message Display

Following closing of the main on/off switch, the reset button is operated. The RESET input of the 8048 microprocessor is pulsed high. At the trailing edge of the pulse, the program counter is automatically loaded with address 0, the origin of the ROM program. When a 6-MHz crystal is used to derive the clock, a 400-kHz machine cycle clock is generated internally. This latter clock waveform is passed through an internal $\div 32$ prescaler to apply a 12.5-kHz clock to the 8-bit timer/counter included on the chip. The timer is thus incremented every 80 microseconds. Initially, the timer/counter interrupt is not enabled and all that is done is to initialize the timer.

The first instruction (line 78) stores the decimal number $-10$ in the accumulator, and the next instruction transfers this number to the timer/counter. Register R0 is then loaded with the value of SGPTR (24), which identifies the first register (R0′) in register bank 1. The system then jumps to the SEGSET routine at line 116.

At line 116, register R0 is loaded with the value 52 (DTBL), identifying the first of the 12 data memory locations used to store display segment information. During assembly, the assembler computes the value CAL–PG3, and generates an instruction at line 117 which causes this value to be loaded in the accumulator. CAL is the absolute address (32BH) in ROM of the start of the "CAL" (calibrate) message (see line 756). When the value PG3 (300H) is subtracted from the value CAL, the difference represents the relative address in page 3 of ROM at which the "CAL" message offsets begin.

At line 118, a call is made to the DALPHA subroutine at line 506. This routine is used repeatedly and will be described in detail.

The number 5 is first stored in the AEX register (R2, see line 17). This register is used to count operations on six bytes (12 offsets) of the message to be displayed, representing 12 characters. (In general, to change any part of a message, AEX is initially loaded with one less than the number of bytes, or double characters, to be processed.) The accumulator contains the relative address in page 3 of ROM of the first byte whose two characters are to be displayed. The MOV instruction in line 507 causes this relative address to be stored in register R0. When the next instruction is executed, the first display table location (DTBL) in the data memory which is to be changed is stored in register R1. Flag F1 is then cleared, as it is whenever alphabet character message segments are to be loaded into the display table, and a jump is made to the DISP routine at line 533.

A call is immediately made to the GCHARS subroutine at line 558. Since the F1 flag is cleared, a branch is not made to BCHAR. At line 559, the accumulator is loaded with the relative address in page 3 of the byte representing the first two characters of the "CAL" message (contained in register R0), and the MOVP3 instruction then causes the byte at this location to be moved to the accumulator. A return is then made to line 534.

The byte now in the accumulator represents the first two characters of the message. In order to operate on the four most significant bits of the byte, representing the first character, it is necessary to place this HEX digit in the four least significant bits of the accumulator; this is accomplished by the SWAP instruction at line 534. A call is then made to the G2SEG subroutine at line 546. By ANDing the accumulator with OFH, the four most significant bits in the accumulator are cleared. At line 547, a branch is not made to BCDSG because the F1 flag is cleared, since an alphabet character is to be displayed. The instruction at line 548 causes the relative address in page 3 of the first alphabet character segment byte to be added to the contents of the accumulator, and thus the accumulator represents the relative address in page 3 of the display segment byte associated with the first character to be displayed. At line 549, the display segment byte of interest is loaded into the accumulator, and at line 550 the accumulator is complemented. (The accumulator is complemented because all outputs of the microprocessor connected to the display are inverted by external inverters included for current amplification.)

The seven least significant bits of the accumulator represent display segment information for the character to be displayed. The most significant bit is used to illuminate the "pulse" light whenever a pulse detection is to be indicated. Whatever the value of the bit is at this time, it will be outputted again, but for the time being the most significant bit of the accumulator is cleared by the ANL instruction at line 551. The accumulator contents are then stored in the data memory location represented by register R1, namely, location 52 (DTBL)—the first in the display table. Register R1 is then incremented so that it points to the next location in the display table, and a return is made to the instruction at line 536.

A call is now made to the GCHARS routine once again. Since register R0 still represents the relative address in page 3 of the first two-character byte, the same two-character byte is stored in the accumulator and a return is made to line 537. This time, however, the two nibbles in the accumulator are not swapped because the second character to be displayed is represented in the four least significant bits. A call is made to the G2SEG subroutine which results in the segment byte for the second character being loaded in the next location in the display table, and register R1 is incremented so that it points to the third location in the display table.

At line 538, register R0 is incremented so that it points to the next byte (character pair) in the "CAL" message. A test is then made to see if six bytes (12 characters) have been processed. The contents of the AEX register are moved to the accumulator and, if the accumulator value is not zero, a jump is made to NCHAR (line 532). The value in the AEX memory location is decremented, and the DISP routine is executed once again. It is apparent that after 12 characters have been processed, the AEX value will be 0, and at line 541 a return will be made to line 119.

It should be noted that whenever DALPHA (line 506) is called, the F1 flag is cleared to represent that an alphabet character is to be displayed. Whenever digit values are to be displayed, as will be described below, the F1 flag is set and register R0 is loaded with the address BCD0, that is, the address of the location in data memory which contains the first two BCD digit offsets (or values, since each value is used as an offset to retrieve a segment byte). At line 547, a branch is made to line 549 (BCDSG) which simply results in the base relative address in page 3 for the digit segment bytes to be loaded in the accumulator, rather than the base relative address in page 3 for the alphabet character segment bytes. In this way, the same routine at line 549 can load digit segment bytes into the display table. Similarly, in the GCHARS subroutine at line 558, instead of loading the accumulator with a message character relative address, the branch at line 558 to line 562 causes the digits themselves (representing two offsets) to be loaded directly into the accumulator.

Referring back to line 116, it should be noted what is required to set up a new word message. Whenever a new message is to be displayed, the value DTBL is loaded into register R0, and the relative address in page 3 of the byte representing the first two characters is loaded into the accumulator. A call to DALPHA then results in storage in the data memory of the 12 display segment bytes for the message; the characters of the display are then refreshed automatically at 800-microsecond intervals as will be described below.

Thus far, however, the timer/counter has not been enabled. All that has been done is to store the number −10 in it (line 78). It is enabled at line 119, and at line 120 the timer counting is started. Since the number −10 is initially stored in the counter, the first timer interrupt occurs 800 microseconds after the timer is started.

The system proceeds to line 124, but it will be helpful at this point to digress and to consider what happens when a timer interrupt is generated. Timer interrupts, resulting from timer/counter overflows, always cause the program counter to be loaded with address 7 (line 87). The SEL RB1 instruction causes register bank 1 to be selected; it is this register bank which is used during the timer interrupt processing. The accumulator is saved in register R7′ (ASAV) in this register bank so that after the refreshing of a display character, normal processing can resume. The timer is then enabled for another 800-microsecond cycle by loading −10 in the accumulator and moving it to the timer/counter.

A call is then made to the SEGS subroutine at line 568. Every 800 microseconds, a single display character is refreshed. But the system does not maintain a record of the last character position which was refreshed. The position is actually represented and latched at port 2, bits 4–7, and these bits are examined to determine the next character which is to be refreshed (or changed, if since the last refreshing the display table contents were changed). At line 568, the eight bits latched at port 2 are read into the accumulator. It is the complement of the four most significant bits which represent one of the twelve character positions due to the provision of the inverters at port 2. It is for this reason that the accumulator contents are complemented at line 569. Because the four most significant bits represent the last character position which was refreshed, the two nibbles in the accumulator are swapped at line 570, to place the complemented four most significant bits latched at the port in the four least significant bits of the accumulator. By incrementing the accumulator at line 571, the next character position is determined.

The accumulator is then ANDed with the HEX digits OF so that only the least significant nibble remains in the accumulator, and the accumulator contents are stored in DIGSIV at line 573.

The decoder/driver has four input bits, and 12 outputs extended to the cathodes of the 12 display elements. Thus four of the sixteen possible input codes do not result in the driving of a respective one of the 12 output lines. In the particular chip used, codes 0, 2, 4 and 9 are not used. The least significant nibble in the accumulator was previously incremented to represent the next character position to be processed. If the accumulator was incremented to 0 (from 16), representing an unused code, the test at line 574 does not result in a branch to line 577. Instead, the address of the first location in the display table is stored in SEGPTR since it is this data memory location which contains the segment byte to be used. A jump is then made to line 583 (INCDIG). Since the first character position of the display is represented by the decoder code of 1, not 0, DIGSAV, which contains the number of the next character position to be refreshed, is incremented. Starting at line 584, the character position is refreshed, using the character code position in DIGSAV and the segment byte whose location is stored in SEGPTR. On the other hand, if the incremented code position in DIGSAV is not 0 at line 574, a test is made to see if it represents one of the three other invalid codes. At line 577, −2 is added to the accumulator. If the result is zero, indicating incrementing up to an invalid code of 2, a jump is made to line 583 where DIGSAV is incremented, following which the identified character position is refreshed. If the code position is not 2, then at line 579, −2 is added once again to the accumulator to see if the accumulator originally represented invalid code 4. If it did, a jump is made once again to line 583. Finally, by adding −5 to the accumulator at line 581, a test is made to see if the accumulator represented invalid code 9. If it did not, a jump is made directly to line 584; otherwise, DIGSAV is incremented, and only then is the SEGOUT routine executed.

Data memory location DIGSAV contains the character position to be operated upon in its four least significant bits, and its four most significant bits are 0. Because the character position is outputted at bits 4–7 of port 2, it is necessary to swap the two HEX digits stored in DIGSAV so that the position code is represented by the most significant nibble. At line 584, DIGSAV is placed in the accumulator, and the two nibbles are swapped at line 585. But the most significant bits of the accumulator now represent the actual position code, and due to the provision of the inverters at port 2, the actual code will be provided to the decoder/driver only if the complemented code is outputted at the port. For this reason, at line 586 the accumulator is complemented.

Referring to FIGS. 5 and 6, it will be noted that only four of the bits at port 2 control selection of a character position in the display. Bits 0, 1 and 2 are used as inputs, and when outputting a byte at port 2 it makes no difference which values are placed at the three pins used as inputs. But bit 3 of port 2 (pin 24 of the 8048 chip) is used as an output to control operation of the valve which opens the cuff to the atmosphere. Whatever the present value of this bit, it must not be changed when outputting a new character position for the decoder/driver.

At line 587, the accumulator contents are ANDed with the two HEX digits F7. This results in no change in all bits other than bit 3; this bit is cleared. The accumulator contents are then stored in DIGSAV. The routine now tests the value of bit 3 which is latched at port 2, and places this value in DIGSAV before outputting the byte at port 2. At line 589, the latched data bits at port 2 are loaded into the accumulator and at line 590 all of the bits are cleared except bit 3. This remaining bit is ORed with DIGSAV at line 591, and the new byte is outputted and latched at port 2 by the OUTL instruction at line 593.

But before this is actually done, an ORL instruction is executed at line 592. If the cathode of the new position in the display is energized while the seven least significant bits at port 1 still represent the respective states of the display segments for the previous character position, until the bit values at port 1 are actually changed the character represented at the position previously operated upon will actually be displayed at the new character position for a tiny fraction of a second, until a new display segment byte is outputted at port 1. To avoid this "bleeding" (which lasts for about 20 microseconds), all of the segment drivers are de-energized. They are de-energized only until a new cathode is selected, following which a new display segment byte is outputted at port 1.

There is one exception, however, and that relates to the most significant bit 7 at port 1. This bit is used to control the "pulse" light. Each digit or alphabet character requires the selective energization of seven segments, represented by the seven least significant bits in a respective location in the display table of the data memory. Other routines determine when the pulse light is to be illuminated, and when it is to be illuminated bit 7 of port 1 is forced low. Thus when causing the bit outputs at port 1 to go high momentarily to avoid "bleeding" (a bit output of 1 turns off a respective display segment), the bit value at pin 34 (bit 7 of port 1) should not be changed. At line 592, the two HEX digits 7F are ORed with the output bits at port 1. There is no change in the latched value a bit 7 of the port, but all of the other seven bits are latched to the 1 state. The inverters at the port outputs cause 0's to be applied to the seven segment lines, while the previously applied value appears on the line extended to the pulse light. Thus the light remains off if it was off, or on if it was on, but all seven segment lines are driven low. Thus even though the cathode of the next character position is selected before the new segment values appear at port 1, no display appears at this character position.

At line 594, the latched outputs at port 1 are loaded into the accumulator. (As described immediately above, seven of these outputs are now 1's.) At line 595, all bits are cleared, except the most significant bit which remains as it was. Register R0′ (SEGPTR) points to the address of the location in the display table which contains the segment byte to be outputted. At line 596, the display segment byte is ORed with the contents of the accumulator, so that the accumulator now represents the segments of the next character position which are to be energized, as well as a most significant bit which represents the state of the pulse light. The accumulator is then outputted at line 597 to port 1 to control both the pulse light and the refreshing of the new character position.

At line 598, SEGPTR is incremented so that it points to the next location in the display table (data memory locations 52–63). (SEGPTR is reset to the first location at line 575, as described above, whenever the first display position is to be operated upon.) At line 599, a return is made to the timer interrupt program at line 92.

It should be noted that because of the ORL instruction at line 596, a 1 may not be stored in bit 7 of any of the 12 locations in the display table. This would result in a 1 being outputted at bit 7 of port 1, and the permanent disablement of the pulse light. Consequently, a 0 must be stored in the most significant bit position in each of the 12 locations of the display table, and it is an examination of the pulse light latched bit (port 1, bit 7) which is the sole control over whether the light is pulsed again. A 0 is stored in the most significant bit position of every byte in the display table by making bit 7 of every segment byte, for both alphabet characters and digits, a 0. The most significant bit in each of ROM locations 300H–31FH is therefore a 0.

At line 92, the contents of data memory location AUX3 are moved to the accumulator. If the value is 0, at line 93 a jump is made to line 95. Otherwise, the value in AUX3 is decremented. As will be described below, AUX3 (having alternate label AUX33, depending on which register bank is the working bank) is used to time a 60-millisecond interval starting with the detection of a blood pressure pulse; if the pulse has a duration shorter than 60 milliseconds, it is "discarded". AUX3 is initially set, as will be described below, so that it is decremented down to 0 after 60 milliseconds. Once it reaches 0, the test at line 93 makes sure that it stays at 0. Thus when the pulse is over, a check can be made that it had a duration of at least 60 milliseconds simply by verifying that AUX3 is 0.

At line 95, data memory location AUX1 (register R5') is decremented and examined to see if it is 0. This register is used to time 100-millisecond intervals. If it is not 0, a jump is made to line 100. The timer flag was set at the end of the 800-microsecond timing cycle which caused the timer interrupt routine to be executed in the first place, and the JTF instruction resets it preparatory to another cycle of operation. A jump is made to the next line, TEXIT; the jump is not really required, but the JTF instruction is in order to reset the timer flag. Since the accumulator was originally saved at ASAV (register R7'), it is now restored, and lastly a return is made at line 102 to whatever instruction in the program would have been executed next had the timer interrupt not occurred. The RETR instruction is utilized at line 102 not only to return to the interrupted processing, but also to restore the program status word which is automatically saved in the stack provided for this purpose when the timer interrupt first occurs, and also to select bank 0 once again as the working register bank.

But if in line 95 AUX1 is decremented to 0, register R5' (AUX1) is loaded with a value of 125 at line 96. Since the value stored in AUX1 is decremented at line 95 once every 800 microseconds, it is apparent that it requires 100 milliseconds for AUX1 to be decremented from its initial count of 125 down to 0. By examining register R5', it is possible to determine when 100 milliseconds have elapsed, and this is actually done elsewhere in the program. Whenever 100 milliseconds have gone by, the contents of AUX2 are moved to the accumulator at line 97. As will be described below, this register (R6') is initially loaded with a value of 100 (when the third pulse is detected) so that the number of pulses which occur in a 10-second interval can be counted. With the value of AUX2 moved to the accumulator at line 97, the accumulator is examined at line 98 to see if it is 0. If it is, a jump is made to line 100. If it is not 0, AUX2 is decremented at line 99. By continuously examining the value of AUX2 (done elsewhere in the program), it is possible to determine when 10 seconds have elapsed. There is no need to reset AUX2 to its initial value of 100, because there is only one 10-second timing interval during each patient measurement. (Also as will now be described, a 1-second delay can be generated by loading AUX2 with 10, rather than 100, it thus requiring only 10 cyclings of register AUX1, or one second, before AUX2 is decremented down to 0.)

Returning to the main program, after the timer is enabled and started at lines 119 and 120, a call is made at line 124 to the WT1SEC routine at line 734. This subroutine simply delays things for one second, and allows the machine to settle down and the power supplies to come up. (During this delay, the calibrate, "CAL", message is displayed as described above.) The accumulator is loaded with the value 10 at line 734, and register R0 is then loaded with the RAM address of register R6' (AUX22). At line 736, the accumulator contents are transferred to AUX22. (Location AUX22, when running with register bank 0, as the system is now, is the same as memory location AUX2 when the system is running with register bank 1 during timer interrupt processing.) Consequently, as just described above, register R6' is decremented once every 100 milliseconds, and it is decremented down to 0 after one second has elapsed. At line 737, the contents of register R6' are moved to the accumulator. The accumulator is tested at line 738 to see if it has been decremented down to 0; if not, line 737 is executed again. The system simply remains in a wait loop for one second until register R6' has been decremented down to 0. When it has been, line 739 causes a return to line 125.

The INS instruction at line 125 transmits an $\overline{RD}$ pulse (approximately 1 microsecond in width) through the inverter connected to the "initiate conversion" input of the analog-to-digital converter. When this input of the 8704 chip goes high, a new conversion cycle begins, and the BUSY output goes high. The BUSY output goes low when the conversion is complete. The results of the previous conversion appear at the bit 0–9 output pins of the converter while a new conversion is in progress; the data is changed only at the end of a conversion when the BUSY line goes low. During normal processing, the 8048 chip examines its $\overline{INT}$ input (the converter's BUSY output) to see if a new sample is available. If it is, an IN instruction is executed to read in the two bits of the sample at port 2, followed by execution of an INS instruction to read in the other eight bits of the sample appearing at the BUS inputs. The microprocessor is so fast that when it is ready for another sample, one is not yet available; the microprocessor just waits and examines its $\overline{INT}$ input to see if the A/D converter has pulsed its BUSY line low. Thus the rate at which pressure samples are taken (approximately once every 2.5 milliseconds) is determined by the speed of the A/D converter.

At line 125, an input instruction is executed, by which the $\overline{RD}$ output pin is pulsed low and the data appearing on the BUS lines are stored in the accumulator. The first data sample is not actually used (nor are its two most significant bits even read in) since it is meaningless—the converter was never told to initiate a conversion until now. The reason for executing the INS instruction at line 125 is to initiate a conversion; although the INS instruction causes a data sample to be loaded into the accumulator (which sample is not used), it also initiates a new conversion due to the connection of the $\overline{RD}$ pin through an inverter to the "initiate conversion" input of the converter.

Figure 10:
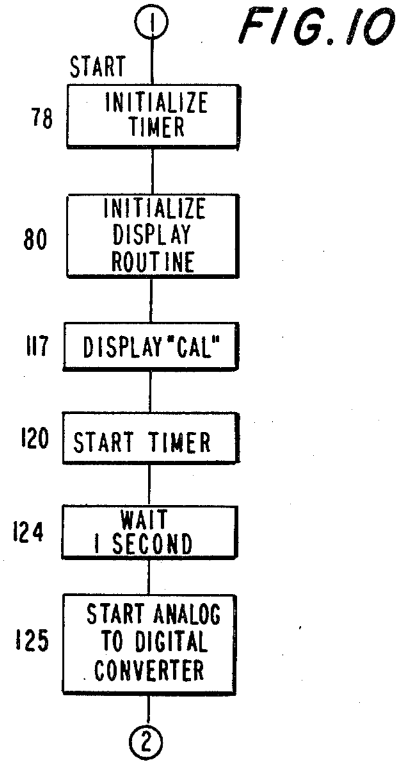
FIGS. 10-13, 15-18, 20, 23 and 24 are flow charts depicting most of the method of my invention, and should be read in conjunction with the complete source listing which is reproduced below and which will be described.

The start sequence described thus far is shown on the flow chart of FIG. 10. The flow chart depicts only the more important operations, with the number to the left of each block in the flow chart identifying the first respective line number in the source program. The flow chart does not depict the manner in which a new message is displayed, nor how the display is refreshed following timer interrupts, inasmuch as these routines have been described in detail.

Reference Pressure, Initial Battery Check, and Factory Calibrate

The system of the invention does not actually measure the instantaneous absolute pressure in the cuff. Were it to do so, the machine would have to be calibrated to provide a predetermined pressure reading when the cuff is at atmospheric pressure. But atmospheric pressure varies from location to location, for example, it is lower at higher elevations. Consequently, the system is designed to operate on relative pressures, not absolute pressures. While the cuff is open to the atmosphere, the system takes a reference pressure reading, PREF. As all digital samples have ten bits, two bytes are required to store PREF. The first byte is stored in register R2' and the second byte is stored in register R3' (see line 41). With the V1 valve open, the system looks at successive pressure readings to see if they are changing. As long as they are changing, it is an indication that the cuff was not originally at atmospheric pressure and air is either flowing into or out of it. PREF is constantly up-dated. As soon as the pressure readings cease to change, the latest up-dated PREF value is the final reference pressure. All other pressure readings are taken to be the difference between the actual sample outputted by the converter and the reference pressure. Thus no matter what the atmospheric pressure, each pressure sample which is actually processed is a pressure relative to atmospheric pressure. (PREF does not equal the atmospheric pressure due to the offset introduced by amplifier B of chip IC3 on FIG. 4. There is no need to know the atmospheric pressure, just the measured pressure when the cuff is at atmospheric pressure—since all samples processed are only relative values.)

During factory calibration, it is only necessary to insure that for some test pressures which exceed atmospheric pressure by a known amount, the readings taken represent the differences, and not the absolute pressures. There are several potentiometer adjustments which may be made to insure that when the cuff is open to the atmosphere the measured (relative) pressure is zero, and when a pressure of known value is in the cuff, the measured (relative) pressure is equal to the actual pressure minus atmospheric pressure.

After waiting for one second (line 124) and initiating a conversion (line 125), at line 126 a call is made to the REFP subroutine at line 914. A call is immediately made to the READPR subroutine at line 476. As described above, while a conversion is in progress, the BUSY output of the converter is high. This output is coupled to the $\overline{INT}$ input of the 8048 chip. The external interrupt is never enabled, and the $\overline{INT}$ input to the chip is tested to determine when a new sample is available. The JNI instruction at line 476 causes a jump to the GETP routine at line 478 if the $\overline{INT}$ input is low. Otherwise, the JMP instruction at line 477 simply causes the processor to remain in a wait loop, going back to the JNI instruction until the $\overline{INT}$ input goes low.

It will be noted that in FIG. 5 bits 0–7 of the converter are applied to the BUS inputs, while bits 8 and 9 are applied to bits 0 and 1 of port 2. It is these two latter bits which are first operated upon. The IN instruction at line 478 loads the accumulator with the bit values at port 2. (Ports 1 and 2 serve as both outputs and inputs; it is this property which allows latched outputs to be read in, as described above, and also allows input signals to override latched outputs if they are high. The original reset command causes the microprocessor to latch all of its port outputs high.) At line 479, the accumulator contents are ANDed with the HEX digits 03, thus clearing all digits except the two least significant which contain bits 8 and 9 of the converter output. The accumulator contents are then stored at AEX (register R2). The other eight bits are then read upon execution of the INS instruction, the eight least significant bits of the present sample appearing in the accumulator. (Execution of the INS instruction also starts another conversion.) Finally, the address of the PREF location in data memory is stored in register R0, and a return is made to line 915.

At this time a call is made to the DST subroutine at line 724. Since register R0 contains the address of location PREF, the least significant byte of the sample, now in the accumulator, is stored in location PREF. The XCH instruction then exchanges the least and most significant bytes, the most significant byte having been previously stored in location AEX at line 480. Register R0 is then incremented to point to the data memory location following PREF, and the most significant byte is stored at this location. Finally, the accumulator and AEX register contents are interchanged (to leave the two registers with their original contents), and register R0 is similarly decremented to restore its original contents. At line 730, a return is made to line 916, from which a return is made to line 730.

Figure 11:
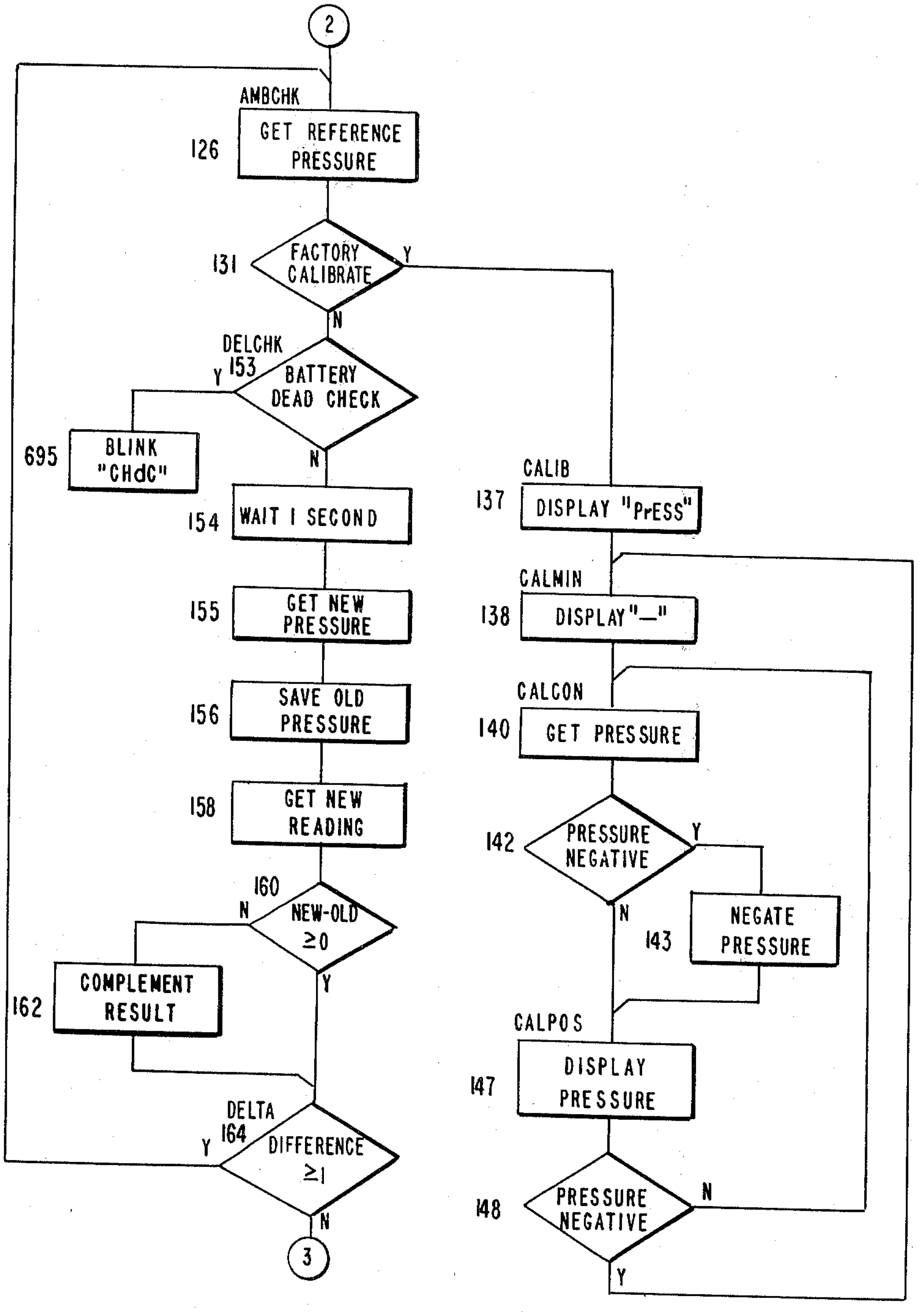

This operation is shown by the first block in the flow chart of FIG. 11, "get reference pressure". As will be described below, the reference pressure will be changed if the cuff is not originally at atmospheric pressure. But before this is done, the battery is checked to see if its potential is high enough for proper system operation.

The battery check is anything but straight-forward. The ROM program actually contains a sequence for testing whether the battery potential is both greater than 9.8 volts and less than 9.4 volts. Despite the fact that this is a physical impossibility, if this test condition is passed, a branch is made to a special subroutine. This special subroutine is one which allows the unit to be calibrated in the factory to provide accurate pressure readings. At the factory, a test clip is placed on the unit which forces the "impossible" test to be passed. A branch is then made to a "factory calibrate mode" routine which is only executed in the factory, and never executed when the unit is actually used in its normal mode. The ROM is actually shipped with a routine which is never executed during normal use. The routine is included in the program only to facilitate factory calibration. By including the routine in the program, however, factory calibration is greatly simplified.

Referring to FIGS. 3–5, the output of comparator A of chip IC10 is extended to the T1 input test pin of the microprocessor. Whenever the battery potential exceeds 9.8 volts, the output of the comparator is high; otherwise it is low. Similarly, the output of comparator B of chip IC10 is extended to bit 2 of port 2. During normal operation of the machine, the output of the comparator is high whenever the battery potential is greater than 9.4 volts, and it is low whenever the battery potential is less than 9.4 volts. It will be noted, however, that resistor R9 on FIG. 4, connected to the positive input of the comparator, can be connected to ground via a test clip in the factory. If the test clip connects the resistor to ground, the output of comparator B goes low even if the battery potential exceeds 9.4 volts. Thus a technician in the factory can force the "impossible" test to be passed—the battery potential exceeds 9.8 volts as reflected at the T1 input of the processor, and the battery potential is below 9.4 volts as reflected at bit 2 of port 2.

At line 130, the port 2 input bits are stored in the accumulator. The JB2 instruction tests bit 2 of the accumulator and thus in effect it examines the 9.4-volt test line. If the bit value is a 1, indicating that the battery potential exceeds 9.4 volts, the unit is in actual use by a patient and is not being factory calibrated. A jump is made to the DELCHK routine at line 153. As will be described below, starting here a check is made whether the battery is only partially charged (greater than 9.4 volts but less than 9.8 volts, allowing up to 25 additional measurements to be made before the battery goes "dead"). The DELCHK routine also makes sure that the cuff pressure is at atmospheric pressure before the final reference pressure (PREF) reading is assumed to be valid.

But if the test at line 131 indicates that the battery potential is below 9.4 volts, the test at line 132 is executed. The T1 input bit is examined; if it is low, indicating that the unit is not being calibrated in the factory (at which time the battery is fully charged), a jump is made to the DELCHK routine which then begins all over again to examine the state of the battery and to flash an appropriate message if necessary. But if the test at line 132 indicates that the battery potential exceeds 9.8 volts, and since the previous test which resulted in line 132 being executed in the first place indicated that the battery potential is also below 9.4 volts, it is an indication that the unit is being calibrated in the factory and the program advances to line 133. During factory calibration (which should not be confused with the automatic calibration which occurs every time the unit is turned on, or the reset key is depressed, i.e., the DELCHK routine), the valve within the unit which vents the cuff to the atmosphere (inside the housing) is closed. This allows the unit to be calibrated by maintaining known pressures in the cuff and insuring that the correct pressure values are displayed, as will be described below. When the system is first reset, to start a measurement sequence, the output ports are automatically latched high. Thus initially the valve is open because bit 3 of port 2 is high. To close the valve it is necessary to force this bit output low. The ANL instruction at line 133 closes the valve. Whatever the output latched at port 2, the ANL instruction clears bit 3. The low potential at bit 3 of port 2 (FIG. 5) which is now latched, is inverted, and then inverted once again by four inverter connected in parallel (to provide sufficient drive current for the valve coil, when needed). One end of the coil is connected to 9.6 volts, and the other is now grounded. The valve is normally open, but with a 0 at bit 3 of port 2, coil current flows and the valve closes.

At line 137, a call is made to the DPRESS subroutine at line 499. The instruction at line 499 loads the accumulator with the relative address in page 3 of the first byte (two characters) in the "PRESS" message. The program then proceeds with the DALPHA routine described above which actually results in the display of the selected message. As the unit measures the pressures in the cuff applied by the factory technician, he is informed that cuff pressure readings are being displayed. A return is then made to line 138. The three-digit pressure values are displayed in the last three character positions of the display. Just in case a minus sign is required, it is now displayed. (It is soon erased, if the pressure is not negative.) The address of the fourth from the last location in the display table is loaded into register R1, and at line 139 the HEX digits BF are stored at this location. These HEX digits cause a minus sign to be displayed when applied (through inverters) to the display segment drivers. The minus sign is displayed automatically, as every character or digit is when its respective segments are loaded into one of the twelve locations in the display table.

At line 140, a call is made to the READP subroutine at line 487. This subroutine simply calls the READPR subroutine (line 476) described above, which reads the latest pressure sample into AEX and the accumulator, and then stores the address of location PREF in register R0.

After lines 476–483 are executed, a return is made to line 491, PDIF. The sample value is now stored in PTMP and PTMP+1. At line 491, address PTMP is stored in register R0. The call to the DST subroutine (line 724) causes the sample value in AEX and the accumulator to be stored in two locations, the first of which is in register R0. The address of the first location containing the reference pressure, PREF, is then loaded into register R1, and a call is made to the DMINV subroutine at line 612.

This subroutine, between lines 612 and 632 is straightforward and will not be described in detail. The double-precision value pointed to by register R1 is subtracted from the double-precision value pointed to by register R0; no stored register (R0 and R1) values change, and the purpose of the subroutine is to set the carry flag and to store the difference in the accumulator and in AEX (with the least significant byte in the accumulator). In the present case, the carry flag is set if the difference between the just taken pressure value and the reference pressure value is zero or positive.

Lines 601–610 should be understood. When the DMINV subroutine is executed, the data (Y) pointed to by register R1 is subtracted from the data (X) pointed to by register R0. The binary difference appears in AEX and the accumulator. As for the carry bit, it is set to 1 if $X \geqq Y$; and it is set to 0 only if $Y \geqq X$. A call to DMINC (line 618) provides a similar result. In this case, instead of Y being data pointed to by register R1, the data in the accumulator and AEX are used when forming the difference X–Y. The DADDC subroutine (line 625) is similar to the DMINC subroutine but involves addition, not subtraction.

When a return is made to line 495, a jump is made to the DST subroutine at line 724. Since register R0 contains PTMP, the difference represented by the accumulator and AEX is stored in PTMP and PTMP+1. A return is then made to line 141.

The method of operation described thus far is as follows. PREF and PREF+1 have the reference pressure—which is atmospheric—as controlled by line 126. A sample value is then taken and temporarily stored at PTMP and PTMP+1. The reference pressure is then subtracted from this value, and the difference stored in PTMP and PTMP+1. It is the difference which is displayed, and the difference is the actual sample value less the reference pressure.

At line 141, flag F0 is cleared. This flag is cleared for (PTMP–PREF) pressure values which are positive, and it is assumed that the value is positive. If it is, the carry bit was set by the DMINV subroutine and at line 142 a jump is made to line 147 which actually controls the display of the pressure value.

If the pressure is negative, the program advances to line 143. First, flag F0 is set by complementing it, to indicate a negative pressure. A call is then made to the DADDC subroutine at line 625. The double-precision value pointed to by register R0 is added to the double-precision value contained in AEX and the accumulator. Since register R0 points to PTMP, and locations PTMP and PTMP+1 contain the difference pressure still stored in AEX and the accumulator, twice the difference (a negative value) is formed.

At line 145, the DMINC subroutine is called. This subroutine forms the difference between the double-precision value pointed to by register R0 and the contents of AEX and the accumulator. In the present case, the net result is that the original negative pressure value is negated. The call to DST at line 146 then causes the negated pressure value (now positive) to be stored in PTMP and PTMP+1.

At line 147, a call is made to the DSPRES subroutine at line 514 in order to display a pressure value. The system resolution is 0.5 mm Hg, that is, if a pressure sample, minus the reference pressure, is X, then the stored value is 2X. To display the contents of PTMP and PTMP+1, the value must be halved, and then converted to BCD form in order to recess digit segment bytes.

After loading register R0 with the PTMP address, at line 515 the BINBCD subroutine is called (line 639). Digits are displayed in groups of three; location BCDO must contain a code representing a blank (BH) followed by the code of the most significant BCD digit to be displayed, and location BCD1 must contain the two least significant BCD digit codes to be displayed. Address BCD0 is first loaded into register R1 at line 639.

Registers R0 and R1 are then incremented so that they point respectively to locations PTMP+1 and BCD1. The carry flag is cleared (preparatory to the ensuing operations), and the byte pointed to by register R0 (the most significant PTMP pressure byte) is placed in the accumulator, shifted one bit position to the right through the carry flag, and then stored in the location BCD1 (which follows location BCD0 in the data memory). Registers R0 and R1 are then decremented to point to PTMP and BCD0, and at line 651 PTMP is loaded into the accumulator. The right shift starting at line 652 causes any bit shifted to the right from the earlier shift of the most significant (PTMP+1) pressure byte to be shifted into the most significant bit position of the least significant byte (PTMP). The net result is that the 2-byte PTMP pressure value is halved by shifting it to the right, and it is transferred from PTMP and PTMP+1 to BCD0 and BCD1. The resolution of the system is 0.5 mm Hg, and the shifting procedure provides the actual pressure (in binary form).

The maximum sample value of 10 bits is 1024. When halved, this gives a maximum value of 512. Thus three BCD digits must be formed. The binary to BCD conversion method between lines 657 and 681 is well known. First, increments of 100 are subtracted from the 9-bit binary value until the result would be negative. The number of increments which leave a positive value (under 100) is the first BCD digit, stored in the least significant nibble of BCD0. (The most significant nibble is loaded with the HEX code representing a blank. The least significant nibble is loaded with 0 if the pressure value being operated upon is less than 100.) In a similar manner, by subtracting increments of 10 from successive remainders until the final remainder is between 0 and 9, the tens digit can be determined and stored in the most significant nibble of BCD1. Finally, the remainder—the units digit—is stored in the least significant nibble of BCD1. A return is then made to line 516.

As described above, the DISP routine stores any message, or message part, in the display table. The set-up for calling the routine is as follows: (1) AEX must represent the number of characters (alphabet or digit) to be placed in the display table; since two characters are processed for each message or double-BCD byte, and AEX is decremented only after bytes are processed, AEX must have a value of 1 to process four BCD digits. (2) Register R0 must contain either the first message relative address, or for digits the value BCD0. (3) Register R1 must contain the position of the first character to be placed in the display table, in this case DTBL+8, the fourth position from the end. (4) Flag F1 must be cleared to display alphabet character messages, and it must be set to 1 to display digits.

When the system returns to line 516 the address DTBL+8 is loaded into the accumulator. The DBCD routine at line 523 then establishes the four set-up conditions. Registers AEX, R0 and R1 are loaded as required in lines 523–525, and in lines 526 and 527 flag F1 is set. At line 528 a jump is made to the DISP subroutine at line 533. The rest is automatic; the digit segment bytes are loaded in the display table and the display is updated automatically during the timer interrupt routine.

After the message is up-dated, a return is made to line 148. There are actually four digit segment bytes which are loaded into the display table but the first, at location DTBL+8, represents a blank. If the pressure value is negative, however, a minus sign should be displayed at the display position corresponding to display table address DTBL+8. A minus sign segment byte was originally stored at address DTBL+8 at lines 138 and 139, but it has been erased. A test is made at line 148 to see if the pressure is negative. If flag F0 is set, indicating a negative pressure, a jump is made to line 138 so that the minus sign is displayed. Otherwise, a jump is made at line 149 to line 140 where the process repeats itself but without a minus sign being substituted for the blank.

It is thus apparent that during factory calibration, whatever pressure the technician applies to the cuff appears on the display. Two potentiometers (coarse and fine) are provided as an offset control (FIG. 4). These potentiometers are adjusted so that a pressure of 0 is displayed when the applied pressure equals atmospheric pressure (cuff open to atmosphere, i.e., bulb removed). The cuff tubing may then be connected to an accurate manometer, and to a bulb without a bleed hole. When the bulb is pumped to apply a pressure of 200 mm Hg (as registered on the manometer) to the cuff, for example, the two gain potentiometers (coarse and fine) are adjusted until a reading of 200 is obtained. With the system calibrated properly for relative pressures at 50 mm increments from 0 to 300 mm, it can be assumed that it will operate properly over the entire range. The unit remains in the factory calibrate mode and simply continues to display the cuff pressure. To exit the loop, the technician presses the reset button, if desired, in order to restart the machine and further test it.

As described above, the program jumps to line 153 when the unit is actually being used by a patient, at which time the battery is checked and the reference pressure is changed if necessary. A call is first made to the BDEAD routine at line 693. The IN and JB2 instructions test bit 2 of port 2. If this bit is a 1, indicating that the battery potential is above 9.4 volts, a return is made to line 154. But if the bit value is a 0, indicating that the battery is dead, the instruction at line 695 is executed. The accumulator is loaded with the relative address in page 3 which contains the "CH dC" message, i.e., the unit cannot be used because the battery needs recharging. A call is then made to the BLINK subroutine at line 685. A call is immediately made to the BLINK1 subroutine at line 687, which in turn calls the DALPHA subroutine to control display of the message. The accumulator is then loaded with the number 3 and a jump is made to the WAIT subroutine at line 735. Referring to line 734, it will be recalled that when the accumulator is loaded with the number 10, a 1-second delay is generated. With the accumulator now loaded with the number 3 and the jump being made to line 735, a 0.3-second delay is generated. When the RET instruction is executed at line 739, a return is made to line 686. The accumulator is now loaded with the relative address in page 3 of the location containing the first two characters of a "blank" message, and a call is then made to the DALPHA subroutine. After the return from this subroutine and another execution of the WAIT (0.3-second) subroutine, a return is made to line 697, which immediately causes a jump to the line (695) which started the whole process. In this way, the "CH dC" message is displayed for 0.3 seconds, following which the display is blanked for 0.3 seconds. The cycle is self-repeating, and the system remains in an endless loop with no measurements being possible. The user must recharge the battery in order to further utilize the unit.

If the battery is not dead, the call at line 154 controls a delay of one second to allow the cuff pressure to settle down to atmospheric pressure. (The valve is still open, as it has been since reset; line 133 is executed to close the valve only during factory calibration.) Then the reference pressure stored in PREF and PREF+1 (line 126) is corrected if necessary; this is accomplished before the system checks whether the battery potential is above 9.8 volts or below it (but above 9.4 volts—which must be the case if line 155 is reached).

At line 155 the pressure is read. The called READP subroutine at line 487 calls the READPR subroutine which stores the pressure sample in PTMP and PTMP+1, with register R0 pointing to PTMP. The PDIF routine at line 491 then replaces the pressure sample in PTMP and PTMP+1 by the relative pressure (sample value less reference value). When a return is made to line 156, the address of PLAST is loaded into register R1. A call is then made to the DMOVE subroutine at line 902. This subroutine (lines 902–910) causes the contents of the 2-byte location pointed to by register R0 to be loaded into the 2-byte location pointed to by register R1, with no change in the values stored in the pointer registers. In this case, the sample value just taken and stored in PTMP and PTMP+1 is loaded into PLAST and PLAST+1.

At line 158, another pressure sample is taken and loaded into PTMP and PTMP+1. A test is now performed to see if the two samples differ. Register R1 is made to point to PLAST; register R0 still points to PTMP. Thus the call to DMINV forms the difference between the two sample values. If the difference is zero or positive, the carry flag is set, and at line 161 a jump is made to line 164. Otherwise, the difference in the accumulator (the difference is small so the two most significant bits in AEX can be ignored) is negated by the CPL and INC instructions. In either case, the test at lines 164 and 165 is executed, working with a positive value contained in the accumulator.

The test is simply to see if the two samples were the same to within 1 mm Hg. The accumulator contains a positive value no matter what the sign of the actual difference. A 1 mm Hg difference is represented by a value of 2 since each sample value is twice the actual pressure. Therefore, at line 164, −2 is added to the accumulator. In HEX notation, and using 2's complement arithmetic (since that is what the assembler does), −2 is translated to FEH. If the accumulator contains a value of 0 or 1 (00H or 01H), corresponding to a pressure difference of 0 or 0.5 mm Hg, the addition of −2 to the accumulator gives a result of FEH or FFH, and the carry bit is not set. The cuff pressure therefore changed by less than 1 mm Hg between the last two samples, it is assumed that the cuff pressure is at atmospheric pressure, the reference pressure value (at PREF and PREF+1) is correct, and the JC instruction at line 165 causes processing to proceed at line 170. But if the difference exceeds 1 mm Hg, the cuff pressure is not yet at atmospheric pressure, the ADD instruction at line 164 sets the carry flag, and the JC instruction at line 165 causes a branch to be made to line 126, at which time a new reference pressure reading is taken. Because the valve is open, utlimately the cuff pressure will be at atmospheric pressure, there will be less than a 1 mm Hg change in successive pressure samples, and processing will proceed to line 170.

FIG. 11 is the flow chart depicting in broad outline the processing involved during the initial battery check, the factory calibration procedure, and the derivation of reference pressure.

Pump-Up of Cuff

The operator is informed to press the recall/cuff key by one of two messages. The usual message is "CUFF". However, if the battery potential is low, but not that low such that a measurement may not be taken, the message which is displayed is "LO dC". The latter message means the same thing as "CUFF", but it further informs the operator that the battery should be recharged.

It should be noted that the "CAL" message is displayed for at least two seconds, due to the two 1-second delays called for by lines 124 and 154. This message may actually be displayed for a longer period of time if the cuff pressure has to bleed down (e.g., if one measurement is taken soon after another, and the cuff did not reach atmospheric pressure following the first measurement and before the second was begun), the delay being introduced due to the checking of successive pressure measurements against each other until the difference represents a pressure drop of less than 1 mm Hg.

At line 170, the relative address in page 3 of the "CUFF" message is loaded into the accumulator, preparatory to a call of the DALPHA subroutine at line 173, at which time the "CUFF" message is displayed. However, at line 171 the battery voltage is tested. If the T1 test input is high in potential, it is an indication that the battery voltage exceeds 9.8 volts, a jump is made to line 173, and the "CUFF" message is displayed. But if the battery voltage is less than 9.8 volts (it is already known that it is greater than 9.4 volts or else line 170 would not have been reached), at line 172 the relative address in page 3 of the "LO dC" message is loaded into the accumulator. It is then this message which is displayed when line 173 is executed.

At line 177, the BDEAD subroutine is called to check the battery. If the battery is dead (below 9.4 volts), the measurement sequence is aborted, and the operator is informed by a blinking "CH dC" message that the unit may not be used. The reason for checking the battery—not only at line 177, but also repeatedly during subsequent processing—is that nickel cadmium batteries are prone to exhibit a potential which indicates that they are fully charged despite the fact that they may not be. Sometimes, it is only as current is drawn that the potential drops to indicate the true condition. It is for this reason that the batteries are repeatedly checked.

At line 178, the READP subroutine is called. This is the basic subroutine which forms the difference PTMP-PREF in AEX and the accumulator, as well as storing it in the two locations PTMP and PTMP+1.

When the difference is formed, the carry bit is set if the cuff pressure (PTMP) is greater than or equal to the reference pressure. If the carry bit is not set, that is, the actual cuff pressure is less than the reference pressure, than the JNC test at line 179 controls a jump to line 187. This condition arises if there is still a slight decay in the cuff pressure (even though the earilier cuff pressure test verified that between two successive samples the decay was less than 1 mm Hg), and another up-dated reference pressure reading is taken soon since the cuff pressure had dropped. The JT0 instruction at the line 187 tests whether the operator has pressed the recall/cuff key. If he has not, a jump is made back to line 177 where the cycle is repeated. Eventually, when the recall/cuff key is operated, the system advances to line 188. The REFP subroutine is called in order to derive a new reference pressure (PREF) value. At line 189, the ANL instruction causes the valve in the housing to be closed, and the next two instructions cause the "OCCLUdE" message to be displayed; this is an indication to the operator that he should start pumping the bulb.

Figure 12:
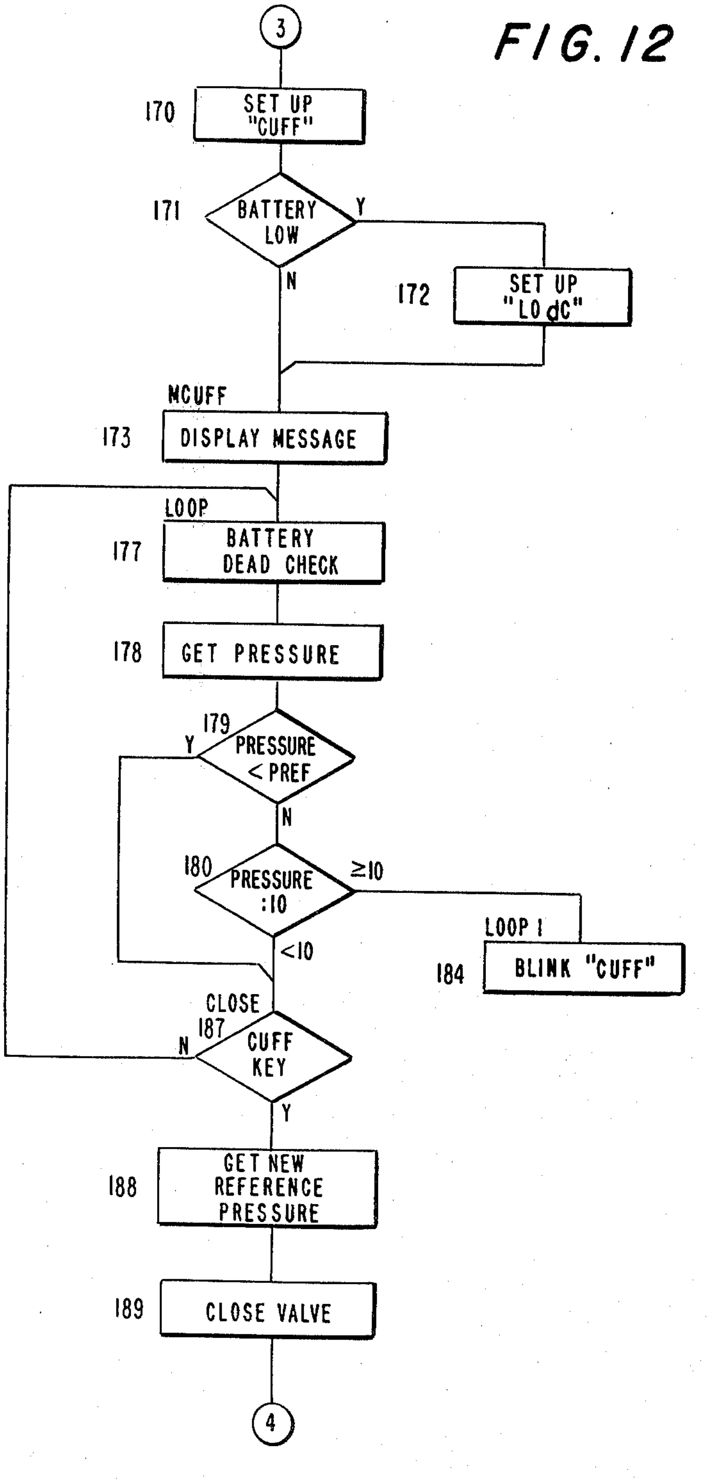

The above description assumes that the JNC instruction at line 179 causes a jump to line 187. But if the carry bit is set following the taking of a pressure sample at line 178, it is an indication that the cuff pressure is greater than the reference pressure. The operator is supposed to press the recall/cuff key after the "CUFF" or "LO dC" message is displayed, and he is supposed to pump the bulb only after the key is operated, i.e., when the "OCCLUdE" message is displayed. The system checks whether the operator pumped the bulb without first pressing the recall/cuff key by examining the cuff pressure. Alternatively, a pressure rise may have resulted if the patient moved his arm and in the process squeezed the cuff. In either case, if the pressure rise is at least 10 mm Hg, the measurement cycle is aborted. At lines 180 and 181, the value 20, representing a cuff pressure of 10 mm Hg, is loaded into the accumulator and AEX. The double precision subtract operation called for at line 182 compares the value of the last sample taken with the threshold of 10 mm Hg. (The DMINC subroutine requires register R0 to point to the minuend, and in this case it points to PTMP as a result of the execution of the READP subroutine at line 178.) If the subtract routine does not result in the setting of the carry bit, it is an indication that the latest sample value is less than 10 mm Hg, and a jump is made at line 183 to line 187; the system simply waits for the operator to press the recall-/cuff key, and the "OCCLUdE" message is then displayed. But if the latest sample value is equal to or greater than 10 mm Hg, a branch is not made at line 183 and instead the instruction at line 184 is executed. The relative address in page 3 of the "CUFF" message is loaded into the accumulator, and the BLINK subroutine is then called. This subroutine causes the "CUFF" message to be displayed for 0.3 seconds, following which the display is blanked for 0.3 seconds. The JMP instruction at line 186 then causes the blinking "CUFF" message to be repeated. The blinking message informs the operator that the measurement cannot be continued because the operator pumped the bulb before pressing the recall/cuff key, or the patient moved his arm. In order to take a measurement, the reset key must be operated and the whole process repeated from the start. It should be noted that in case the battery potential is less than 9.8 volts, the original message which is displayed is "LO dC". But if the measurement process is to be aborted, it is the "CUFF" message which starts to blink. The sequence just described is shown on the flow chart of FIG. 12, and at the top of the flow chart of FIG. 13.

At the start of the pumping, and until the pressure in the cuff exceeds 40 mm Hg, the "OCCLUdE" message remains on the display; the cuff pressure value is not displayed. This sequence is controlled by the instructions at lines 195-201. First, a cuff pressure sample is taken. If the carry bit is not set, it is an indication that the reference pressure exceeds the sample pressure, i.e., the bulb has not been pumped and there is still a small bleed of air from the cuff (not through the valve in the housing which is now closed, but rather through the bulb bleed hole). Alternatively, the carry bit may not be set as a result of a quantizing error. In either case, the system remains in a loop consisting of lines 195 and 196. But as soon as the bulb has been pumped and the pressure in the cuff rises, the processing proceeds to line 197. AEX and the accumulator are loaded with a value which represents a pressure of 40 mm Hg. The call to the DMINC routine in effect compares the pressure sample with the 40 mm Hg threshold, and sets the carry bit if the pressure sample is greater than or equal to 40 mm Hg. If it is not, the JNC instruction at line 200 causes the system to jump back to line 195 and the cycle repeats itself.

Eventually, when the cuff pressure rises to at least 40 mm Hg, the HEX value FF is loaded in data memory location COUNT. Ordinarily, this location is used to maintain a pulse count as will be described below, but it is now used for another purpose. It is used as a flag to indicate when the "PrESS" (pressure) message should be displayed, as will become apparent below. The non-zero value stored in COUNT at line 201 is simply an indication that the cuff pressure exceeds 40 mm Hg, and that the "PrESS" message should be formed and displayed together with cuff pressure values as the pumping continues. The message which is displayed is of the form "PrESS 123". COUNT serves as a flag to indicate that the message should be formed; it is not yet displayed, however.

FIG. 14 depicts the cuff pressure (not drawn to scale) during pump-up, followed by a decreasing occluding pressure with superimposed blood pressure pulses. The pump-up is characterized by a usually large rise in pressure to a relative peak each time the bulb is squeezed, followed by a gradual drop in pressure as the air in the cuff bleeds out until the bulb is squeezed once again. Eventually a maximum peak is reached, after which the pressure falls down until blood pressure pulses appear when the cuff pressure reaches the systolic pressure. It should be understood that the left side of the curve of FIG. 14 should also show blood pressure pulses until the cuff pressure is sufficient to completely occlude the artery. However, for the sake of clarity and in order to make the system operation more understandable, these pulses are not shown on the left side of the drawing.

For a valid systolic pressure measurement to be taken, it is necessary that the artery first be completely occluded, and that only as the cuff pressure bleeds down do blood pressure pulses start appearing. Thus the basic test which the system performs is to measure a 2.5-second time interval after the peak cuff pressure is reached, and to verify that no blood pressure pulses are detected during this interval. Theoretically, this means that as the cuff pressure continuously decreases, there are no instantaneous pressure increases for at least 2.5 seconds. But there are often small pressure "rises" even if the artery is occluded. For example, the analog-to-digital converter may make a quantizing error, corresponding to 0.5 mm Hg; such a small pressure rise is not enough to indicate a non-occluding condition. For this reason, as the pressure decreases from the peak, every pressure rise is measured. After 2.5 seconds have elapsed without any pressure rise reaching 1.0 mm Hg, it is assumed that the artery has been occluded for 2.5 seconds.

The picture is complicated, however, because there is no way to tell in advance when the highest peak has been reached. A relative peak is reached each time the bulb is squeezed, and this peak is the maximum only if the bulb is not pumped again.

The drawing of FIG. 14 shows two relative peak pressures on the left side, each following a pumping of the bulb and being followed by a pressure decrease until the bulb is pumped once again. It is only after the absolute peak is reached that there are no longer any pressure rises due to pumping. What the system does is to repeatedly take pressure sample values (PTMP) at approximately 2.5-millisecond intervals. (As described above, each sample is a relative pressure value—the cuff pressure minus the reference pressure.) The system maintains a relative maximum pressure value PMAX, the highest cuff pressure reached thus far during the pumping. When the bulb is squeezed, in the usual case the instantaneous pressure will rise above the current PMAX value, and the latest PTMP sample is then used as the new PMAX value. Such a PMAX value is shown on the drawing.

As the pressure then starts to decrease, a relative minimum value, PMIN, is formed. Each new PTMP sample, if less than the current PMIN value, is used to up-date PMIN, since a new relative minimum (below PMAX) has been reached. If the pressure rises for any reason (but stays below PMAX)—as a result of a pulse, or even due to a quantizing error—PMIN is subtracted from the sample value (PTMP). The difference (H in FIG. 14) represents a pressure increase in the cuff. It is ignored if it is less than 1 mm Hg. If it is at least 1 mm Hg, a pulse is presumed to be in progress. If the duration of the pulse is less than 60 milliseconds, it is similarly ignored. Pulses which are too weak or too short are not considered to be valid.

Whenever a new PMAX value is detected, the 2.5-second timing interval is started—just in case the absolute peak pressure has been reached and the artery is occluded. If the absolute peak has been reached, during the next 2.5 seconds successive PTMP samples will be decreasing (rises of less than 1 mm Hg and pulses shorter than 60 milliseconds are ignored). If the samples are decreasing in this manner, the systolic pressure measurement may begin.

But whenever PTMP rises to or above PMAX (e.g., upon pumping the bulb), the 2.5-second timing interval must begin all over again. Furthermore, if PTMP does not rise above PMAX but a legitimate pulse is detected, a "LO OCC PrESS" message is displayed to inform the operator to pump up the bulb.

Starting at line 205, PMAX and PMIN are both set to the last pressure sample value, PTMP. This is accomplished by the two set-up instructions at lines 205 and 207, and the two double-precision DMOVE calls at lines 206 and 208. (The DMOVE subroutine requires R0 to point to location PTMP in this case, and it does as a result of the calling of the READP subroutine at line 195.) Whenever a new peak pressure is detected, both PMAX and PMIN are set to it by jumping to line 205, and initially—as soon as a pressure of at least 40 mm Hg is detected—the system treats the condition as though a new peak value was just detected. At lines 209 and 210, AUX22 is loaded with the value 25, in order to initiate a 2.5-second timing interval. Location AUX11 is not set with a value of 125 which it should be for a precise 2.5-second interval to be measured (see timer interrupt subroutine starting at line 85). If location AUX11 initially contains a count close to zero, only a 2.4-second interval will be measured. However, this is of no moment because the absence of blood pressure pulses for 2.4 seconds is an adequate indication that the artery has been fully occluded.

At line 211, flag F0 is cleared, i.e., set to 0. This is an indication that a blood pressure pulse has not been detected yet. Whenever PTMP equals or exceeds PMAX, not only are PMAX and PMIN set to PTMP, but flag F0 is also initialized.

If the cuff pressure exceeds 250 mm Hg, there is no reason for further pumping (unless it is known that the patient has a higher systolic pressure). For this reason, if the pressure in the cuff exceeds 250 mm Hg, the "HI OCC PrESS" message is displayed to inform the patient or the physician that the cuff pressure is high enough and that further pumping is not necessary. (If the bulb is nevertheless pumped further, it has no effect on the system operation.) Toward this end, at lines 212 and 213, AEX is loaded with a value of 1 and the accumulator is loaded with a value of 244, together representing a value of 500, corresponding to a pressure of 250 mm Hg. Since register R0 still points to PTMP, the call to the DMINC subroutine at line 214 forms the difference between PTMP and the value 500. If the carry bit is not set, it is an indication that the cuff pressure has not reached 250 mm Hg, and a branch is made to line 220. On the other hand, if the cuff pressure equals or exceeds 250 mm Hg, the instructions at line 216 and 217 cause the "HI OCC PrESS" message to be displayed. At line 218, COUNT is set to the HEX value FF to indicate that the "PrESS" message is not yet displayed. Although COUNT was set in the same way at line 201, as will become apparent below, jumps may be made back to line 205, 209, 211 or 212, and COUNT may be 0. So it is now set to FF to indicate that the "PrESS" message is not on. A jump is then made from line 219 to line 225. (By thus skipping the instruction at line 224, a pressure value is not displayed, as will become apparent below; only the "PrESS" message is accompanied by pressure values.)

If the latest sample does not indicate a pressure as high as 250 mm Hg, a branch is made from line 215 to line 220. The COUNT flag is loaded in the accumulator and examined to see if it is 0. If it is, it is an indication that the "PrESS" message is on and a jump is made to line 224. If the "PrESS" message has not been displayed, it now will be and at line 222 COUNT is set to 0. The call at line 223 to the DPRESS subroutine then causes the "PrESS" message to be displayed, followed by the display of the current sample value under control of the call to the DSPRES subroutine at line 224. Whether the "PrESS" message with a sample value is displayed, or "HI OCC PrESS" is displayed, the instruction at line 225 is executed.

A new pressure sample is taken at line 225, and a threshold value representing 35 mm Hg is loaded into the accumulator and AEX at lines 226 and 227. The instructions at lines 228 and 229 cause a jump to line 190 if the cuff pressure is less than 35 mm Hg—in such a case, the patient or the physician has allowed the cuff pressure to bleed all the way down and the "OC-CLUdE" message is displayed rather than the "PrESS" message together with a pressure value. The whole cycle starts all over again. But if the pressure has not dropped below 35 mm Hg, the instruction at line 233 is executed.

The instructions at lines 233 and 234 compare the latest sample value, PTMP, with the most recent PMAX value. As soon as the lastest pressure sample equals or is greater than PMAX, a jump is made to line 205 where PMAX and PMIN are set to PTMP, flag F0 is set to 0, and the timer is reset. But if PTMP does not exceed the most recent PMAX value, the instruction at line 236 is executed; register R1 is made to point to PMIN. Since register R0 still points to PTMP as a result of the READP subroutine having been executed (line 225), the difference PTMP-PMIN is formed at line 237. If the carry bit is not set, it is an indication that PTMP is less than the current value of PMIN. The cuff pressure is decreasing and a new PMIN value is required; a jump is made to line 246. The latest PTMP sample is stored in PMIN when the DMOVE subroutine is called.

On the other hand, if the test at line 238 indicates that PTMP is not less than PMIN, it is an indication that the pressure has remained the same or increased to a value above the current PMIN. Flag F0 is tested at line 239. If it is a 1, indicating that a pulse is in progress, a jump is made to line 212; since PTMP is between PMAX and PMIN if line 239 is reached in the first place, no initialization is required and processing begins again from a point just after the initialization steps. But if a pulse has just been detected (PTMP-PMIN$<$0 at line 238, and flag F0$=$0 at line 239), the amplitude of the pulse is checked; if it is less than 1 mm Hg, it is ignored as not representing a true pulse. The accumulator contains the amplitude (PTMP-PMIN) as a result of the execution of the instruction at line 237. (Although the most significant bits of (PTMP-PMIN) are in AEX, they must be 0 since PTMP did not exceed PMAX, and they can be disregarded.) The value $-2$ is added to the accumulator at line 240. If bit 7 of the accumulator is now set, it is an indication that the amplitude is less than 2, i.e., less than 1 mm Hg; the JB7 test at line 241 causes a jump to be made to line 212. In effect, the "pulse" is ignored because it is too small to be legitimate. But if bit 7 of the accumulator is a 0, indicating that a legitimate pulse has just been detected, flag F0 is complemented from 0 to 1 at line 242.

With the detection of the pulse, a 60-millisecond timer is started. At lines 243 and 244, AUX33 is loaded with the value 75. Since the timer interrupt routine decrements AUX33 every 800 microseconds, it takes 60 milliseconds for AUX33 to be decremented down to 0. Following setting of the timer, a jump is made back to line 212 for the taking of further samples.

Thus low-magnitude artifacts are ignored, and large sample values (PTMP$\geq$PMAX) reset the 2.5-second timer. The only situation left to consider is a blood pressure pulse whose peak value does not reach PMAX. Eventually a sample is taken whose value is less than PMIN, at line 238 a jump is made to line 246, and at line 246 PMIN is set equal to PTMP. But line 246 can also be reached if a pulse was not in progress, i.e., the cuff pressure is simply bleeding down and PTMP is less than the previous PMIN. At line 246, PMIN is set to the new lower PTMP, but subsequent processing is different for the two cases.

In both cases, at line 247 register R1 is made to point to AUX33. The test at line 248 then distinguishes between the two cases. Flag F0 is tested. If it is a 1, indicating that a pulse was in progress, a jump is made to line 250. The value of AUX33 is loaded into the accumulator, and at line 251 a check is made to see if it is 0, i.e., if 60 milliseconds have gone by since the pulse started. If they have, a jump is made to line 259. A pulse whose width is at least 60 milliseconds is a legitimate pulse. The fact that it was detected means that the artery is not fully occluded, and additional pumping is required. At lines 260 and 261, the "LO OCC PrESS" message is displayed to indicate that the occluding pressure is loo low. Before that, at line 259, COUNT is set to its non-zero value simply to flag the fact that the "PrESS" message is not being displayed.

At line 265 another pressure sample is taken, and at lines 266 and 267 it is compared with the current value of PMAX. If the new pressure sample is less than PMAX, it is an indication that the patient is allowing the cuff pressure to bleed down. At line 268 a jump is made back to line 265, and the system simply remains in a loop with the "LO OCC PrESS" message being displayed. If the patient does nothing, the cuff pressure will bleed all the way down and the message will not change until pumping is started. On the other hand, as soon as the bulb is pumped and PTMP equals or exceeds PMAX, the instruction at line 269 is executed. A jump is made back to line 209 which restarts the 2.5-second timer. Not only is the timer restarted, but flag F0 is cleared since it is not yet known that a pulse is in progress. (PMAX and PMIN are not initialized at lines 205–208 but this is of no moment. PMAX is so low anyway that eventually PTMP will exceed it and a jump will be made back to line 205.)

Line 252 is reached if either a pulse was not in progress (the test at line 248 showed that F0 was 0), or a pulse of less than 60 milliseconds in duration was detected (the test at line 251 showed that the 60-millisecond timer did not time out)—the latter case also being treated as though a pulse was not in progress. A check is now made to see if the 2.5-second timer has timed out. The value of AUX22 is loaded into the accumulator at lines 252 and 253, and tested at line 254. If it is not 0, at line 254 the JNZ instruction causes a jump to line 211. Since the cuff pressure is bleeding down, no initialization is required. But if 2.5 seconds have gone by without a pulse having been detected, at line 255 a jump is made to line 274, at which time systolic pressure processing begins.

The reason for using COUNT as a flag to indicate whether "PrESS" is displayed is to avoid repeatedly resetting the message (see lines 220–223)—for two reasons. First, setting the message takes time and might delay the taking of samples. Second, setting the "PrESS" message blanks out all positions except the first five—including the pressure value. Although the pressure value is soon re-displayed, flicker of the display would otherwise result. It is avoided by not resetting the "PrESS" message if it is already displayed.

Prior to initiating the systolic pressure measurement, AUX22 is loaded with the value 255 at line 274. (Register R1 still points to AUX22 as a result of the execution of the instruction at line 252). AUX22 is simply loaded with a high value at this time, although the precise value is not important. This location is used to count down a 10-second period, but the timing interval is not to begin yet. To avoid an inadvertent time-out, the counter is initially set with an arbitrarily high value. It should also be noted that in the event the cuff was pumped up to a pressure exceeding 250 mm Hg, the "HI OCC PrESS" message was displayed. As long as the pressure exceeds 250 mm Hg, the test starting at line 212 not only causes the message to remain on the display, but at line 219 a jump is made to line 225 without a pressure value being displayed by execution of the instruction at line 224. Now that 2.5 seconds have expired without a blood pressure pulse having been detected, the cuff occluding pressure will start to decrease and systolic pressure measurements will begin. As the cuff pressure decreases, the system displays the instantaneous pressure—together with the message "PrESS". For this reason, at line 275 the "PrESS" message is displayed in the event it is not already displayed. Also, at line 276 the most recent pressure value is displayed. Finally, at line 277, the value −2 is loaded in PLSCNT. PLSCNT is a counter which is incremented each time a blood pressure pulse is detected, and when the third pulse is detected (PLSCNT=0) the 10-second timing interval begins. The instruction at line 277 simply initializes PLSCNT so that the first two blood pressure pulses will be ignored (not insofar as systolic pressure measurements are concerned, but rather only with regard to the determination of pulse rate).

Figure 16:
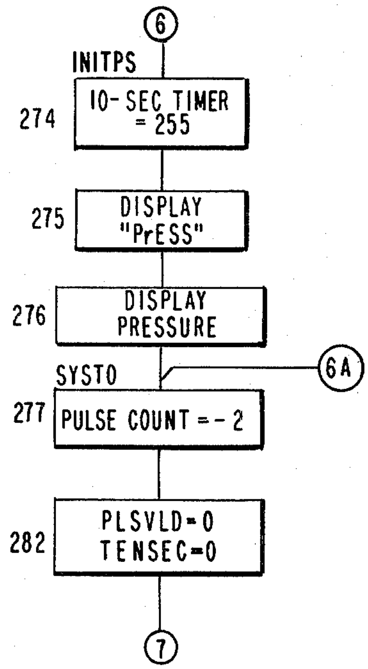
Figure 13:
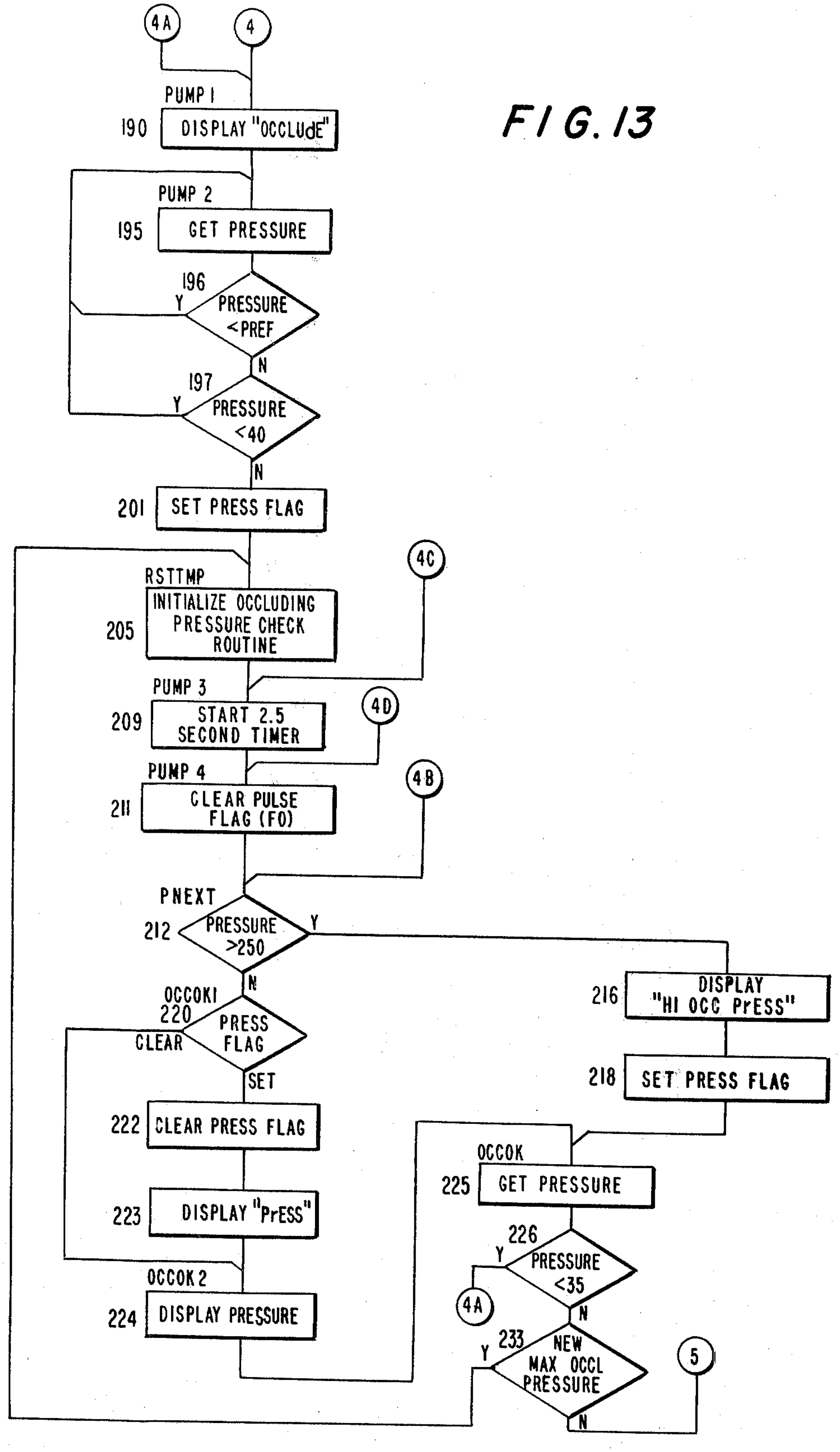
Figure 15:
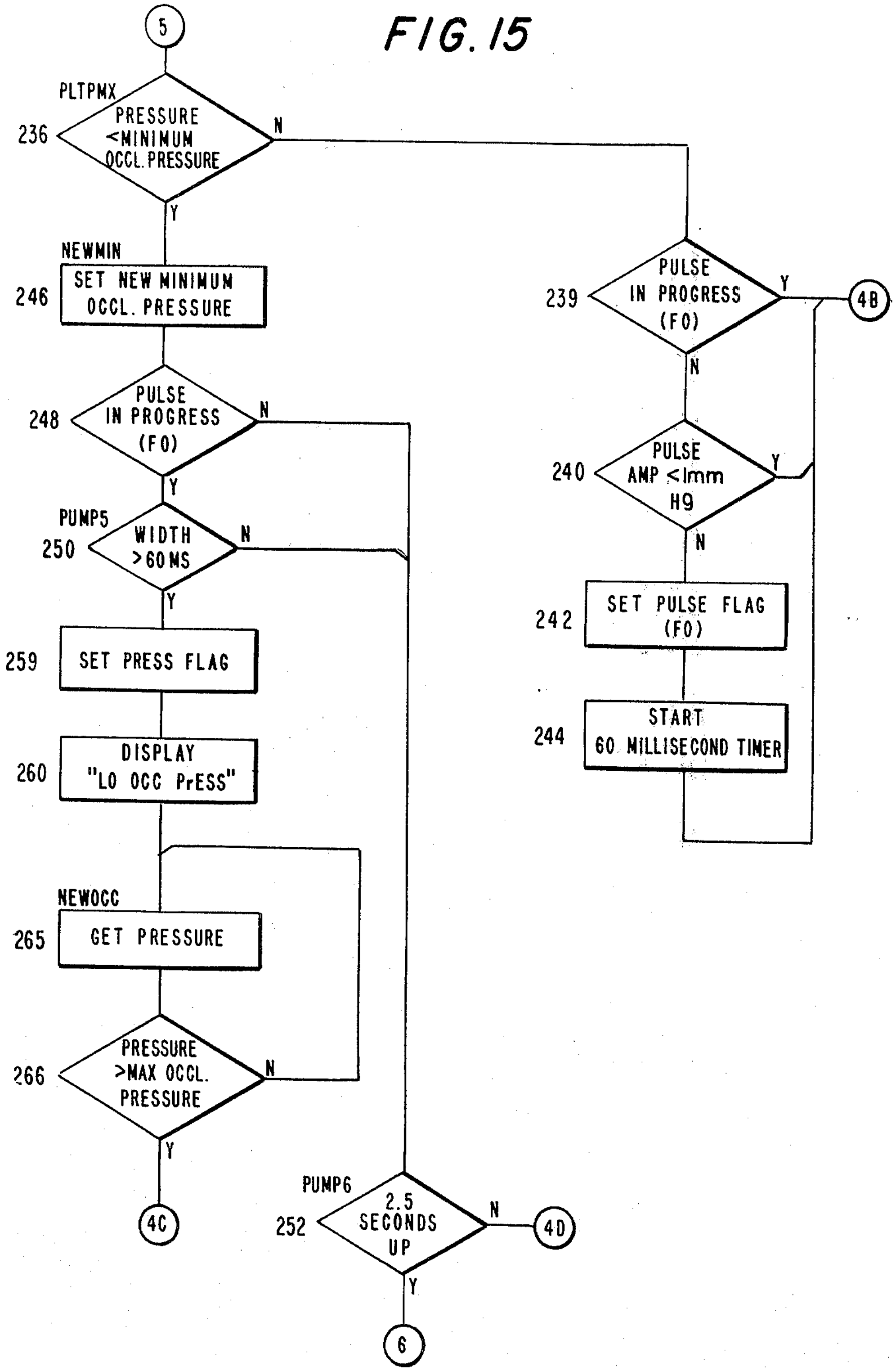

FIGS. 13, 15 and 16 are the flow charts for the just-described pump-up procedure and the determination of the onset of systolic pressure measurement.

Systolic Pressure Measurement

The systolic pressure measurement routine requires operations on four successive pulses detected after the artery has been occluded. Normally, the first four pulses are operated upon. However, if the difference between the occluding pressures at the starts of any two successive pulses (the first minus the second) is greater than or equal to 10 mm Hg, all pulses are disregarded and treated as artifacts; a new set of four pulses is operated upon.

At lines 282–284 (see flow chart of FIG. 16), PLSVLD and TENSEC are both set to 0. These data memory locations are used as flags in the pulse-rate processing routine, as will be described below. At line 285, COUNT is set equal to 4; COUNT is used to count the detection of the four pulses used to derive the systolic pressure value. A call is then made to the PLS subroutine. This subroutine monitors the falling occluding cuff pressure, detects a pulse, up-dates certain parameters, and then causes a return to line 287.

Figure 17:
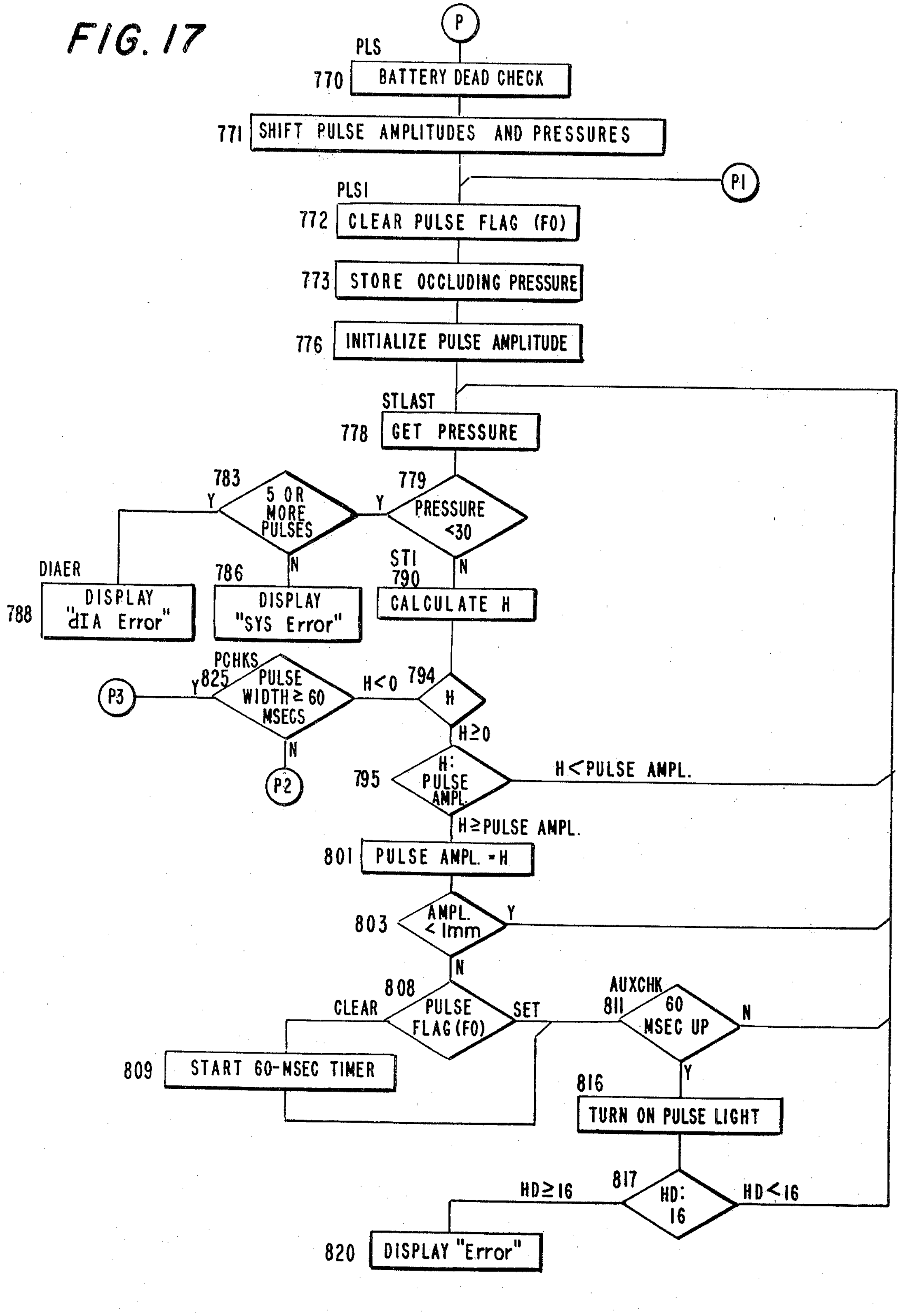
Figure 18:
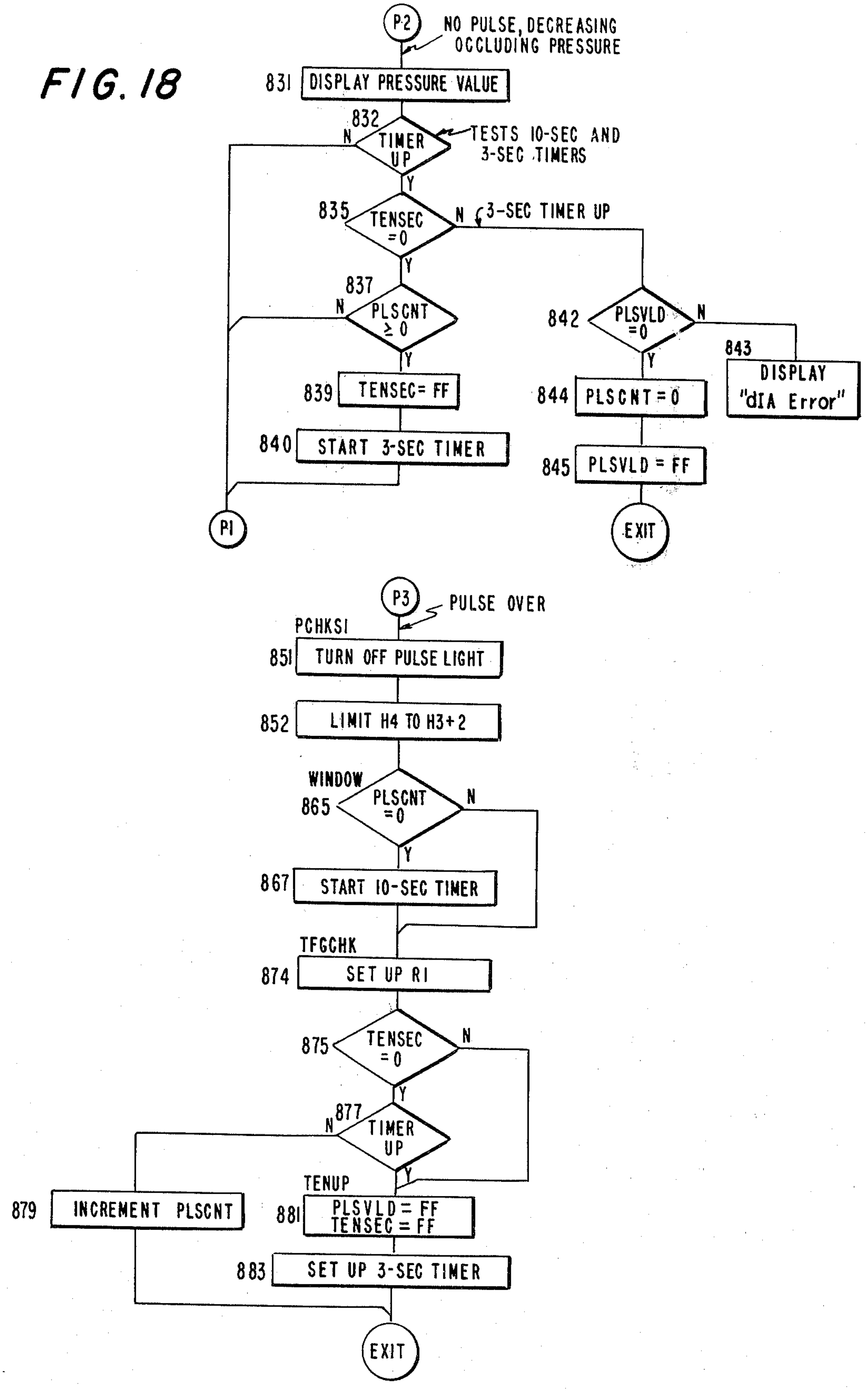

The flow chart for the PLS subroutine is shown in FIGS. 17 and 18, and the subroutine itself begins at line 770. A check is first made to see if the battery is dead. At line 771 a subroutine is called which shifts data within two tables maintained by the system. The two tables and the information which they contain may be best appreciated by first considering FIG. 19, which depicts the cuff pressure as the occluding pressure bleeds down followed by a blood pressure pulse which causes the cuff pressure to rise and then fall again. For each pulse, the system stores two pieces of data. The first is the occluding pressure in the cuff at the start of the pulse; this is the "last pressure" before the pulse and is referred to as "PLAST". As the cuff pressure rises due to the pulse, each PTMP sample (represented by the short vertical segments in FIG. 19) has PLAST subtracted from it to determine the pulse height H. As succeeding samples are taken, H first increases and then decreases. The maximum value of H represents the pulse amplitude, HD—the second piece of data stored for each pulse.

The first table maintained in the data memory is the PTBL table consisting of 8 locations for storing the occluding pressures for 4 pulses at the starts of the pulses, i.e., the respective values of PLAST. Referring to lines 54 and 55, it will be noted that the seventh location in the PTBL table is labeled PLAST. This is because the most recent PLAST value is stored in locations PTBL+6 and PTBL+7. At the start of the PLS subroutine, the data contained in each of the last three paired locations in the PTBL table are shifted to the next lower paired locations. Thus by the time four pulses have been detected, the PLAST value for the first is in the first two locations of the PTBL table (PR1), the PLAST value for the second pulse is in the next two locations (PR2), etc.—with the PLAST value for the fourth pulse being stored in locations PLAST and PLAST+1 (PTBL+6 and PTBL+7), with PLAST also having the alternate designation PR4 (see lines 63–66). In a similar manner, the HTBL table consists of four locations for storing the HD values—the pulse amplitude (the maximum H) for each of the four pulses. Each of these values requires only one byte since a pulse amplitude never even approaches a value of 127.5 mm Hg, corresponding to a value of FFH, which is the largest value which can be stored in the HTBL table. The HD value for each pulse is stored in location HTBL+3 (which is also labeled HD), but at the start of each PLS subroutine execution three shifts are performed to shift the previously determined HD values to lower positions in the table.

At line 771, a call is made to the SHFTH subroutine at line 702. AEX is loaded with the value 3; it serves as a counter to count three shifts. At the next two lines, register R0 is made to point to the second location in the HTBL table, and register R1 is made to point to the first. At line 705, a call is made to the SHFT1 subroutine at line 715.

This subroutine first causes the contents of location HTBL+1 to be moved to the accumulator, and at line 716 the accumulator contents are moved to location HTBL—the first shift. Registers R0 and R1 are then incremented. At line 719, AEX is decremented, and if it is not zero a branch is made to line 715. In this manner, the HD sample at location HTBL+2 may be transferred to location HTBL+1. Similarly, the sample in the fourth position of the table is shifted to the third position, and only then does the test at line 719 indicate that AEX is zero. At line 720, a return is made to line 709. The net result is that whenever the PLS subroutine is entered, the pulse amplitude values which appear in the HTBL table are shifted to adjacent lower positions.

Because the PTBL table contains double-precision values, six shifts are required rather than three. For this reason, at line 709 AEX is loaded with the value six. At lines 710 and 711, registers R0 and R1 are loaded respectively with the third and first addresses of the PTBL table, since the byte in the third location must be shifted to the first location, and the byte in the fourth location must be shifted to the second. The SHFT1 routine is then executed and the operation is as described in connection with the HTBL table, except that this time three double-precision PLAST values are shifted, following which a return is made to line 772. (It should be noted that while for both tables three values are shifted, not all of them are necessarily legitimate values. For example, when the PLS subroutine is first called, the two tables have no values of any significance since a pulse has not yet been detected. Three shifts are controlled whenever the PLS subroutine is called because this is the maximum number which is ever required—when the PLS subroutine is entered for the fourth time.)

The message "PrESS" appears on the display, and it remains there as long as the systolic pressure measurement is in progress. While the cuff pressure is falling and a pulse is not in progress, the instantaneous cuff pressure value is also displayed. But once a pulse is detected, the instantaneous cuff pressure corresponding to each sample is not displayed, that is, the display is not up-dated. Instead, the last cuff pressure prior to the start of the pulse (PLAST) is permanently displayed, and the "pulse light" is turned on to indicate that a pulse is in progress. (This is to avoid a rapid rise and fall in the displayed value—which can only be confusing.) Whether the pressure values are displayed, or alternatively the pulse light is illuminated, is controlled by internal flag F0. At line 772, the flag is cleared to indicate that pressure values should be displayed since a pulse has not yet been detected.

At lines 773 and 774, registers R0 and R1 are loaded so that they point to the respective addresses PTMP and PLAST. The call to the DMOVE subroutine at line 775 causes PLAST to be up-dated to the value of the current simple (PTMP). Referring to FIG. 19, what this means is that the system assumes that a pulse is about to begin and it thus stores the current sample value in the last of the four double-byte positions of the PTBL table. If the next PTMP sample is greater than PLAST, it is an indication that the onset of a pulse has indeed been detected and PLAST remains unchanged. But if the next sample value is less than PLAST, at lines 773–775, PLAST is up-dated once again to the new lower value since a pulse has not yet been detected.

At lines 776 and 777, the last position of the HTBL table (HD) is set to zero. The maximum height measured during the next pulse is initially set to zero since the pulse has not yet even been detected. At lines 778, a new pressure sample (PTMP) is taken.

During execution of the PLS subroutine the system checks whether the cuff pressure has fallen below 30 mm Hg—if the systolic or diastolic pressure has not been determined by this time, the measurement is aborted and an error message is displayed.

At lines 779 and 780, AEX and the accumulator are set to 60, representing a pressure value of 30 mm Hg. The call to the DMINC subroutine at line 781 sets the carry bit if the latest sample value is at least 60. If it is, the JC instruction at line 782 causes a branch to line 790 and processing continues. But if the occluding pressure is below 30 mm Hg, an error message is displayed. Which message is displayed depends on how many pulses have already been detected, i.e., did the error occur during systolic or diastolic pressure processing.

Referring back to line 277, it will be recalled that PLSCNT is initially set to $-2$ prior to the start of the systolic pressure measurement. At line 783, the value of PLSCNT is loaded into the accumulator, and at line 784 the value $-3$ is added to it. At the end of the PLS subroutine, at line 879, PLSCNT is incremented. Thus since its initial value was $-2$, and $-3$ is added to it at line 784, until five pulses have been detected, the accumulator will represent a non-zero value after the ADD operation. At line 785, the accumulator contents are complemented and, at line 786, the most significant bit in the accumulator is examined. If it is a 1, indicating that five or more pulses have been detected, a jump is made to line 788 to control display of the "dIA Error" message. Otherwise a jump is made at line 787 to line 447 to control display of the "SYS Error" message.

If the diastolic error message is to be displayed, at line 788 the relative address in page 3 of the disastolic error message is loaded into the accumulator. The jump at line 789 to line 452 controls the display of the message as will be described shortly. On the other hand, if PLSCNT has not been incremented up to 3, it is an indication that the systolic pressure measurement was still in progress and the instruction at line 447 is executed to load the accumulator with the relative address in page 3 of the systolic error message.

Before proceeding with the systolic pulse measurement description, it will be helpful to refer to the manner in which the error messages are displayed. No matter what the message, the call at line 452 controls its display. After the message is displayed, the ORL instruction at line 453 is executed, setting bit 3 of port 2 to a 1, to open the valve so that the cuff bleeds down to atmospheric pressure. The pulse light is turned off at line 454 by forcing bit 7 of port 1 to go high. Whenever the final display is formed, the pulse light is held off. The display persists, however, for only 10 seconds, and it is then turned off. At this time, the pulse light goes on to inform the operator that measurement data is still available and can be re-displayed by pressing the recall/cuff button. Thus the pulse light must be turned off when the display is first formed, but turned on 10 seconds later when the display is blanked (in order to conserve the battery).

At lines 455 and 456, a delay of 10 seconds is generated by first loading the accumulator with the value 100 and then calling the WAIT subroutine. By disabling the counter/timer at line 457, up-dating of the display ceases following expiration of the 10-second delay. The ORL instruction at line 458 de-energizes all of the display anode segment drivers. (The pulse light is still held off, but will be turned on in a moment.) The ANL instruction at line 459 is used to insure that no cathode of the display is energized. The value OFH is latched at port 2. Since the four least significant bits of the value latched at port 2, when complemented, represent the character position being operated upon, the "zero" character position is identified. Since this position is "illegal" as described above, it does not result in the energization of any character cathode. The ANL instruction at line 460 turns the pulse light on. At line 461, the recall/cuff test input (T0) is examined, and the system remains in an endless loop until the recall/cuff button is operated. When it is operated, the counter/timer is enabled at line 462 so that message characters will be refreshed at 800-microsecond intervals, and in line 463 a jump is made back to line 453. Since the message is to be displayed all over again, for another ten seconds, the "final" display routine starts from the beginning. The only options available to the operator are to recall the previous display, or to restart the entire system by pressing the reset button.

Returning to the PLS subroutine, by the time line 790 is reached, the PTBL and HTBL tables have been shifted so that they are ready to accept two new values, the next-to-last sample taken has been stored in PLAST (lines 773-775), and PTMP represents the most recent sample (line 778). At lines 790 and 791, the difference PTMP-PLAST is formed in AEX and the accumulator. (Register R0 points to PTMP from the call to READP at line 778.) Register R0 is then made to point to AUX33 and register R1 is set to point to HD—the last location in the HTBL table.

The test at line 794 checks whether PTMP is less than PLAST. If it is, i.e., the carry bit is not set, since the last time PLAST was set PTMP has increased and then decreased to a value below PLAST, i.e., a pulse which was in progress is over, or there was not a pulse in the first place and the cuff pressure is simply bleeding down. If PTMP is less than PLAST, the JNC test at line 794 controls a jump to line 825, at which time the pulse width is checked.

Thus far there has been described what happens when the latest PTMP sample is less than PLAST, in which case the test at line 794 controls a jump to line 825. (In general, tests such as this one may be for the "less than or equal to" condition, rather than just the "less than" condition. In this particular case, a pulse is determined to be over after PTMP samples have increased and then decreased, with the latest sample corresponding to the stored PLAST value.) But if PTMP equals or exceeds PLAST, then the instruction at line 795 is executed. This condition implies that the pulse has just started or is in progress. The accumulator contains the difference PTMP-PLAST. (Since even a maximum pulse height can be represented by the lowest byte in the two-byte PTMP-PLAST sample, it is only the value in the accumulator which is of concern.) The accumulator represents the pulse height H, and at line 795 it is temporarily stored in AEX. Register R1 points to HD—the maximum pulse height for the current pulse—as a result of the execution of the instruction at line 793. The four instructions at lines 796-799 form the difference H-HD in the accumulator. The most significant bit in the accumulator is tested at line 800 to see if H-HD is negative. If it is, it is an indication that H is less than HD, that is, HD already represents the maximum pulse height detected thus far for the current pulse. What is happening is that PTMP is moving along the pulse curve on its falling portion, but it is still greater than PLAST. A jump is made at line 800 to line 778 so that another sample can be read. (Since the start of the pulse has already been detected, the return is not made to line 772; PLAST is up-dated to PTMP and HD is reset to 0 only when the occluding pressure is bleeding down in the absence of a pulse.)

But if the current pulse height H is greater than the maximum pulse height determined thus far, HD must be set to H; what is happening is that PTMP is moving along the pulse curve on its rising portion. At line 801, the pulse height (presently stored in AEX) is loaded into the accumulator, and at line 802 it is moved into HD.

The accumulator now contains the maximum pulse height detected thus far, and the value $-2$ is added to it at line 803. This value represents a pressure threshold of 1 mm Hg. Until HD reaches a value of 2, that is, until a pulse amplitude of 1 mm Hg is detected, the system does not assume that a pulse is present. At line 804, the most significant (sign) bit of the accumulator is examined. If it is a 1, indicating that HD is less than 2, a jump is made to line 778 at which time another pressure sample is taken and the process continues. But if HD represents a pulse amplitude of at least 1 mm Hg, it is an indication that a pulse has just been detected, or that a pulse is in progress. At line 808, the F0 flag is examined. If it is still cleared, it means that a pulse has just been detected. No branch is taken at line 808. The F0 flag is set at line 809, and at line 810 the 60-millisecond pulse width timer is started. On the other hand, in the case of a pulse in progress, the timer need not be started; since flag F0 is already equal to 1, at line 808 a branch is taken to line 811. In either case, a check is made to see for how long the pulse has been present. The timer value, AUX33 is loaded into the accumulator at line 811. Until 60 milliseconds have gone by, i.e., before the pulse can be considered to be valid, AUX33 has not been decremented down to 0. The JNZ test at line 812 causes a branch to line 778 and the taking of another sample. Only if the pulse has persisted for 60 milliseconds is it considered to be a true pulse and the pulse light turned on. The light is turned on by setting bit 7 of port 1 to a 0, and the ANL instruction at line 816 does this. (Although turning the pulse light on is not necessary if a pulse is already in progress, there is no harm in repeating the operation.)

There is still one more test which is performed and that is to see if HD is too large. If it is greater than or equal to 16, representing a pulse amplitude of at least 8 mm Hg, it is probably an indication that the patient moved his arm and that the measurement cycle should be aborted—normal pressure pulses do not reach 8 mm Hg in amplitude. The instructions at lines 817 and 818 form the difference in the accumulator of HD and the value 16. If the carry bit is not set, indicating that the maximum pulse amplitude has not reached 8 mm Hg, a jump is made to ine 778 where the next sample is taken. But if the value of HD is too high, the accumulator is loaded with the relative address of the start of the "Error" message, and at line 821 a jump is made to the DRECAL subroutine—which controls the display of the message for 10 seconds, and allows the operator to recall the message. The entire measurement process is stopped and the instrument can be used again only by pressing the reset button.

As described above, the system reaches line 825 only after it has been determined that PTMP is less than PLAST (see line 794). There are two ways in which line 825 can be reached. First, an actual pulse may have been present and the pulse is over. Second, the occluding pressure fell between successive samples without a pulse having been present. If a pulse was present, as a result of it having persisted for more than 60 milliseconds, the pulse light was turned on. The pulse light is now examined to determine whether a pulse was present and is now over, or whether the occluding pressure has simple decreased since the previous sample. At line 825, the bit values at port 1 are read into the accumulator, and at line 826 the accumulator is complemented. If the pulse light was turned on, bit 7 at the port was set to 0 at line 816. Bit 7, after complementing, is now a 1. The JB7 test at line 827 controls a branch to line 851—a pulse was detected, and still another test is performed on it. But if the pulse light is off, the instruction at line 831 is executed.

FIG. 17 is the flow chart which depicts those steps of the PLS subroutine described thus far. As successive samples are taken the pulse height HD is up-dated if necessary, and if the occluding pressure falls below 30 mm Hg, one of two possible error messages is displayed. A third error message is displayed at the end of a blood pressure pulse, if the pulse height is too large. Otherwise, the system loops back to the "get pressure" step at line 778 until it is finally determined at line 794 that a pulse is over. At this point, a branch is taken either to point P2 or P3 depending on the width of the pulse. The branch to P2 is taken if the pulse width is less than 60 milliseconds, the assumption being made that a pulse was not in progress and that the occluding pressure has simply been decreasing. (The same branch to P2 is made if there was no pulse present at all and the occluding pressure is really decreasing.) A branch is taken to P3 only at the end of a pulse whose duration is at least 60 milliseconds. The flow chart of FIG. 18 depicts what then happens in the two respective cases. It is easier to understand the source listing between lines 831 and 896 by first considering the flow chart.

Pulses are counted for a 10-second interval starting with the third; the pulse rate can then be determined by multiplying the pulse count, PLSCNT, by six. Since PLSCNT is initially set to −2, and it is incremented whenever a pulse is detected, PLSCNT will be 0 only after the second pulse has been detected. Thus the test for starting the 10-second timer is to see whether PLSCNT is 0 when a pulse is detected; if it is, the 10-second timer is started. The timer is started only once since PLSCNT is 0 only prior to the detection of the third pulse.

The reason for starting the count with the third pulse is that sometimes the amplitude of the second is too low to be detected; if the count starts with the first pulse, the final value will be too low. By starting the count with the third pulse, this problem is avoided.

The system also provides still another check. A three-second timer is started after the 10-second timer finishes. At least one pulse must be detected within the 3-second timing interval for the pulse count (PLSCNT) value to be considered valid. Otherwise, the occluding pressure is probably so low that pulses cannot be detected; this, in turn, means that in all probability not all of the pulses which were present during the 10-second interval were actually detected and added to the pulse count value. Two register flags are used to keep track of what is going on—TENSEC and PLSVLD. Referring back to lines 283 and 284, it will be noted that both flags are set to 0 before the PLS subroutine is called for the first time. The TENSEC flag is set to a non-zero value (the HEX value FF is arbitrarily chosen) only after the 10-second timing interval has gone by. Thus the condition TENSEC≠0 is an indication that the system is in the 3-second timing interval. The PLSVLD flag is used to indicate whether at least one pulse is detected during the 3-second timing interval. If it is, PLSVLD is similarly set to the HEX value FF. If PLSVLD=0 at the end of the 3-second timing interval, it is an indication that in all probability not all pulses were counted during the 10-second timing interval, and the PLSCNT value is not reliable.

Consider the case in which the artery is fully occluded and the pressure is bleeding down. The entry point is P2 on FIG. 18, and at line 831 the pressure value is displayed. The "timer up" test at line 832 must be understood because it is applicable to both timing intervals. The same register AUX22 is used to time both intervals. In each case, a different starting value is stored in the register, and thus the register value will be 0 at the end of the respective time interval. It will be recalled that at line 274 AUX22 is set to an arbitrarily high value. Thus as the occluding pressure first starts to fall, AUX22 will be non-zero. The "timer up" test at line 832 controls a branch to P1 on FIG. 17, at which time, after some initialization steps, another sample is taken.

This process continues until eventually a pulse is detected, and a branch is made to point P3 on FIG. 18. At line 851, the pulse light is turned off since the pulse is over. The pulse height, HD, is stored in the fourth position of the height table—H4 (see lines 52, 53 and 61). The previous pulse height is in location H3. In order that artifacts not unduly influence subsequent processing, no pulse height is allowed to exceed the previous pulse height by more than 1 mm Hg (a value of 2 since the instrument resolution is 0.5 mm Hg). While the occluding pressure is decreasing during the initial pulses which are detected, the pulses should be increasing in magnitude but not radically different from one another. That is why any pulse height which is registered is held to within 1 mm Hg of the previous pulse height. During diastolic processing (the PLS subroutine is called at this time as well), as the occluding pressure continues to decrease, the pulse heights decrease rather than increase; although the processing starting at line 852 also takes place at this time, rarely will the height of the most recent pulse (H4) have to be limited to a value of 2 above the height of the previous pulse (H3).

When the first pulse is detected, PLSCNT is still equal to −2. Thus the test at line 865 causes a branch to line 874. The set-up instruction at this line does not relate to the methodology, but rather to how it is implemented, as will become apparent when the detailed listing is considered. At line 875, since TENSEC is still 0, the test at line 877 is executed. Since the 10-second timer has not even started, PLSCNT is incremented at line 879, and an exit is made from the PLS subroutine.

Until PLSCNT is incremented to 0 (after two pulses have been detected), successively decreasing pressure samples cause a branch to P2 on FIG. 18, and at line 832 a branch is made back to point P1 on FIG. 17. Similarly, when each of the first two pulses is detected and a branch is made to point P3 on FIG. 18, all that happens is that PLSCNT is incremented. But when the third pulse is detected, since PLSCNT equals 0, the 10-second timer is started at line 867. Since TENSEC is still 0, and the timer has only started, the test at line 875 has a yes answer, the test at line 877 has a no answer, PLSCNT is incremented, and a return is made from the PLS subroutine.

As successive pulses are detected, PLSCNT is incremented at line 879. Alternatively, whenever a pressure sample is less than the preceding pressure sample, i.e., the occluding pressure is simply decreasing with no pulse being present, at line 831 the pressure value is displayed, and at line 832 a branch is made back to point P1 on FIG. 17.

It is only when the 10-second timer times out that a different action is required. At this time TENSEC is set to FF (any number different from 0 could be used), and the 3-second timer is started. The same "timer up" tests can be used at lines 832 and 877 on FIG. 18 because the value of TENSEC (0 or FF) is an indication of whether the system is in the 10-second timing interval or the 3-second timing interval.

One complication is that the 10-second timing interval may be completed when the next sample represents either a falling occluding pressure or the end of a pulse. Consequently, both routines on FIG. 18 must provide for starting of the 3-second timer and the setting of TENSEC to FF.

With reference to the entry point at P2, after the 10-second timing interval is over, the test at line 835 is executed. Since TENSEC is still 0, the test at line 837 is executed. Assuming that PLSCNT is greater than or equal to 0, at line 839 TENSEC is set to FF, and at line 840 the 3-second timer is started. (If PLSCNT is not at least 0, an exit is made—something is wrong and TENSEC is not changed.) Similarly, if the end of a pulse is detected just after the 10-second timer has timed out, at line 875, since TENSEC is still 0, the usual test at line 877 is performed. Since the 10-second timing interval is now over, the test at line 877 does not control a branch; instead, at line 881, TENSEC is set equal to FF, and at line 883 the 3-second timer is started. PLSCNT is no longer incremented; pulses are counted for only 10 seconds. In this case, starting at line 881, PLSVLD is also set equal to FF. This flag is initially 0 and must be set to FF (or any non-zero value) if at least one pulse is detected during the 3-second timing interval. Since the 10-second timing interval is over and a pulse has just been detected, it falls within the 3-second timing interval (even though, strictly speaking, the timing interval is not started until line 883 is reached).

The next pulse which is detected causes a branch to P3. Since TENSEC is no longer 0, a branch is taken to line 881. The setting of TENSEC to FF once again is of no moment, nor is the fact that the 3-second timing interval is started once again. What is important is that if the 3-second timing interval was started at line 840 without PLSVLD being set equal to FF, it is now set equal to FF by the first pulse which arrives during the 3-second timing interval.

After the 3-second timing interval is over, if the next pressure sample represents the end of a pulse, a branch is taken to point P3 but no values are changed; an exit is made from the PLS subroutine.

Eventually, when a sample is taken which represents a falling occluding pressure, the test at line 832 reveals that the 3-second timing interval is over and the test at line 835 is performed. Since TENSEC is now equal to FF, instead of the instruction at line 837 being executed a branch is taken to line 842. The instruction at line 842 is executed only once—at the end of the 3-second timing interval. If PLSVLD is not 0, at line 843 the "dIA Error" message is displayed. If PLSVLD=0, PLSCNT is set equal to 0, PLSVLD is set equal to FF, and a return is made from the PLS subroutine.

The reasons for setting the various values at lines 844 and 845, and the meaning of the various values to the mainline routine will now be explained.

PLSCNT is incremented only as pulses are detected during the ten seconds which start with the detection of the third pulse. PLSVLD is set equal to FF as soon as a pulse is detected in the 3-second timing interval. If at least one pulse is detected following the 10-second timing interval, in all probability all pulses were counted during the 10-second interval and the PLSCNT value is valid. (Still another check is performed, as will be described below, to verify that the value of PLSCNT is within minimum and maximum bounds.) Whenever a return is made from the PLS subroutine, the mainline routine checks whether the value of diastolic pressure has already been determined. If it has, and if PLSVLD=FF, then it in an indication that the final values may be displayed. This situation is controlled following an exit from the PLS subroutine at the bottom of the flow chart on FIG. 18. After diastolic pressure has been determined, and as soon as PLSVLD=FF, the mainline routine is made aware that all measurement values are available for display (even though the 3-second timer has not timed out).

Thus the 3-second timing interval will usually not time out. Diastolic pressure is usually determined before 13 seconds have gone by following detection of the third pulse, and the first pulse in the 3-second timing interval which sets PLSVLD=FF causes the system to stop calling the PLS subroutine. But suppose that the 3-second timing interval does time out. In such a case, the test at line 832, at the top of the flow chart on FIG. 18, allows the instruction at line 835 to be executed, and since TENSEC=FF a branch is taken to line 842. If PLSVLD=FF, it means that at least one pulse was detected during the 3-second timing interval. But because the PLS subroutine is still being called, the two terminating conditions (diastolic pressure established and PLSVLD=FF) cannot both exist. Since PLSVLD=FF, it must be that diastolic pressure has not yet been determined. The absence of pulses for 3 seconds, after PLSVLD has been set to FF, is an indication that pulses are not being detected during diastolic processing. A branch is taken to line 843 and the "dIA Error" message is displayed; another measurement cycle can be started by operating the reset button, and no values are displayed for the cycle just completed.

But suppose that PLSVLD=0 when the test at line 842 is performed. The fact that a pulse was not detected during the 3-second timing interval is an indication that in all probability not all pulses were counted during the 10-second timing interval. At line 844, PLSCNT is set equal to 0. This is a value below the minimum bound, and results in a display of three dashes rather than the pulse rate. But the fact that PLSVLD=0 does not necessarily mean that a previously computed value for diastolic pressure is invalid. For this reason, at line 845, PLSVLD is set equal to FF before an exit is made from the PLS subroutine. The mainline processing checks whether diastolic pressure has been established. If it has, its value will be displayed. If it has not, the next call to the PLS subroutine results in the display of the "dIA Error" message since PLSVLD is now FF, and the test starting at line 842 results in a "no" answer.

Referring to the source listing, the instruction at line 831 is executed when the latest pressure sample represents a decreasing occluding pressure, and the sample value is displayed. On the flow chart of FIG. 18, the "timer up" test at line 832 tests both timers. The system does not know which time interval is in progress. As shown in the source listing, it simply loads the value of AUX22 in the accumulator and then tests it at line 834. A non-zero value controls a jump to line 772, point P1 on the flow chart. But if AUX22=0, the system must determine which timing interval has just finished. At line 835, the value of TENSEC is loaded into the accumulator, and a jump is made to line 842 if TENSEC is not 0. The only way that this can happen is if the 3-second timing interval has just finished. Starting at line 842, either the "dIA Error" message is displayed, or PLSCNT and PLSVLD are set as shown on FIG. 18.

On the other hand, if the test starting at line 832 indicates that a timing interval is over, and the test at line 835 reveals that it is the 10-second timing interval which was just in progress, the instruction at line 837 is executed. The value of PLSCNT is stored in the accumulator and the most significant bit is examined. If it is a 1, indicating that less than two pulses have been detected, the JB7 instruction causes a jump to line 772, point P1 in the flow chart. Only if PLSCNT is at least 0 is TENSEC set to FF at line 839, and the 3-second timer started at line 840, following which a jump is made to line 772.

In the case of a pulse, the flow chart of FIG. 18 indicates that at line 851 the pulse light is turned off. This is accomplished by forcing high the most significant bit at port P1, as shown in the source listing. The next step in the flow chart limits H4 to 1 mm Hg above H3. This is accomplished at lines 852–861. At lines 852–854, the value H3+2 is computed, and at line 855 it is stored in AEX. By then complementing the accumulator and incrementing it, the value −(H3+2) appears in the accumulator. Line 851 is reached only from line 827, and register R1 is set to point to H4 (same as HD) at line 793 without being changed before line 827 is reached. Consequently, at line 858 register R1 still points to H4, and the sum H4-(H3+2) is formed in the accumulator. If H4 is less than (H3+2), the carry bit is not set and a branch is made to line 865. But if the carry bit is set, the value temporarily stored in AEX, (H3+2), replaces the value H4, as controlled by lines 860 and 861, before the instruction at line 865 is executed.

It should be noted that the first pulse height which is measured is also adjusted in accordance with the amplitude of the preceding pulse (H3)—even though there was no such pulse. As it turns out, however, this does not pose a problem. Assume that when the system is reset, data memory location H3 actually contains a negative number. If the complementing step at line 856 results in a positive number in the accumulator by the time the instruction at line 858 is executed, there will be no carry. A jump is made to line 865, and the value of H4 remains equal to the measured value. If, on the other hand, H3 initially contains a large positive value, H4 also remains the same since H4 is never changed if it is less than H3. The only "problem" case is that in which H3 is 0, or near 0. This would limit H4 to a low value even though H4 may be higher. But the first pulse magnitude is always small. In fact, it is almost never greater than 1 mm Hg (unless it is an artifact, which results in an "Error" display—see lines 817 and 820 on FIG. 17). Thus there is no error introduced by actually limiting the first H4 value to an arbitrarily low value.

As shown in the flow chart of FIG. 18, starting at line 865 the value of PLSCNT is examined. If it is not 0, a jump is made directly to line 874. But if it is 0, an accurate 10-second timing interval is established at lines 867–870, by loading AUX11 with the value 125 and by loading AUX22 with the value 100. (At line 869, register R1 is made to point to AUX22 by incrementing register R1—AUX22 follows AUX11 in the data memory.)

Referring to the flow chart of FIG. 18, it will be noted that at line 874, register R1 is set up. As described above, this step is not required for an understanding of the overall methodology but it is necessary for the actual processing. At line 874, register R1 is made to point to AUX22—this is required in order to check whether the timer is finished starting at line 877. But first the value of TENSEC is examined at lines 875 and 876, and a jump is made to line 881 if it is not 0. Only if it is 0 does the system proceed to line 877. If the value of AUX22 is 0, a branch is taken at line 878 to line 881. Otherwise, as shown on the flow chart of FIG. 18, at line 879 PLSCNT is incremented and a jump is then made to line 896 from which a return is made.

Starting at line 881, PLSVLD and TENSEC are both set to the HEX value FF. Then, at line 883, the 3-second timer is started, following which the subroutine is exited at line 896.

This completes the description of the PLS subroutine, but lines 885–898 require explanation. It will be noted that at line 11, TEST is set equal to FALSE. This is done to set up a conditional assembly. Line 887 in effect says that if TEST=TRUE, then the object program which is assembled includes code for lines 889–892. Since TEST is FALSE, what is assembled is the single instruction at line 896—a return.

The instructions at lines 889–892 result in the assembly of object code only if in line 11 TEST is set equal to TRUE. In such a case, the resulting object code (which is conveniently loaded into a PROM) provides an added capability—not for the ultimate user, but rather for the designers of the instrument. During the course of designing the instrument, it was important to examine pulse heights—for the purpose of setting threshold values and in order to verify the processing which was taking place. Toward this end, it was desirable to display the amplitude of each pulse as it was measured. During the processing described thus far, the "PrESS" message is displayed together with a 3-digit value in the last three positions of the display. The fourth position from the end is blanked. What the conditional assembly provides is a display of pulse height at this position of the display.

At line 889, register R1 is made to point to HD—the pulse height for the current pulse. Since line 889 is executed just after a pulse has been detected, at line 890 the height of the pulse is stored in the accumulator. Register R1 is then made to point to the fourth position from the end of the display table. It will be recalled that a jump to the BCDSG subroutine at line 549 causes the display of a single digit whose value is contained in the accumulator; the position at which the digit is displayed is controlled by the position in the display table pointed to by register R1. Thus the JMP instruction at line 892 causes the pulse height value to appear in the display between the "PrESS" message and the 3-digit occluding pressure value. Instead of the return being made from the PLS subroutine at line 896, the return is made from line 554, at the end of the BCDSG subroutine.

Reference should also be made to lines 745 and 746. The segment codes which are stored at the start of page 3 of ROM are those which represent the 10 decimal digits, followed by the HEX digits A, b, C and d, and finally a dash and a blank. Thus the values of HD which are actually displayed are the usual first 14 HEX digits (two of which are lower case to distinguish them from 8 and 0 respectively), but with E and F being represented by a dash and a blank respectively. While the display might be confusing to the ultimate user, he never sees it. The conditional assembly instruction TEST EQU TRUE (at line 11) is utilized to derive an object code which controls an instrument used only by the designers.

During systolic pressure processing, COUNT is initially set equal to 4 at line 285, just before the PLS subroutine is called for the first time. COUNT is to be distinguished from PLSCNT, the latter being incremented (line 879) at the end of the PLS subroutine. PLSCNT is used to count the number of pulses which occur during the 10-second timing interval. COUNT, on the other hand, is used to determine when four successive pulses have been detected in order to derive a value for systolic pressure.

Although the main purpose of COUNT is to determine when four pulses have been detected, COUNT serves in an additional capacity. The system performs a check to determine whether the occluding pressure has fallen by 10 mm Hg or more between successive pulses. If it has, it is assumed that all pulses detected thus far are artifacts and the entire systolic processing sequence is started all over again; at the bleed rate utilized, the pressure should not fall by 10 mm Hg between pulses. Referring to the systolic processing flow chart on FIG. 20, at line 290 the present pressure value (PR4) is subtracted from the previous pressure value (PR3) in the DTBL table, and if the difference is at least 10 mm Hg, a branch is taken to line 277 (see also FIG. 16). But the pressure value corresponding to the first pulse cannot be subtracted from the pressure value corresponding to the preceding pulse because there was no such preceding pulse. For this reason, at line 287, COUNT is moved to the accumulator, and then −4 is added to it. If the result is 0, indicating that it is the first pulse which has just been detected, a branch is taken to line 295, and the PR3–PR4 test is skipped. For all pulses starting with the second, at lines 290–292, the difference PR3–PR4 is formed in the accumulator. The value −20 is then added to the accumulator at line 293. The HEX code representation for −20 is EC. It is therefore apparent that as long as the HEX code value of PR3–PR4 is equal to or less than 13 (decimal 19), the carry bit will not be set as a result of the ADD operation at line 293. But if PR3–PR4 is greater than 19, corresponding to a pressure difference of at least 10 mm Hg, the carry bit will be set. The test at line 294 causes a jump to line 277 at which time PLSCNT is initialized all over again.

Assuming that the test is passed, however, the instruction at line 295 is executed. The value of COUNT is decremented. Until it is decremented down to 0, a jump is made to line 286, at which time the system waits for another pulse. It is only after four pulses have been detected that the system advances to the next line—by which time four pulses have been detected.

The PTBL table contains four PLAST values—each of which is the cuff pressure at the start of a pulse. Similarly, the HTBL table contains four HD values, each of which is the amplitude of a respective pulse. The system now determines whether the HD values represent a valid sequence. If they do, the third PLAST value (PR3) is taken to be the systolic pressure. It is not really critical which of the PLAST values is taken to be the systolic pressure. While it might be thought that the first value is the correct one, experiments have shown that this is not the case. (Furthermore, the sound level heard in such a case when using a stethescope is so faint that even when using the conventional technique for measuring systolic pressure, it is the cuff pressure at the onset of a "wrong" pulse which is often taken to be the systolic pressure—due to variations in hearing and ambient sound levels.) It is probable that the cuff pressure will change by a few mm Hg between the first and third pulses, and to this extent the systolic pressure measurement may be in "error". But it is not a precise measurement to within a few mm Hg that is critical; rather, what is important in blood-pressure measurements is the trend over a period of time. It is more important to observe a change in systolic pressure value than it is to know the exact value to within a few mm Hg. Thus it is better to use the cuff pressure at the onset of the third pulse to represent systolic pressure, in order to achieve consistent results over a long period of time, than it is to use the cuff pressure at the onset of the first or second pulse.

Even more important is the fact that it is the cuff pressure at the onset of the third pulse which indeed is the closest approximation to systolic pressure, despite popular thinking to the contrary. Based on a series of experiments conducted, during which the interarterial pressure was measured, it was found that of the four values in the PTBL table, PR3 was usually actually closest to the systolic pressure as determined by the interarterial method.

The routine between lines 299 and 329 determines whether the HD sequence (H1, H2, H3, H4) is a valid one; if it is valid, the systolic pressure is set to the third PLAST value.

Figure 20:
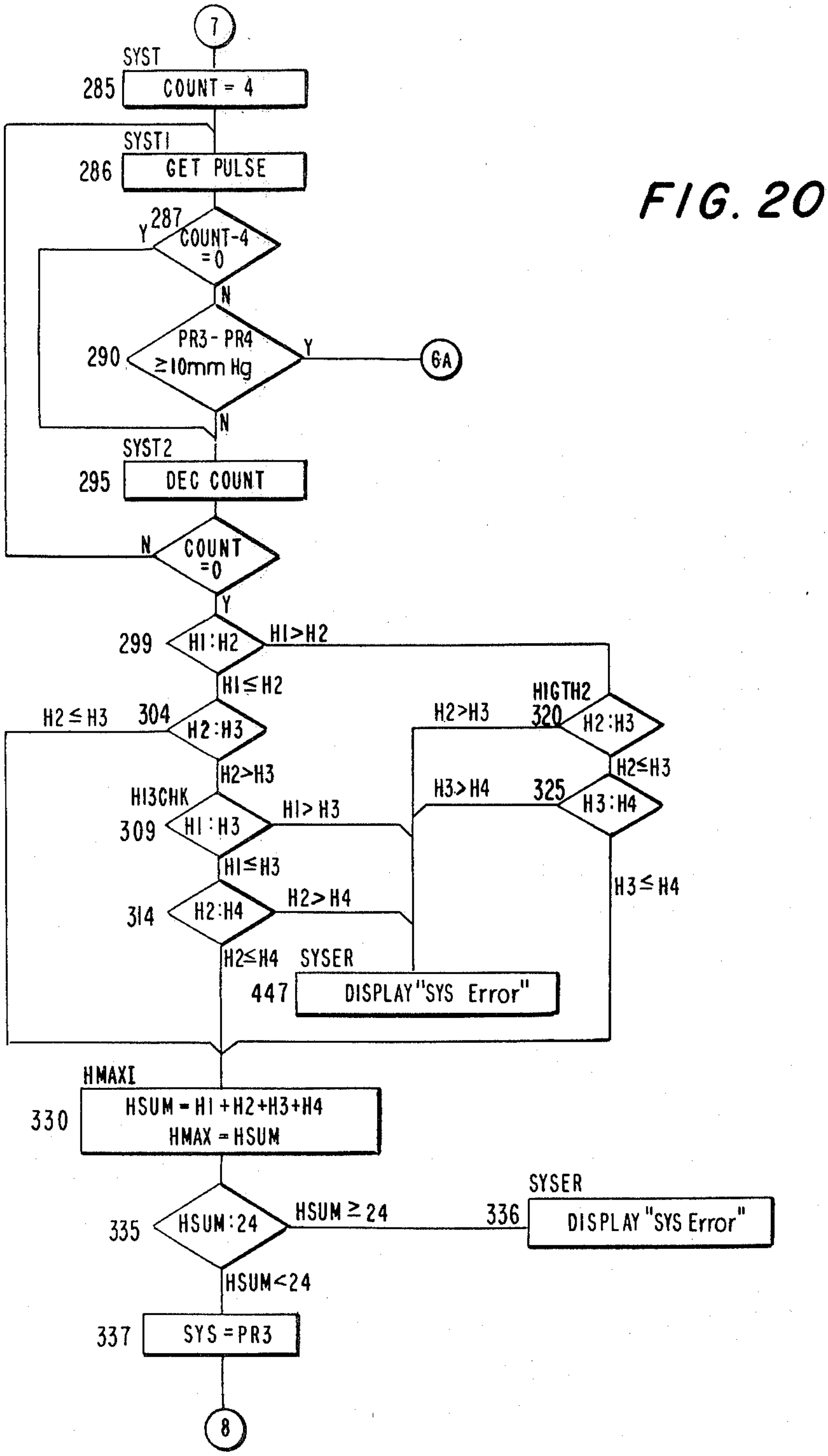

The routine is best understood by considering the flow chart of FIG. 20. At line 299, a test is first made to see if H1 (the first HD value in the HTBL table) is greater than H2. If it is, a branch is made to the right, as indicated. The H2:H3 and H3:H4 tests are then performed. Since H1 is greater than H2, if either H3 is less than H2, or H4 is less than H3, an error has occurred in the systolic pressure measurement and at line 447 the message "SYS Error" is displayed. On the other hand, if H1 is less than or equal to H2, numerous other tests are performed. Several of these lead to systolic error conditions, and several do not.

Rather than to analyze the flow chart step by step, it is more convenient to depict the more usual types of result as in FIG. 22. For each pulse sequence (a)–(j), a systolic error is indicated as the "determination" or, if the sequence is a valid one, the word "valid" is indicated. Each pulse sequence is read from left to right, with the leftmost pulse being the first.

Sequences (a) and (b) do not exhibit three pulses with increasing amplitudes (the basic criterion for validity) and the measurements are invalid. Sequence (c) is that which occurs when the first pulse is unusually large, usually due to a spasm or an arhythmia. Since the last three pulses are in the proper increasing order, the measurement is assumed to be valid.

In sequence (d), the first pulse is larger than the second only, rather than larger than all of the last three pulses as in sequence (c). The measurement is therefore valid. Similar remarks apply to sequence (e) where the first pulse is larger than the next two. Sequence (f) is the ideal case in which the four pulses increase in amplitude from the first to the last.

Sequence (g) shows the first three pulses increasing in amplitude but the last having an amplitude lower than the third. This is also a valid sequence. The general trend of the pulse amplitudes is to increase and then decrease. This is precisely what is happening in sequence (g), even though in most cases the pulse amplitudes will not start to decrease as early as the fourth.

Sequence (h) also shows three increasing pulse amplitudes—H1, H2 and H4. However, because H3 is too low, it is most probable that an error has occurred; for a valid measurement, H3 must be greater than either H1 or H2, and it is smaller than both of them in sequence (h). In both of sequences (i) and (j), H3 is greater than H1 (although not H2), and in this respect the sequence is valid. But in such a case, for the system to assume that the measurement is valid, H4 must be the largest amplitude. Since it is not in sequence (i), this sequence is invalid; H2 is just too large for the sequence to be reliable. Sequence (j), however, is valid since H4 exceeds H2.

Referring to the actual source statements, reference should first be made to lines 108–112. These lines define a macro (CMPH) which controls a single-precision subtract operation. At lines 109–110, registers R0 and R1 are made to point to the minuend and the subtrahend. The call to the MINV subroutine (lines 467–471) causes the subtraction operation to be performed with the result remaining in the accumulator. The macro is used six times in the routine which checks the pulse amplitudes for valid systolic measurement criteria. Each reference to the CMPH macro, e.g., at line 299, causes the three macro instructions to be assembled. Each of these instructions is identified by a plus sign which appears after its line number.

The routine follows the sequence shown in the flow chart of FIG. 20. At various points in the routine where a systolic error is detected, a jump is made to SYSER (line 447); it has already been described how a jump to this line causes the display of the "SYS Error" message and entry to the "recall" routine. Whenever a valid sequence is determined to have occurred, the instruction at line 330 is executed.

For reasons to be described below, the system requires the sum of the four most recent pulse amplitudes (HSUM=H1+H2+H3+H4), and it also maintains a record of the largest such sum (HMAX) computed during the overall measurement cycle. At line 330, a call is made to the HSUM subroutine at lines 436–443. After the accumulator is cleared, register R0 is made to point to the first entry in the HTBL table, H1. AEX is then loaded with the value 4 to control four addition operations. Lines 439–441 control the additions to the accumulator of the four pulse amplitudes as the contents of register R0 are incremented, with the DJNZ instruction controlling a branch back to line 439 only until AEX has been decremented four times. The value HSUM is then temporarily stored in AEX, after which a return is made to line 331. Since the first HSUM value has just been computed, HMAX is set equal to it at line 331.

A check is now performed to make sure that the systolic pressure processing has been carried out correctly. If very large artifacts have been detected, the measurement cycle is aborted. The test is whether HSUM is less than 24; it should be if the first four pulse amplitudes are "reasonable" (as a group); the test threshold was derived empirically. The call to the HSUM subroutine leaves HSUM in the accumulator. At line 335, the value −24 is added to the accumulator. In 2's complement arithmetic, −24 is represented by the HEX value E8. If HSUM is at most 23, 17 in HEX notation, HSUM −24 (decimal) is equivalent to E8+17=FF in HFX notation. When −24 is added to the accumulator at line 335, a carry is not generated and no branch is taken at line 336. But if HSUM exceeds 23, a carry is generated, and at line 336 a branch is made to line 336 at which time the "SYS Error" message is displayed.

But where a valid systolic measurement has occurred, the systolic pressure is set equal to the cuff pressure at the start of the third pulse. At line 337, register R0 is made to point to the first location (PR3) of the two which store the third PLAST value in the PTBL table and, at line 338, register R1 is made to point to SYS, the first of two locations in which the systolic pressure is stored. The call at line 339 to the "double move" subroutine causes the two bytes representing the systolic pressure (at PR3 and PR3+1) to be loaded at locations SYS and SYS+1. This completes the systolic pressure processing, the flow chart for which is depicted in FIG. 20.

Diastolic Pressure and Pulse Rate Measurements

Before proceeding with a detailed description of the diastolic pressure measurement, it will be helpful to discuss the methodology. While systolic pressure (SP) represents the maximum arterial pressure, minimal arterial pressure is coincident with the end of the resting phase, and is called the diastolic pressure (DP). The mean arterial pressure is usually given as the average of the systolic and diastolic pressures. However, the true mean arterial pressure is not the average of the systolic and diastolic pressures. The true mean pressure is the level at which the integral of the pressure waveform above equals the integral of the pressure waveform below. The true mean actually lies closer to the diastolic pressure than the systolic pressure, as taught by Best & Taylor, supra; the mean arterial pressure is actually equal to the occluding cuff pressure when the pulse of maximum amplitude is detected. It should be emphasized that it is not the maximum pulse amplitude which is the mean arterial pressure. Rather, it is the value of the falling occluding pressure at the start of the pulse which exhibits the largest amplitude.

FIG. 21 shows a typical envelope of pulse amplitudes, and in the drawing there is only one maximum pulse amplitude. While that is indeed a possibility, it is also possible that several pulses may have the same maximum amplitude. In this situation, the mean arterial pressure is the occluding cuff pressure when the last of these maximum pulses is detected.

The term "fifth phase diastolic" (see FIG. 21) generally refers to the disappearance of sound when a stethoscope is used in the taking of blood pressure; ideally, it represents the onset of equal low-amplitude pressure pulses. In actual fact, however, equal-value pressure pulses are rarely obtained when the occluding cuff pressure has fallen down to the diastolic pressure region. What the system of the invention does is to look at the average of the amplitudes of the four most recent pulses, and to compare this average with a threshold level. When the average falls below the threshold level for the first time, the PLAST value corresponding to the second of the four pulses in the last group of four is taken to be diastolic pressure. (While the PLAST value corresponding to the first pulse in the last four might alternatively be taken to be the diastolic pressure, experiments have shown that more accurate values are obtained by using the PLAST value corresponding to the second pulse.)

The question is what should be the threshold value. It is to be expected that patients with overall large pulse amplitudes will have a higher threshold level—diastolic pressure is reached when the average pulse amplitude of four successive pulses falls below a threshold level which is relatively high; for such patients, all pulse amplitudes are relatively high. For this reason, the threshold value varies from patient to patient. Actually, instead of computing an average pulse amplitude and comparing it with a threshold, the four amplitudes are added together and compared with a threshold which is four times greater than it otherwise would be. It should be pointed out that the technique of comparing a "sliding average" of four pulse amplitudes with a computed threshold level sometimes results in a determination of diastolic pressure which more properly should be the cuff pressure at the onset of the first pulse of the four whose average is less than the threshold level, or the cuff pressure at the onset of the third of the last four pulses. The bleed rate varies with the cuff pressure. At high cuff pressures, the bleed rate may be as high as 4–5 mm Hg per pulse, while in the diastolic pressure region the bleed rate is closer to 2 mm Hg per pulse—the larger the cuff pressure, the greater the bleed rate. Thus the diastolic pressure "error" may be ±2 mm Hg, and perhaps even ±4 mm Hg if the diastolic pressure is determined two pulses too early or two pulses too late. However, it is trends which are more important than accurate values. The slower the bleed rate (i.e., the smaller the orifice), the better the resolution; however, a slower bleed rate will require much more time to complete an overall measurement cycle. (Long measurement cycles are to be avoided because they deteriorate the artery, induce muscle spasms, and cause blood pooling and patient discomfort.)

The threshold value which is used in the diastolic pressure determination is to a certain degree a function of the mean arterial pressure. As mentioned above, the mean arterial pressure is the occluding cuff pressure at the onset of the pulse of largest amplitude. Rather than to rely, however, on the amplitude of a single pulse for deriving the threshold value, the system determines the largest sum of amplitudes over four successive pulses. HMAX is a sliding sum of the amplitudes of four successive pulses. It is continuously up-dated in order to determine a quantity which is a measure of mean arterial pressure. Just as mean arterial pressure is the cuff pressure at the onset of the last pulse of two or more equal (largest) pulse amplitudes, the system assumes that HMAX has been determined only with the most recent sum of amplitudes if it happens to equal the previously maintained HMAX value. Once HMAX is determined, the system continues to compute the amplitudes of the four most recent pulses, this time in order to compare the sum of the amplitudes (HSUM) with the threshold value. The comparison does not begin until four pulses have been detected following the derivation of HMAX. The actual threshold level is equal to one-half HMAX (the lowest integral value in case HMAX is odd) plus 4, corresponding to a fixed offset of 2 mm Hg. The formula for the threshold value (see lines 376 and 377 of the source listing) was determined by experiment; the formula specified is that which provides the most consistent, accurate diastolic pressure values.

Theoretically, it is possible to derive an HMAX value based solely upon the amplitude of the largest pulse, and to determine diastolic pressure when a single pulse amplitude falls below a threshold level which is a function of the maximum amplitude. But by using sliding averages, to determine both the threshold value itself and when the threshold test is passed, errors are avoided which might otherwise be introduced as a result of abnormally large or small pulse amplitudes, e.g., artifacts.

Figure 23:
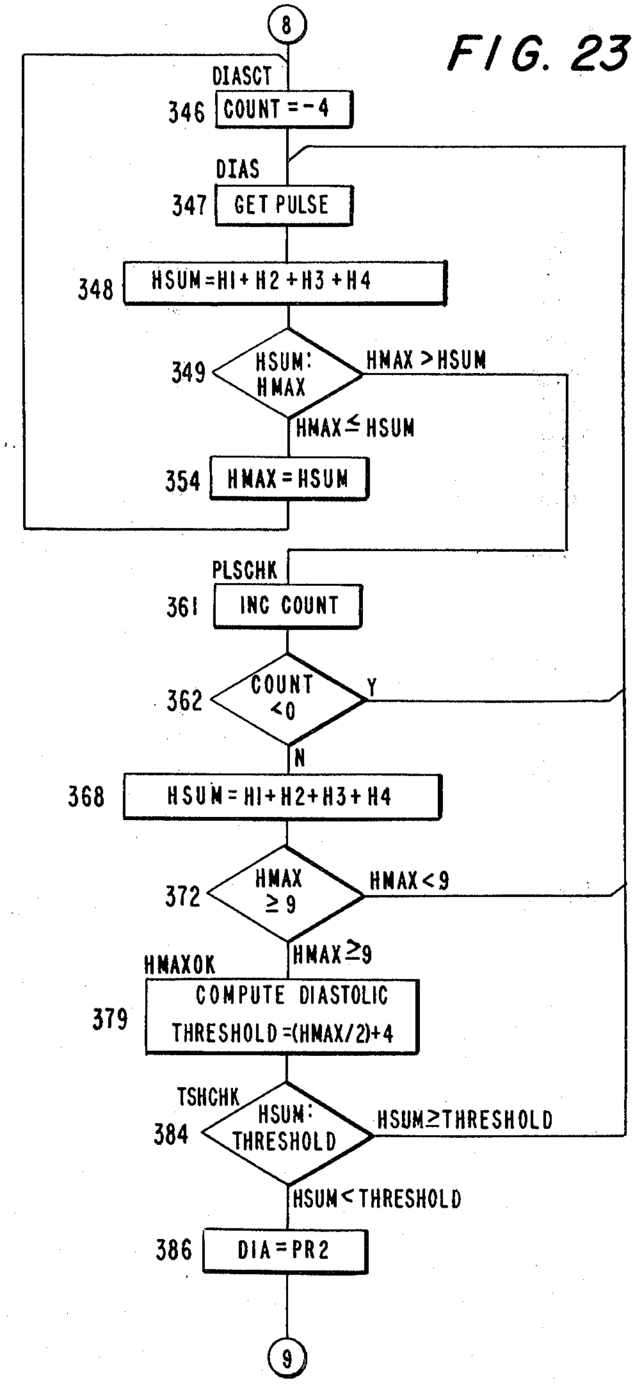

The flow chart for the diastolic pressure measurement is depicted in FIG. 23. At line 346, COUNT is set equal to −4. This counter is used to make sure that the threshold test is not performed until at least four pulses have been detected following the calculation of HMAX; at least four pulses are required before the threshold test is performed for the first time.

At line 347, the PLS subroutine is called and a pulse amplitude (H4) is derived. At line 348, the sum of this most recent pulse amplitude, and the three preceding pulse amplitudes, is computed. It will be recalled that HSUM is computed starting at line 330 at the end of systolic pressure processing (see FIG. 20). At this time, HMAX is set equal to the first HSUM. At line 349 in FIG. 23, the most recent HSUM is compared to the currently maintained HMAX value. If HSUM is greater than or equal to HMAX, at line 354 HMAX is up-dated. Since HMAX has only now been determined (and it may yet be changed), the system must wait until at least four more pulses are detected before performing the threshold test. Thus a jump is made back to line 346, at which time COUNT is re-initialized to −4.

But whenever the most recently computed HSUM value is less than HMAX, the test starting at line 349 causes a branch to line 361. Since the threshold test should not be performed until at least four pulses have been detected following calculation of HMAX (and COUNT is reset to −4 whenever a new HMAX is determined), COUNT is incremented and then tested to see if it is still negative. If it is, the test starting at line 362 causes a branch back to line 347, at which time another pulse is operated upon. The fourth pulse following the derivation of HMAX causes COUNT to be incremented to 0, and all succeeding pulses cause COUNT to be positive. Thus the test starting at line 362 controls an advance to line 368, at which time HSUM is calculated.

Before actually computing the threshold value and performing the threshold test, the value of HMAX is checked to see if it is greater than or equal to 9. This value corrresponds to at least three pulse amplitudes of value 2 and one of value 3 (which, in turn, correspond to at least three pulses of 1 mm Hg in amplitude, and one pulse of 1.5 mm Hg in amplitude). If all of the pulses are so weak that HMAX does not at least equal 9, a return is made to line 347; it is assumed that a valid HMAX has not yet been computed even though no HSUM value has exceeded the currently maintained HMAX value. (If this results in diastolic pressure not being computed before the 3-second timer times out, then the "dIA Error" message is displayed— it is better to indicate that an error occurred, than it is to display what is probably an erroneous result.)

But if HMAX is at least equal to 9, starting at line 379 the threshold value is calculated. Starting at line 384, the most recently computed HSUM value is compared with the threshold. Until the threshold test is passed, a branch is made back to line 347 and another pulse is examined. But as soon as HSUM is less than the threshold value, at line 386 the diastolic pressure value DIA is set equal to PR2, the occluding cuff pressure at the onset of the second of the four pulses which collectively passed the threshold test.

Referring to the source listing, at line 346 COUNT is set equal to −4. As shown in the flow chart of FIG. 23, the PLS subroutine is then called, following which a call is made to the HSUM subroutine. At lines 349–352, HSUM is compared with HMAX. HMAX is first stored in the accumulator, following which it is complemented and incremented. From the call to the HSUM subroutine at line 348, AEX contains HSUM. Consequently, when the contents of AEX are added to the contents of the accumulator at line 352, the difference HSUM-HMAX appears in the accumulator. The JB7 test at line 353 causes a branch to line 361 if the result is negative, i.e., if HMAX is greater than HSUM. But if HSUM is greater than or equal to HMAX, at line 354 HSUM is moved from AEX to the accumulator, and at line 355 HSUM is moved from the accumulator to the data memory location which is used to store HMAX. Finally, a jump is made back to line 346 at which time COUNT is re-initialized to −4.

Starting at line 361, the system determines whether at least four pulses have been detected following the derivation of HMAX. COUNT is incremented and then stored in the accumulator. If COUNT is negative, the JB7 test at line 363 cause a jump back to line 347, at which time another pulse is examined. Otherwise, the system moves on to line 368 at which time HSUM is computed once again. (Since HSUM is still stored in AEX from the previous call at line 348 to the same subroutine, the instruction at line 368 may be omitted.)

Starting at line 372, a check is made to see whether HMAX is equal to at least 9. HMAX is moved to the accumulator and −9 is then added to it. In HEX notation, −9 is F7. If HMAX is 8 or less, when HMAX and −9 are added together, the most significant nibble in the accumulator will be a HEX F. No carry is generated, and the JNC instruction at line 374 causes a jump to line 347. But if HMAX is at least equal to 9, the most significant nibble in the accumulator will switch from an F to a 0, and a carry will be generated; the system moves on to line 379, at which time the threshold value is computed. (Instead of repeatedly calculating the threshold value, it could alternatively be calculated only once after HMAX is set at lines 331 and 355. But there is sufficient time available to repeatedly calculate the value.)

HMAX is first moved to the accumulator. By then clearing the carry bit and rotating the accumulator to the right, HMAX is halved, as shown by the comment in line 381. At line 382, the value 3 is added to the contents of the accumulator. By then forming the one's complement of the accumulator contents at line 383, the accumulator contains the value—((HMAX/2)+4), in two's complement arithmetic.

The threshold test is performed starting at line 384. Since AEX still contains the value HSUM from the previous call to the HSUM subroutine, it is apparent that the ADD instruction at line 384 forms in the accumulator the difference of HSUM and the threshold value depicted in line 383. As long as the threshold value is less than HSUM, a carry is generated, and the JC test at line 385 causes a jump to line 347. But if the threshold test is passed, at line 386 and 387 registers R0 and R1 are made to point respectively to PR2 and DIA, and the call to the DMOVE subroutine at line 388 sets DIA equl to PR2. This concludes the diastolic pressure processing.

Referring back to the description of the flow chart at the bottom of FIG. 18, it will be recalled that PLSVLD is set equal to FF at line 881 as soon as a pulse is detected in the 3-second timing interval; a determination of diastolic pressure, together with PLSVLD being equal to FF, is supposed to stop the processing and to control the display of the final values. This is accomplished by the instructions at lines 389–382.

Figure 24:
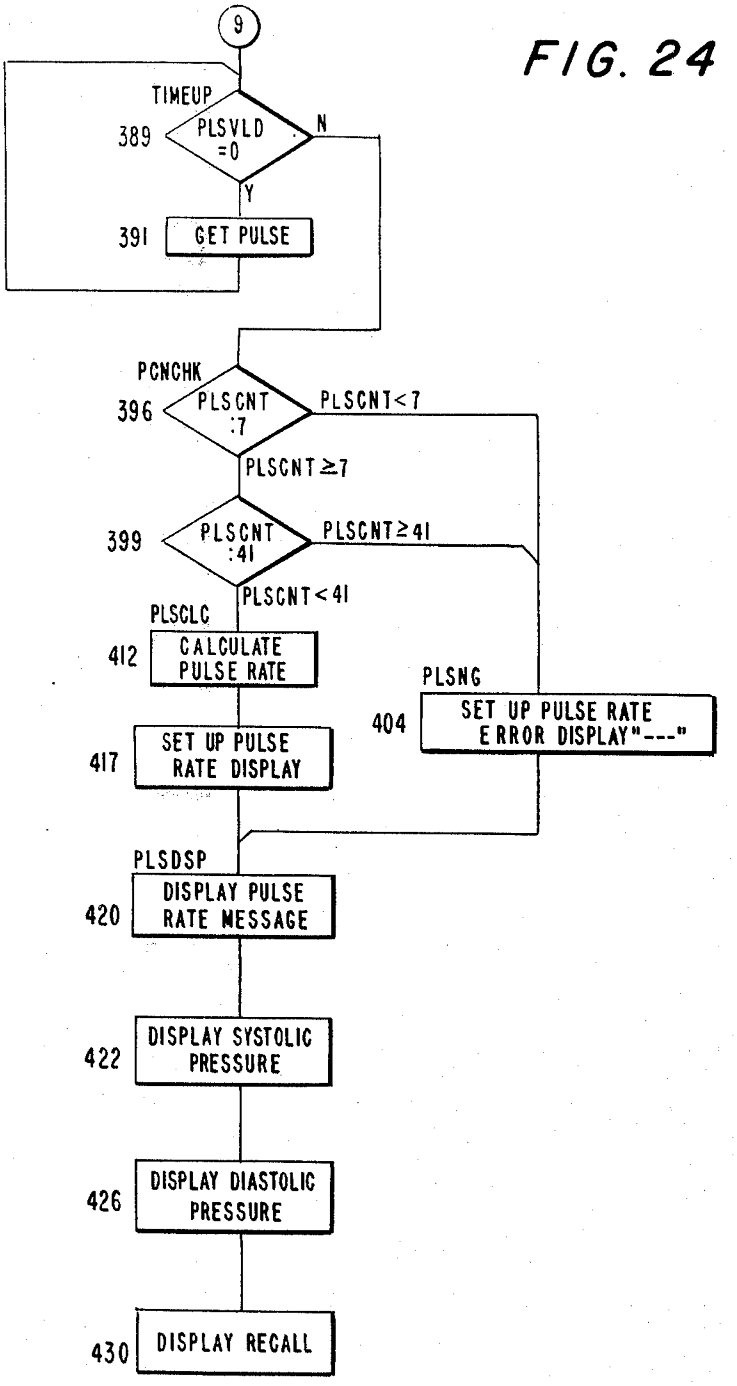

At line 389, PLSVLD is moved to the accumulator and, at line 390, the JNZ instruction checks whether PLSVLD is still equal to 0 or whether it has been set to FF. If it is equal to FF, a jump is made to line 396—all of the processing has now been completed. But if PLSVLD is still equal to 0, the system remains in a loop by calling the PLS subroutine at line 391, and then jumping back to line 389. The continuous calls to the PLS subroutine control the setting of PLSVLD to FF if a pulse is detected in the 3-second timing interval, following which the test at line 390 causes a jump to line 396. (If the 3-second timing interval times out before PLSVLD is set to FF, the "dIA Error" message is displayed as described above in connection with the flow chart at the top of FIG. 18.) The top of the flow chart of FIG. 24 depicts the instructions at lines 389–392.

Once the system reaches line 396, it is ready to display the three final values—systolic pressure, diastolic pressure and pulse rate. However, before doing so a check is made on the pulse rate to verify that it is within reasonable bounds.

At line 396, −7 (HEX F9) is first moved into the accumulator and at the next line the value of PLSCNT is added to it. If PLSCNT is 6 or less, the most significant nibble in the accumulator remains equal to F and the JB7 instruction at line 398 causes a jump to line 404. The systolic and diastolic pressure measurements are still displayed, but three dashes are displayed instead of the pulse rate to indicate that the pulse rate has not been determined correctly. But if PLSCNT is at least equal to 7 (corresponding to a pulse rate of 42 beats per minute since at least 7 pulses were detected during a 10-second interval), the value −34 is added to the accumulator at line 399. The accumulator thus represents a total value of PLSCNT −41. At line 400, a jump is made to line 412 if the most significant bit in the accumulator is a 1, indicating a negative value. If it is not a 1, it means that PLSCNT is at least equal to 41, corresponding to a pulse rate of 246 beats per minute. This is too high a value, and the error message is formed starting at line 404. Thus it is apparent that the minimum valid pulse rate is 42 beats per minute and the maximum is 240 beats per minute (corresponding to a PLSCNT value of 40).

The error message for the pulse rate is formed by loading BCD0 and BCD1 with four BCD "digit" offsets which represent a blank followed by three dashes. (A blank is controlled by energizing none of the anode segments of a character position, and a dash is controlled by energizing only the middle segment.) The accumulator is first loaded with two 4-bit values which represent a blank and a dash, and AEX is then loaded with two 4-bit values, each of which represents a dash. Register R0 is then made to point to BCD0, and at lline 407 the call to the DST subroutine loads BCD0 and BCD1 with the pulse-rate error message segment information. At line 408, a jump is made to line 420, at which point the three dashes to be displayed are formed. Lines 412–419 are executed only if the pulse-rate error message is not to be formed, i.e., if the JB7 instruction at line 400 causes a jump to line 412.

At line 412, PLSCNT is moved into the accumulator, and at the next two lines the same value is added to the accumulator two more times. Thus after the instruction at line 414 is executed, the accumulator contains three times the value of PLSCNT. The ADD instruction at line 414 sets the carry flag to a 0, so the rotate (left) instruction at line 415 causes the least significant bit in the accumulator to be a zero. The rotate instruction shifts the contents of the accumulator one position to the left, in effect multiplying it by two; the net result is that six times PLSCNT appears in the accumulator, the actual pulse rate in beats per minute.

At line 416, AEX is loaded with 0 and at the next line register R0 is made to point to PTMP. AEX and the accumulator now represent the pulse rate to be displayed, and register R0 points to the first of the two locations (PTMP and PTMP+1) which are now used to store the final pulse rate value. These two locations may be used because they are no longer required to store current sample values. The call at line 418 to the DST subroutine loads the pulse count is PTMP and PTMP+1, and then a call is made to the BINBC1 subroutine (line 636). Register R1 is first made to point to BCD0. The call at line 637 to DMOVE (line 902) causes the same two bytes to be transferred from PTMP and PTMP+1 to BCD0 and BCD1. At line 638, the jump to line 657 converts the binary pulse count value in BCD0 and BCD1 to four BCD "digits" (the first of which represents a blank), following which a return is made to line 420.

It is starting at line 420 that the display is actually formed. It is the pulse rate which is first displayed. Referring to line 523, it will be recalled that when the DBCD subroutine is called, four characters are formed (a blank, usually followed by three digits, although three dashes in the case of a pulse-rate error message)—provided the accumulator initially contains the address in the DTBL table which corresponds to the first character position in the display which is to be operated upon. The pulse rate message is displayed in the last four positions, and consequently at line 420 the accumulator is loaded with the address of the ninth location in the DTBL table. The call to the DBCD subroutine at line 421 then controls a display of the pulse rate value (a blank, followed by three digits) or a pulse-rate error message (a blank, followed by three dashes).

In order to display the systolic pressure measurement, at line 422 register R0 is first made to point to SYS, the final systolic pressure value. The call at the next line to the BINBCD subroutine causes one-half of this value, in BCD form, to be loaded into BCD0 and BCD1; for systolic pressure and diastolic pressure displays to be formed, the SYS and DIA values must be halved since they represent twice the actual values, unlike the final value for the pulse rate which is the actual value. At line 424, the accumulator is loaded with the address of the first location in the DTBL table, since the systolic pressure is displayed in the first four positions (a blank, followed by three digits). The call to the DBCD subroutine then forms the display. The diastolic pressure measurement is formed in exactly the same way, except that register R0 is made to point to DIA, the diastolic pressure value, and the accumulator is initially loaded with the address of the fifth location in the DTBL table since the diastolic pressure is displayed in the middle, between systolic pressure and pulse rate.

Finally, at line 430, a jump is made to the DSPEND routine starting at line 453. The display persists for only ten seconds, following which the pulse light is turned on to inform the operator that the display can be recalled by depressing the recall/cuff button. The flow chart for lines 396–430 is depicted in FIG. 24.

Although this description of the firmware listing "ends" with line 430, a review of all lines following this one will reveal that they have already been described. Starting with line 436, the listing contains various subroutines and data (segment tables and message information), all of which have already been described. At the end of the listing, there is a user symbol table which provides the ROM location, i.e., HEX address, corresponding to each labelled instruction or byte of fixed data, and the HEX code representations of the labelled locations in the 64-location data memory.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

I claim:

1. A method for determining when a sufficiently high occluding pressure exists in the cuff of a blood pressure measuring instrument; said instrument including means for pumping up the cuff pressure in discrete steps, means for allowing air in said cuff to bleed out, and means for periodically sampling the instantaneous cuff pressure; comprising the steps of:

(a) maintaining a relative peak pressure value and continuously up-dating it to equal a newly taken sample if the latter is larger, (b) maintaining a relative minimum pressure value and continuously up-dating it to equal a newly taken sample if the latter is smaller than the smallest sample previously taken subsequent to the last up-dating of said relative peak pressure value, (c) starting a time measure whenever said relative peak pressure value is up-dated, (d) determining the pressure rises which occur during said time measure, and (e) after said time measure has reached a predetermined length, determining that a sufficiently high occluding pressure exists if all of the pressure rises were less than a pre-set threshold value during said time measure.

2. A method in accordance with claim 1 wherein in step (e) a sufficiently high occluding pressure is determined to exist even if a pressure rise exceeded said pre-set threshold value if said rise did not persist for longer than a predetermined interval.

3. A method in accordance with claim 2 wherein said instrument includes means for displaying messages and pressure values, and further including the step of:

(f) displaying pressure values corresponding to samples falling within at least a portion of the pressure range over which the instrument is operative.

4. A method in accordance with claim 3 further including the step of:

(g) displaying a message indicative of a high cuff pressure existing when a sample exceeds a predetermined value.

5. A method in accordance with claim 3 further including the step of:

(g) displaying a message indicative of a low cuff pressure existing when a sample is less than a predetermined value.

6. A method in accordance with claim 5 further including the step of:

(h) displaying a message indicative of a low cuff pressure existing if during said time measure a pressure rise exceeds said pre-set threshold value and said rise persists for longer than said predetermined interval.

7. A method in accordance with claim 1 wherein said instrument includes means for displaying messages and pressure values, and further including the step of:

(f) displaying pressure values corresponding to samples falling within at least a portion of the pressure range over which the instrument is operative.

8. A method in accordance with claim 7 further including the step of:

(g) displaying a message indicative of a high cuff pressure existing when a sample exceeds a predetermined value.

9. A method in accordance with claim 7 further including the step of:

(g) displaying a message indicative of a low cuff pressure existing when a sample is less than a predetermined value.

10. A method in accordance with claim 9 further including the step of:

(h) displaying a message indicative of a low cuff pressure existing if during said time measure a pressure rise exceeds said pre-set threshold value and said rise persists for longer than a predetermined interval.

11. A method in accordance with claim 1 further including the initial step of sampling the cuff pressure when the cuff is at atmospheric pressure, and wherein each newly taken sample operated upon is the actual sample value taken by said sampling means minus the sample value taken during said initial step.

12. A method in accordance with claim 1 wherein said predetermined length is at least two seconds.

13. A method for determining when a sufficiently high occluding pressure exists in the cuff of a blood pressure measuring instrument; said instrument including means for pumping up the cuff pressure, means for allowing air in said cuff to bleed out, and means for periodically sampling the instantaneous cuff pressure; comprising the steps of:

(a) maintaining a relative peak pressure value and continuously up-dating it in accordance with the value of a newly taken sample, (b) maintaining a relative minimum pressure value and continuously up-dating it in accordance with the value of a newly taken sample, (c) starting a time measure whenever said relative peak pressure value is up-dated, (d) determining the pressure rises which occur during said time measure, and (e) when said time measure reaches a predetermined length, determining that a sufficiently high occluding pressure exists if the maximum pressure rise during said time measure was less than a pre-set threshold value.

14. A method in accordance with claim 13 wherein in step (e) a sufficiently high occluding pressure is determined to exist even if a pressure rise exceeded said pre-set threshold value if said rise did not persist for longer than a predetermined interval.

15. A method in accordance with claim 13 wherein said instrument includes means for displaying messages and pressure values, and further including the step of:

(f) displaying pressure values corresponding to samples falling within at least a portion of the pressure range over which the instrument is operative.

16. A method in accordance with claim 15 further including the steps of:

(g) displaying a message indicative of a high cuff pressure existing when a sample exceeds a predetermined value.

17. A method in accordance with claim 15 further including the step of:

(g) displaying a message indicative of a low cuff pressure existing when a sample is less than a predetermined value.

18. A method in accordance with claim 17 further including the step of:

(h) displaying a message indicative of a low cuff pressure existing if during said time measure a pressure rise exceeds said pre-set threshold value and said rise persists for longer than a predetermined interval.

19. A method in accordance with claim 13 further including the initial step of sampling the cuff pressure when the cuff is at atmospheric pressure, and wherein each newly taken sample operated upon is the actual sample value taken by said sampling means minus the sample value taken during said initial step.

20. A method in accordance with claim 13 wherein said predetermined length is at least two seconds.

* * * * *